United States Patent
Durocher

(10) Patent No.: US 11,982,677 B2
(45) Date of Patent: May 14, 2024

(54) DIMERIZATION SCREENING ASSAYS

(71) Applicant: VedaBio, Inc., San Diego, CA (US)

(72) Inventor: Daniel Durocher, San Diego, CA (US)

(73) Assignee: VedaBio, Inc., San Diego, CA (US)

( * ) Notice: Subject to any disclaimer, the term of this patent is extended or adjusted under 35 U.S.C. 154(b) by 0 days.

(21) Appl. No.: 18/372,072

(22) Filed: Sep. 23, 2023

(65) Prior Publication Data

US 2024/0110920 A1 Apr. 4, 2024

Related U.S. Application Data

(60) Provisional application No. 63/425,425, filed on Nov. 15, 2022, provisional application No. 63/412,512, filed on Oct. 2, 2022.

(51) Int. Cl.
*G01N 33/68* (2006.01)
*C12N 9/22* (2006.01)

(52) U.S. Cl.
CPC ......... *G01N 33/6845* (2013.01); *C12N 9/22* (2013.01); *C12N 2310/20* (2017.05)

(58) Field of Classification Search
None
See application file for complete search history.

(56) References Cited

U.S. PATENT DOCUMENTS

| | | |
|---|---|---|
| 10,253,365 B1 | 4/2019 | Doudna et al. |
| 10,266,886 B2 | 4/2019 | Abudayyeh et al. |
| 10,266,887 B2 | 4/2019 | Abudayyeh et al. |
| 10,337,051 B2 | 7/2019 | Doudna et al. |
| 10,377,998 B2 | 8/2019 | Zhang et al. |
| 10,494,664 B2 | 12/2019 | Doudna et al. |
| 11,021,740 B2 | 6/2021 | Abudayyeh et al. |
| 11,060,115 B2 | 7/2021 | Severinov et al. |
| 11,104,937 B2 | 8/2021 | Abudayyeh et al. |
| 11,118,224 B2 | 9/2021 | Doudna et al. |
| 11,149,259 B2 | 10/2021 | Zhang et al. |
| 11,174,470 B2 | 11/2021 | Harrington et al. |
| 11,174,515 B2 | 11/2021 | Abudayyeh et al. |
| 11,273,442 B1 | 3/2022 | Chen et al. |
| 11,421,250 B2 | 8/2022 | Severinov et al. |
| 11,447,824 B2 | 9/2022 | Doudna et al. |
| 2014/0377748 A1 | 12/2014 | Tan et al. |
| 2016/0083785 A1 | 3/2016 | Bone et al. |
| 2018/0023081 A1 | 1/2018 | Hagedorn et al. |
| 2018/0155716 A1 | 6/2018 | Zhang et al. |
| 2018/0282722 A1 | 10/2018 | Jakimo et al. |
| 2019/0112648 A1 | 4/2019 | Schaal et al. |
| 2019/0201550 A1 | 7/2019 | Maeder et al. |
| 2019/0241954 A1 | 8/2019 | Doudna et al. |
| 2019/0256900 A1 | 8/2019 | Zhang et al. |
| 2020/0010879 A1 | 1/2020 | Doudna et al. |
| 2020/0056167 A1 | 2/2020 | Dong et al. |
| 2020/0157611 A1 | 5/2020 | Qi et al. |
| 2020/0165594 A1 | 5/2020 | Zhang et al. |
| 2020/0231975 A1* | 7/2020 | Gootenberg ......... C12N 15/113 |
| 2020/0277600 A1 | 9/2020 | Zhang et al. |
| 2020/0392473 A1 | 12/2020 | Zhang et al. |
| 2021/0102183 A1 | 4/2021 | Cameron et al. |
| 2021/0102242 A1 | 4/2021 | Chen et al. |
| 2021/0108267 A1 | 4/2021 | Zhang et al. |
| 2021/0163944 A1 | 6/2021 | Zhang et al. |
| 2021/0166783 A1 | 6/2021 | Shmakov et al. |
| 2021/0269866 A1 | 9/2021 | Zhang et al. |
| 2021/0317527 A1 | 10/2021 | Doudna et al. |
| 2021/0388437 A1 | 12/2021 | Doudna et al. |
| 2022/0025463 A1 | 1/2022 | Abudayyeh et al. |
| 2022/0333208 A1 | 10/2022 | Gootenberg et al. |
| 2023/0193368 A1 | 6/2023 | Rananaware et al. |

FOREIGN PATENT DOCUMENTS

| | | |
|---|---|---|
| CN | 114058679 A | 2/2022 |
| CN | 114262730 A | 4/2022 |
| WO | WO 2014/143228 A1 | 9/2014 |
| WO | WO 2016/201138 A1 | 12/2016 |
| WO | WO 2020/191248 | 9/2020 |
| WO | WO 2020/191376 | 9/2020 |
| WO | WO 2021/021532 A1 | 2/2021 |
| WO | WO 2021/108717 A2 | 6/2021 |
| WO | WO 2021/146534 A1 | 7/2021 |
| WO | WO 2021/236651 A1 | 11/2021 |
| WO | WO 2022/061166 A1 | 3/2022 |
| WO | WO 2022/133108 A2 | 6/2022 |
| WO | WO 2022/266513 A2 | 12/2022 |

(Continued)

OTHER PUBLICATIONS

Sha et al., Cascade CRISPR/cas enables amplification-free microRNA sensing with fM-sensitivity and single-base specificity, 2021, Chem. Commun., 57, 247-250 (Year: 2021).*

Tang et al., The CRISPR-Cas toolbox for analytical and diagnostic assay development, Chem. Soc. Rev., 2021, 50, 11844-11869 (Year: 2021).*

Zhou et al., High-throughput split protein profiling by combining transposon mutagenesis and regulated protein-protein interactions with deep-sequencing, 2022, International Journal of Biological Macromolecules, 203, 543-552 (Year: 2022).*

Click Chemistry, "Introduction: Click Chemistry", Chem. Rev. 2021, doi/10.1021/acs.chemrev.1c00469, p. 6697-6698.

MacConnell, et al., "An Integrated Microfluidic Processor for DNA-Encoded Combinatorial Library Functional Screening", ACS Combinatorial Science, DOI: 10.1021/acscombsci.6b00192, p. 181-192.

(Continued)

*Primary Examiner* — Nancy J Leith
*Assistant Examiner* — Jessica D Parisi
(74) *Attorney, Agent, or Firm* — Sarah Brashears

(57) ABSTRACT

The present disclosure relates to compositions of matter and assay methods used to screen for molecular dimerization events using a two-ribonucleoprotein complex signal boost assay. The compositions and methods provide a readout upon detection of dimerization of molecules and may be implemented in a high throughput manner using libraries of tens to hundreds to thousands of putative binding partners.

29 Claims, 16 Drawing Sheets
Specification includes a Sequence Listing.

(56) References Cited

FOREIGN PATENT DOCUMENTS

| WO | WO 2023/278629 A1 | 1/2023 |
|---|---|---|
| WO | WO 2023/287669 A2 | 1/2023 |
| WO | WO 2023/015259 A2 | 2/2023 |
| WO | WO 2023/056451 A1 | 4/2023 |
| WO | WO 2023/081902 A1 | 5/2023 |
| WO | WO 2023/114052 A1 | 6/2023 |
| WO | WO 2023/114090 A2 | 6/2023 |

OTHER PUBLICATIONS

Mendes, et al., "High-throughput Identification of DNA-Encoded IgG Ligands that Distinquish Active and Latent Mycobacterium Tuberculosis Infections", ACS Chem Biol., Jan. 20, 2017, doi:10.1021/acschembio.6b00855, p. 1-19.
Gerry, et al., "Unifying principles of bifunctional, proximity-inducing small molecules", Nat Chem Biol., Apr. 1, 2020, doi:10.1038/s41589-020-0469-1, p. 1-24.
Bowley, et al., "Libraries against libraries for combinatorial selection of replicating antigen-antibody pairs", PNAS, Feb. 3, 2009, vol. 106, doi:10.1073/pnas.0812291106, p. 1380-1385.
Kempton, et al., "Multiple Input Sensing and Signal Integration Using a Split Cas12a System", Molecular Cell, Apr. 2, 2020, p. 184-191.
Holt, et al., "By-passing selection: direct screening for antibody-antigen interactions using protein arrays", Nucleic Acids Research, Jun. 16, 2000, vol. 28, No. 15, p. 1-5.
Delley, et al., "Microfluidic particle zipper enables controlled loading of droplets with distinct particle types", Lab Chip., Jul. 14, 2020, doi:10.1039/d01c00339e, p. 2465-2472.
Li, et al., "Applying CRISPR-Cas12a as Signal Amplifier to Construct Biosensors for Non-DNA Targets in Ultra-low Concentrations", ACS Sensors, doi: 10.1021/acssensors.9b02305, pp. 1-23, Mar. 12, 2020.
Kim, et al., "Chimeric crRNAs with 19 DNA residues in the guide region show retained DNA cleavage activity of Cas9 with a potential to improve the specificity", The Royal Society of Chemistry, pp. 1-16, 2019.
Kim, et al., "Enhancement of target specificity of CRISPR-Cas12a by using a chimeric DNA-RNA guide", Nucleic Acids Research, doi: 10.1093/nar/gkaa605, vol. 48, No. 15, pp. 8601-8616, Jul. 20, 2020.
Swarts, et al., "Mechanistic Insights into the Cis- and Trans-acting Deoxyribonuclease Activities of Cas12a", Mol Cell, doi: 10.1016/j.molcel.2018.11.021, pp. 1-28, Feb. 7, 2019.
Nguyen, et al., "Enhancement of trans-cleavage activity of Cas12a with engineered crRNA enables amplified nucleic acid detection", Nature Communications, doi: 10.1038/s41467-020-18615-1, pp. 1-13, 2020.
Ooi, et al., "An engineered CRISPR-Cas12a variant and DNA-RNA hybrid guides enable robust and rapid COVID-10 testing", Nature Communications, doi: 10.1038/s41467-021-21996-6, pp. 1-23, 2021.
Shi, et al., "A CRISPR-Cas autocatalysis-driven feedback amplification network for supersensitive DNA diagnostics", Science Advances, doi: 10.1126/sciadv.abc7802, pp. 1-9, Jan. 27, 2021.
The Board of Trustees of the University of Illinois, "CRISPR Cascade", International PCT Application No. PCT/US22/33985, filed Jun. 17, 2022.
Chen, et al., "CRISPR-Cas12a target binding unleashes indiscriminate single-stranded DNase activity", Howard Hughes Medical Institute, Science, 360(6387), pp. 436-439, Apr. 27, 2018.
Liu, et al., "Accelerated RNA detection using tandem CRISPR nucleases", Nature Chemical Biology, vol. 17, doi:10.1038/s41589-021-0084202, pp. 982-988, Sep. 2021.
Gootenberg, et al., "Nucleic acid detection with CRISPR-Cas13a/C2c2", Science, doi:10.1126/science.aam9321, pp. 438-442, Apr. 28, 2017.
Fozouni, et al., "Amplification-free detection of SARS-CoV-2 with CRISPR-Cas13a and mobile phone microscopy", Cell, doi.org/10.1016/j.cell.2020.12.001, pp. 323-333, Jan. 21, 2021.
Kaminski, et al., "CRISPR-based diagnostics", Nature Biomedical Engineering, vol. 5, doi.org/10.1038/s41551-021-00760-7, pp. 643-656, Jul. 2021.
Zhou, et al., "CRISPR/Cas13a Powered Portable Electrochemiluminescence Chip for Ultrasensitive and Specific MiRNA Detection", Advanced Science News, doi: 10.1002/advs.201903661, pp. 1-10, 2020.
Zhao, et al., "CRISPR-Cas13a system: A novel tool for molecular diagnostics", Frontiers in Microbiology, doi:10.3389/fmicb.2022.1060947, pp. 1-18, Dec. 8, 2022.
Zhou, et al., "A Decade of CRISPR Gene Editing in China and Beyond: A Scientometric Landscape", The CRISPR Journal, vol. 4, No. 3, doi:10.1089/crispr.2020.0148, pp. 313-320, 2021.
Shinoda, et al., "Automated amplification-free digital RNA detection platform for rapid and sensitive SARS-CoV-2 diagnosis", Communications Biology, doi.org/10.1038/s42003-022-03433-6, pp. 1-8, May 26, 2022.
Gupta, et al., "Cas13d: A New Molecular Scissor for Transcriptome Engineering, Frontiers in Cell and Developmental Biology", vol. 10, doi:10.3389/fcell.2022.866800, pp. 1-22, Mar. 31, 2022.
Schunder, et al., "First indication for a functional CRISPR/Cas system in Francisella tularensis", International Journal of Medical Microbiology, vol. 303, Issue 2, doi:10.1016/j.ijmm.2012.11.004, pp. 1-29, Mar. 2013.
Sha, et al., "Cascade CRISPR/cas enables amplification-free microRNA sensing with fM-sensitivity and single-base-specificity", ChemComm, doi:10.1039/d0cc06412b, pp. 247-250 and 1-15, 2021.
Yang, et al., "Engineered LwaCas13a with enhanced collateral activity for nucleic acid detection", Nature Chemical Biology, vol. 19, doi:10.1038/s41589-022-01135-y, pp. 45-54, Jan. 2023.
East-Seletsky, et al., "RNA targeting by functionally orthogonal Type VI-A CRISPR-Cas enzymes", Howard Hughes Medical Institute, Mol Cell, pp. 373-383, May 4, 2017.
Schmidt, et al., "Application of locked nucleic acids to improve aptamer in vivo stability and targeting function", Nucleic Acids Research, vol. 32, No. 19, doi:10.1093/nar/gkh862, pp. 5757-5765, Oct. 27, 2004.
Makarova, et al., "Evolutionary classification of CRISPR-Cas systems: a burst of class 2 and derived variants", Nature Reviews | Microbiology, vol. 18, pp. 67-83, Feb. 2020.
Gleditzsch, et al., "PAM identification by CRISPR-Cas effector complexes: diversified mechanisms and structures", RNA Biology, vol. 16, No. 4, doi.org/10.1080/15476286.2018.1504546, pp. 504-517, Jul. 20, 2018.
Kellner, et al., "SHERLOCK: Nucleic acid detection with CRISPR nucleases", Nat Protoc., doi:10.1038/s41596-019-0210-2, pp. 2986-3012, Oct. 2019.
Liu, et al., "Directed Evolution of CRISPR/Cas Systems for Precise Gene Editing", Trends in Biotechnology, vol. 39, No. 3, Mar. 2021, p. 262-273.
International Search Report and Written Opinion for International Application No. PCT/US2022/036610, dated Jun. 29, 2023, p. 1-93.
International Search Report and Written Opinion for International Application No. PCT/US22/52320, dated Jun. 15, 2023, p. 1-46.
International Search Report and Written Opinion for International Application No. PCT/US2022/052032, dated Apr. 18, 2023, p. 1-19.
Zhang, et al, "An aM-level cascade CRISPR-Dx system (ASCas) for rapid detection of RNA without pre-amplification", Biosensors and Bioelectronics, doi:10.1016/j.bios.2023.115248, Mar. 28, 2023, p. 1-5.
Zeng, et al., "Rapid RNA detection through intra-enzyme chain replacement-promoted Cas13a cascade cyclic reaction without amplification", Analytica Chimica Acta, doi:10.1016/j.aca.2022.340009, May 31, 2022, p. 1-10.
Collias, et al., "CRISPR technologies and the search for the PAM-free nuclease", Nature Communications, doi: 10.1038/s41467-020-20633-y, 2021, p. 1-12.
Huyke, et al., "Enzyme Kinetics and Detector Sensitivity Determine Limits of Detection of Amplification-Free CRISPR-Cas12 and

(56) References Cited

OTHER PUBLICATIONS

CRISPR-Cas13 Diagnostics", Analytical Chemistry, doi:10.1021/acs.analchem.2601670, Jun. 27, 2022, p. 9826-9834.

Mullally, et al., "5' modifications to CRISPR-Cas9 gRNA can change the dynamics and size of R-loops and inhibit DNA cleavage", Nucleic Acids Research, DOI:10.1093/nar/gkaa477, Jun. 2020, vol. 48, No. 12, p. 6811-6823.

Hong, et al., "Comparison and optimization of CRISPR/dCas9/gRNA genome-labeling systems for live cell imaging", Genome Biology, DOI: 10.1186/s13059-018-1413-5, 2018, p. 7-8.

Li, et al., "CRISPR-Cas 12a has both cis- and trans-cleavage activities on single-stranded DNA", Cell Research, DOI: 10.1038/s41422-018-0022-x, Feb. 5, 2018, p. 1-3.

Dong, et al., "An anti-CRISPR protein disables type V Cas12a by acetylation", PubMed, DOI:10.1038/s41594-019-0206-1, Feb. 28, 2023, p. 1-1.

Coehlo, et al., "CRISPR Guard protects off-target sites from Cas9 nuclease activity using short guide RNAs", Nature Communications, DOI: 10.1038/s41467-020-17952-5, Aug. 17, 2020, p. 1-12.

\* cited by examiner

DIMERIZATION SCREENING ASSAYS

RELATED APPLICATIONS

This application claims priority to U.S. Ser. No. 63/412,512, filed 2 Oct. 2022; and U.S. Ser. No. 63/425,425 filed 15 Nov. 2022 both of which are incorporated by reference in their entirety.

INCORPORATION BY REFERENCE OF SEQUENCE LISTING

Submitted herewith is an electronically filed sequence listing via EFS-Web a Sequence Listing XML, 11,000 bytes in size. The sequence listing is part of the specification of this specification and is incorporated by reference in its entirety.

FIELD OF THE INVENTION

The present disclosure relates to compositions of matter and assay methods used to screen for molecular dimerization events. The compositions and methods provide a readout upon detection of dimerization of molecules and may be implemented in a high throughput manner.

BACKGROUND OF THE INVENTION

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

A fundamental experiment in biochemistry is to determine whether two molecules interact with one another, as such interactions are essential to virtually every process in a living cell. Interactions include two proteins binding to each other, a small molecule binding to a protein, a protein binding to a nucleic acid, and molecules that bring other molecules into proximity to create multimeric complexes. There are various approaches to analyze interactions, including yeast and bacterial display, ribosome display, phage display, micro-engraving, and various methods of spatial addressing; however, what is needed are screening assays that may be performed in a high throughput manner, and are easily reprogrammable, robust, and offer a clear readout, as well as the instrumentation that facilitates such screening. The present disclosure addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides compositions of matter and assay methods to detect molecular dimerizations. The "dimerization screening assays" described herein comprise a first ribonucleoprotein (RNP) complex comprising a split Cas enzyme that, when reconstituted, is functional and exhibits both cis- and trans-cleavage activity. At least three basic embodiments of the dimerization screening assays are described. Two of the embodiments utilize blocked nucleic acid molecules (with one embodiment configuring a blocked nucleic acid molecule as a blocked primer molecule) that cannot activate a ribonucleoprotein complex until they are unblocked, and the third embodiment utilizes a blocked guide nucleic acid (i.e., blocked guide RNA or blocked gRNA) that cannot form an activated ribonucleoprotein complex until it is unblocked. All embodiments provide a dimerization screening assay that is robust and is easily reprogrammed by reconfiguring the dimerizer/split Cas enzyme fusion, as described in detail below.

The first two embodiments provide a reaction mixture comprising: a dimerizer/N-terminal portion of a split Cas enzyme that exhibits both cis- and trans-cleavage activity, a dimerizer/C-terminal portion of the split Cas enzyme, and a first gRNA which potentially will form a first ribonucleoprotein complex (RNP1); a second ribonucleoprotein complex (RNP2) comprising an intact Cas enzyme that also exhibits both cis- and trans-cleavage activity, and a second gRNA; RNP1 activating nucleic acids; either blocked nucleic acid molecules or blocked primer molecules, depending on the type of dimerization screening assay, for RNP2; and reporter moieties, which may be separate molecules from the blocked nucleic acid molecules, or the reporter moieties may be incorporated into and part of the blocked nucleic acid molecules. The split Cas enzyme is not activated and is unable to form RNP1 unless and until the N-terminal and C-terminal portions of the split Cas enzyme are brought into functional proximity by a dimerization event and the nuclease activity (both cis- and trans-cleavage activity) of the split Cas enzyme is reconstituted.

The third embodiment provides a reaction mixture comprising: a dimerizer/N-terminal portion of the split Cas enzyme that exhibits both cis- and trans-cleavage activity, a dimerizer/C-terminal portion of the split Cas enzyme, and a first gRNA which potentially will form a first ribonucleoprotein complex (RNP1); an intact Cas enzyme that also exhibits both cis- and trans-cleavage activity; blocked guide nucleic acids that, when unblocked, can form a second ribonucleoprotein complex (RNP2); RNP1 activating nucleic acids and RNP2 activating nucleic acids; and reporter moieties. Like the first two embodiments, in this embodiment, the split Cas enzyme is not activated and is unable to form RNP1 unless and until the N-terminal and C-terminal portions of the split Cas enzyme are brought into functional proximity by a dimerization event and the nuclease activity (both cis- and trans-cleavage activity) of the split Cas enzyme is reconstituted.

The present dimerization screening assays can detect putative binding pairs of interest (e.g., DNA, RNA and/or cDNA) at attamolar (aM) (or lower) limits. Importantly, the screening assays prevent "leakiness" that can lead to non-specific signal generation resulting in false positives. As described herein, "leakiness" is minimized by blocking components of RNP2 such that the second ribonucleoprotein complex is not activated until the components are unblocked. A particularly advantageous feature of the dimerization screening assays is that, with the exception of the putative dimerizers that are fused to the N-terminal and C-terminal portions of the split Cas enzyme, the dimerization screening assay components are the same in each assay no matter what putative binding pairs of interest are being detected.

Thus, there is in certain embodiments provided: a method for identifying a dimerization of binding partners comprising the steps of providing a reaction mixture comprising: a first binding partner/N-terminal portion of a split Cas enzyme, wherein the split Cas enzyme when reconstituted with the N-terminal portion and a C-terminal portion is capable of trans-cleavage nuclease activity; first guide nucleic acids; RNP1 activating nucleic acids, wherein the RNP1 activating nucleic acids comprise a sequence complementary to the first guide nucleic acids, and wherein binding of an RNP1 complex formed by reconstituting the split Cas enzyme and the first guide nucleic acid to the RNP1 activating nucleic acid activates trans-cleavage activity of the split Cas enzyme; RNP2s, wherein the RNP2s comprise a second guide nucleic acid and an intact second Cas enzyme comprising trans-cleavage nuclease activity and wherein the second intact Cas enzyme is a different Cas enzyme than the split Cas enzyme; and a plurality of blocked nucleic acid molecules comprising a sequence complementary to the second guide nucleic acid; and contacting the reaction mixture with a sample comprising a library of putative second binding partner/C-terminal portions of the split Cas enzyme under conditions that allow putative second binding partners to bind to the first binding partner of the first binding partner/N-terminal portion of the split Cas enzyme, and wherein if one of the putative second binding partners in the library of putative second binding partners binds to the first binding partner, the split Cas enzyme is reconstituted and forms an RNP1 with the first guide nucleic acids and RNP1 activating nucleic acids thereby initiating trans-cleavage of at least one of the blocked nucleic acid molecules and thereby producing at least one unblocked nucleic acid molecule, and wherein the at least one unblocked nucleic acid molecule binds to RNP2 initiating cleavage of at least one further blocked nucleic acid molecule; and detecting the at least one unblocked nucleic acid molecule, thereby detecting dimerization of binding partners in the sample.

In certain embodiments, there is provided: a reaction mixture for detecting dimerization of binding partners comprising: first binding partner/N-terminal portions of a split Cas enzyme and a second binding partner/C-terminal portion of a split Cas enzyme, wherein the split Cas enzyme when reconstituted with the N-terminal and C-terminal portions is capable of exhibiting trans-cleavage nuclease activity; first guide nucleic acids; RNP1 activating nucleic acids, wherein the RNP1 activating nucleic acids comprise a sequence complementary to the first guide nucleic acids, and wherein binding of an RNP1 complex formed by reconstituting the split Cas enzyme and the first guide nucleic acid to the RNP1 activating nucleic acid activates trans-cleavage activity of the split Cas enzyme; RNP2s, wherein the RNP2s comprise a second guide nucleic acid and an intact second Cas enzyme comprising trans-cleavage nuclease activity and wherein the second intact Cas enzyme is a different Cas enzyme than the split Cas enzyme; and a plurality of blocked nucleic acid molecules comprising a sequence complementary to the second guide nucleic acid.

In certain embodiments, there is provided: a method for identifying a dimerization of binding partners comprising the steps of: providing a reaction mixture comprising: first binding partner/N-terminal portions of a split Cas enzyme, wherein the split Cas enzyme when reconstituted with the N-terminal portion and a C-terminal portion is capable of exhibiting trans-cleavage nuclease activity; first guide nucleic acids; RNP1 activating nucleic acids, wherein the RNP1 activating nucleic acids comprise a sequence complementary to the first guide nucleic acids, and wherein binding of an RNP1 complex formed by reconstituting the split Cas enzyme and the first guide nucleic acid to the RNP1 activating nucleic acid activates trans-cleavage activity of the split Cas enzyme; RNP2s, wherein the RNP2s comprise a second guide nucleic acid and an intact second Cas enzyme comprising trans-cleavage nuclease activity and wherein the second intact Cas enzyme is a different Cas enzyme than the split Cas enzyme; a plurality of template molecules comprising sequence homology to the second guide nucleic acid; a plurality of blocked primer molecules comprising a sequence complementary to the template molecules, wherein the blocked primer molecules cannot be extended by a polymerase; and a polymerase and a plurality of nucleotides; contacting the reaction mixture with a sample comprising a library of putative second binding partner/C-terminal portions of the split Cas enzyme under conditions that allow putative second binding partners to bind to the first binding partner of the first binding partner/N-terminal portion of the split Cas enzyme, and wherein if one of the putative second binding partners in the library of putative second binding partners binds to the first binding partner the split Cas enzyme is reconstituted and forms an RNP1 with the first guide nucleic acids and RNP1 activating nucleic acids thereby initiating trans-cleavage of at least one of the blocked primer molecules and thereby producing at least one unblocked primer molecule that can be extended by the polymerase, the at least one unblocked primer molecule binds to one of the template molecules and is extended by the polymerase and nucleotides to form at least one synthesized activating molecule having a sequence complementary to the second guide nucleic acid, wherein the at least one synthesized activating molecule binds to the second guide nucleic acid, and wherein the RNP2 becomes active cleaving at least one additional blocked primer molecule in a cascade; and detecting the at least one unblocked primer molecule, thereby detecting the dimerization of binding partners.

In certain embodiments, there is provided: a reaction mixture for detecting dimerization of binding partners comprising: first binding partner/N-terminal portions of a split Cas enzyme and a second binding partner/C-terminal portion of the split Cas enzyme, wherein the split Cas enzyme when reconstituted with the N-terminal and C-terminal portions is capable of exhibiting trans-cleavage nuclease activity; first guide nucleic acids; RNP1 activating nucleic acids, wherein the RNP1 activating nucleic acids comprise a sequence complementary to the first guide nucleic acids, and wherein binding of an RNP1 complex formed by reconstituting the split Cas enzyme and the first guide nucleic acid to the RNP1 activating nucleic acid activates trans-cleavage activity of the split Cas enzyme; RNP2s, wherein the RNP2s comprise a second guide nucleic acid and an intact second Cas enzyme comprising trans-cleavage nuclease activity and wherein the second intact Cas enzyme is a different Cas enzyme than the split Cas enzyme; a plurality of template molecules comprising sequence homology to the second guide nucleic acid; a plurality of blocked primer molecules comprising a sequence complementary to the template molecules, wherein the blocked primer molecules cannot be extended by a polymerase; and a polymerase and a plurality of nucleotides.

In certain embodiments, there is provided: a method for identifying a dimerization of binding partners comprising the steps of: providing a reaction mixture comprising: first binding partner/N-terminal portions of a split Cas enzyme, wherein the split Cas enzyme when reconstituted with the N-terminal portion and a C-terminal portion comprises trans-cleavage nuclease activity; first guide nucleic acids; RNP1 activating nucleic acids, wherein the RNP1 activating nucleic acids comprise a sequence complementary to the first guide nucleic acids, and wherein binding of an RNP1 complex formed by reconstituting the split Cas enzyme and the first guide nucleic acid to the RNP1 activating nucleic acid activates trans-cleavage activity of the split Cas enzyme; second nucleic acid-guided nucleases, wherein the second nucleic acid-guided nuclease exhibits trans-cleavage activity; RNP2 activating nucleic acids; and a plurality of blocked guide molecules comprising a sequence complementary to the RNP2 activating nucleic acids; contacting the reaction mixture with a sample comprising a library of putative second binding partner/C-terminal portions of the split Cas enzyme under conditions that allow putative second binding partners to bind to the first binding partner of the first binding partner/N-terminal portion of the split Cas enzyme, and wherein if one of the putative second binding partners in the library of putative second binding partners binds to the first binding partner the split Cas enzyme is reconstituted and forms RNP1s with the first guide nucleic acids and RNP1 activating nucleic acids thereby initiating trans-cleavage of at least one of the blocked guide molecules and thereby producing at least one unblocked guide molecule, and wherein the at least one unblocked guide molecule forms an RNP2 with the second nucleic acid-guided nuclease, the RNP2 binds to RNP2 activating nucleic acids and becomes active thereby trans-cleaving at least one more of the blocked guide molecules in a cascade; allowing the cascade to continue; and detecting the at least one unblocked guide molecule, thereby detecting the dimerization of binding partners.

In certain embodiments, there is provided: a reaction mixture for detecting dimerization events comprising: first binding partner/N-terminal portions of a split Cas enzyme, wherein the split Cas enzyme when reconstituted with the N-terminal and a C-terminal portion comprises trans-cleavage nuclease activity; first guide nucleic acids; RNP1 activating nucleic acids, wherein the RNP1 activating nucleic acids comprise a sequence complementary to the first guide nucleic acids, and wherein binding of an RNP1 complex formed by reconstituting the split Cas enzyme and the first guide nucleic acid to the RNP1 activating nucleic acid activates trans-cleavage activity of the split Cas enzyme; second nucleic acid-guided nucleases, wherein the second nucleic acid-guided nuclease exhibits trans-cleavage activity; RNP2 activating nucleic acids; and a plurality of blocked guide molecules comprising a sequence complementary to the RNP2 activating nucleic acids.

In certain embodiments of the methods and/or reaction mixtures described herein, one or both of RNP1 and RNP2 comprises a nucleic acid-guided nuclease selected from Cas3, Cas12a, Cas12b, Cas12c, Cas12d, Cas12e, Cas14, Cas12h, Cas12i, Cas12j, Cas13a, or Cas13b.

In certain embodiments of the methods and/or reaction mixtures described herein, one or both of RNP1 and RNP2 comprises a nucleic acid-guided nuclease that is a Type V nucleic acid-guided nuclease or a Type VI nucleic acid-guided nuclease.

In certain embodiments of the methods and/or reaction mixtures described herein, one or both of RNP1 and RNP2 comprises a nucleic acid-guided nuclease comprising a RuvC nuclease domain or a RuvC-like nuclease domain but lacks an HNH nuclease domain.

In certain embodiments of the methods and/or reaction mixtures described herein, the reaction mixture further comprises reporter moieties, wherein the reporter moieties produce a detectable signal upon trans-cleavage activity by the RNP1 and/or RNP2 to identify a presence of one or more non-nucleic acid targets of interest in the sample.

In certain embodiments of the methods and/or reaction mixtures described herein, the first binding partner is an antigen and the second binding partner is a library of antibodies, or the first binding partner is a library of antibodies and the second binding partner is an antigen.

In certain embodiments of the methods and/or reaction mixtures described herein, the reaction mixture further comprises a molecular glue candidate, and wherein the first binding partner is an effector and the second binding partner is a target or the first binding partner is a target and the second binding partner is an effector.

In certain embodiments of the methods and/or reaction mixtures described herein, the first binding partner is a non-nucleic acid target and the second binding partner is a library of aptamers, or wherein the first binding partner is a library of aptamers and the second binding partner is a non-nucleic acid target.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which.

It should be understood that the drawings are not necessarily to scale, and that like reference numbers refer to like features.

Definitions

Figure 1:
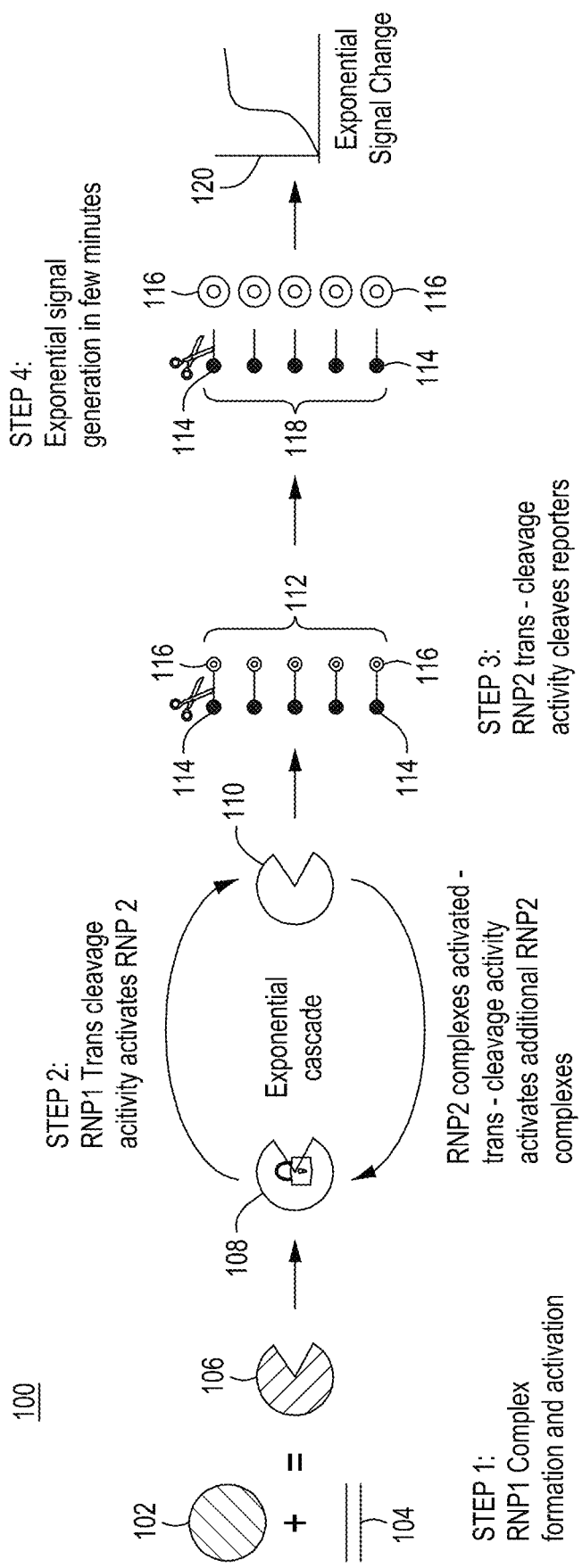
FIG. 1 shows a schematic overview of the general principles underlying the cascade assay on which the present dimerization screening assay is based, according to certain embodiments.

All of the functionalities described in connection with one embodiment of the compositions and/or methods described herein are intended to be applicable to the additional embodiments of the compositions and/or methods except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

Note that as used herein and in the appended claims, the singular forms "a," "an," and "the" include plural referents unless the context clearly dictates otherwise. Thus, for example, reference to "a cell" refers to one or more cells, and reference to "a system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention. Conventional methods are used for the procedures described herein, such as those provided in the art, and demonstrated in the Examples and various general references. Unless otherwise stated, nucleic acid sequences described herein are given, when read from left to right, in the 5' to 3' direction. Nucleic acid sequences may be provided as DNA, as RNA, or a combination of DNA and RNA (e.g., a chimeric nucleic acid).

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

The term "and/or" where used herein is to be taken as specific disclosure of each of the multiple specified features or components with or without another. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

As used herein, the term "about," as applied to one or more values of interest, refers to a value that falls within 10%, 9%, 8%, 7%, 6%, 5%, 4%, 3%, 2%, 1%, or less in either direction (greater than or less than) of a stated reference value, unless otherwise stated or otherwise evident from the context (except where such number would exceed 100% of a possible value).

As used herein, the term "activating nucleic acid" generally refers to all of RNP1 activating nucleic acids, RNP2 activating nucleic acids, and synthesized activating nucleic acids. "RNP1 activating nucleic acids" and "RNP2 activating nucleic acids" refer to nucleic acid molecules that complex with RNP1 and RNP2, respectively, and activate cis—and trans-cleavage of RNP1 and RNP2. "Synthesized activating nucleic acid" refers to the nucleic acid molecules that complex with RNP2 and activate cis- and trans-cleavage of RNP2 in the blocked primer molecule embodiment of the dimerization screening assay.

As used herein, the terms "binding affinity" or "dissociation constant" or "$K_d$" refer to the tendency of a molecule to bind (covalently or non-covalently) to a different molecule. A high $K_d$ (which in the context of the present disclosure refers to blocked nucleic acid molecules binding to RNP2; blocked primer molecules binding to template molecules; or blocked guide nucleic acids binding to RNP2 activating nucleic acids) indicates the presence of more unbound molecules, and a low $K_d$ (which in the context of the present disclosure refers to unblocked nucleic acid molecules binding to RNP2; unblocked primer molecules binding to template molecules; or unblocked guide nucleic acids binding to RNP2 activating nucleic acids) indicates the presence of more bound molecules. In the context of the present disclosure and the binding of blocked or unblocked nucleic acid molecules; blocked or unblocked primer molecules; or blocked or unblocked guide molecules, low $K_d$ values are in a range from about 100 fM to about 1 aM or lower (e.g., 100 zM) and high $K_d$ values are in the range of 100 nM-100 μM (10 mM) and thus are about $10^5$-to $10^{10}$-fold or higher as compared to low $K_d$ values.

As used herein, the terms "binding domain" or "binding site" refer to a region on a protein, DNA, or RNA, to which specific molecules and/or ions (ligands) may form a covalent or non-covalent bond. By way of example, a polynucleotide sequence present on a nucleic acid molecule (e.g., a primer binding domain) may serve as a binding domain for a different nucleic acid molecule (e.g., an unblocked primer nucleic acid molecule). Characteristics of binding sites are chemical specificity, a measure of the types of ligands that will bond, and affinity, which is a measure of the strength of the chemical bond.

As used herein, the terms "blocked guide molecule", "blocked guide nucleic acid", "blocked guide RNA" and "blocked gRNA" refer to CRISPR guide nucleic acids that cannot bind to the first or second RNP complex to activate cis- or trans-cleavage. The terms "unblocked guide molecule", "unblocked guide nucleic acid", "unblocked guide RNA" and "unblocked gRNA" refer to a formerly blocked gRNA that can bind to the second RNP complex (RNP1 or RNP2) to activate trans-cleavage of additional blocked gRNAs.

As used herein, the term "blocked nucleic acid molecule" refers to nucleic acid molecules that cannot bind to the first or second RNP complex to activate cis- or trans-cleavage. "Unblocked nucleic acid molecule" refers to a formerly blocked nucleic acid molecule that can bind to the first or second RNP complex (RNP1 or RNP2) to activate trans-cleavage of additional blocked nucleic acid molecules. A "blocked nucleic acid molecule" may be a "blocked primer molecule" in some embodiments of the dimerization screening assay. In the case of blocked primer molecules, "unblocked primer molecules" initiate synthesis of synthesized activating nucleic acids that can bind to RNP2 to activate trans-cleavage of additional blocked primer molecules.

The terms "Cas RNA-guided nuclease" or "CRISPR nuclease" or "nucleic acid-guided nuclease" or "Cas enzyme" refer to a CRISPR-associated protein that is an RNA-guided nucleic acid-guided nuclease suitable for assembly with a sequence-specific gRNA to form a ribonucleoprotein (RNP) complex.

As used herein, the terms "cis-cleavage", "cis-nucleic acid-guided nuclease activity", "cis-mediated nucleic acid-guided nuclease activity", "cis-nuclease activity", "cis-mediated nuclease activity", and variations thereof refer to sequence-specific cleavage of a target nucleic acid of interest, including an unblocked nucleic acid molecule or synthesized activating molecule, by a nucleic acid-guided nuclease in an RNP complex. Cis-cleavage is a single turn-over cleavage event in that only one substrate molecule is cleaved per event.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10, or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-ATCGAT-5' is 100% complementary to a region of the nucleotide sequence 5'-GCTAGCTAG-3'.

As used herein, the term "contacting" refers to placement of two moieties in direct physical association, including in solid or liquid form. Contacting can occur in vitro with isolated cells (for example in a tissue culture dish or other vessel) or in samples or in vivo by administering an agent to a subject.

A "control" is a reference standard of a known value or range of values.

As used herein, a "dimerizer" is one component or binding partner of a dimeric molecular interaction. In the context of the present dimerization screening assays, two "dimerizers" (i.e., a molecular binding pair), when interacting, reconstitute nuclease activity of a split Cas enzyme. There are two dimerizers in each reaction mix, a dimerizer/N-terminal portion of the split Cas enzyme ("di-N-term") and a dimerizer/C-terminal portion of the split Cas enzyme ("di-C-term"). "Dimerization moieties" include antibody and antigen pairs, small molecule/biological targets, bifunctional small molecules that join two or more molecules together, DNA molecules that can be bound by proteins, nucleic acid molecules that bind non-nucleic acid molecules (i.e., aptamers), RNA molecules that can be bound by an RNA-binding protein, or potential members of virtually any biomolecular interaction.

As used herein, "epitope" is the part of a macromolecule that is recognized by the immune system, specifically by antibodies, B cells, or T cells.

The terms "guide nucleic acid" or "guide RNA" or "gRNA" refer to a polynucleotide comprising 1) a crRNA region or guide sequence capable of hybridizing to the target strand of a target nucleic acid of interest, and 2) a scaffold sequence capable of interacting or complexing with a nucleic acid-guided nuclease. The crRNA region of the gRNA is a customizable component that enables specificity in every nucleic acid-guided nuclease reaction. A gRNA can include any polynucleotide sequence having sufficient complementarity with a target nucleic acid of interest to hybridize with the target nucleic acid of interest and to direct sequence-specific binding of a ribonucleoprotein (RNP) complex containing the gRNA and nucleic acid-guided nuclease to the target nucleic acid. Target nucleic acids of interest may include a protospacer adjacent motif (PAM), and, following gRNA binding, the nucleic acid-guided nuclease induces a double-stranded break either inside or outside the protospacer region on the target nucleic acid of interest, including on an unblocked nucleic acid molecule or synthesized activating molecule. A gRNA may contain a spacer sequence including a plurality of bases complementary to a protospacer sequence in the target nucleic acid. For example, a spacer can contain about 2, 3, 4, 5, 6, 7, 8, 9, 10, 11, 12, 13, 14, 15, 20, 25, 30, 35, 40, 45, 50, 55, 60, or more bases. The gRNA spacer may be 50%, 60%, 75%, 80%, 85%, 90%, 95%, 97.5%, 98%, 99%, or more complementary to its corresponding target nucleic acid of interest. Optimal alignment may be determined with the use of any suitable algorithm for aligning sequences. A guide RNA may be from about 20 nucleotides to about 300 nucleotides long. Guide RNAs may be produced synthetically or generated from a DNA template.

A "ligand" is a substance that is able to bind to and form a complex with a biomolecule to serve a biological purpose.

"Modified" refers to a changed state or structure of a molecule. Molecules may be modified in many ways including chemically, structurally, and functionally. In one embodiment, a nucleic acid molecule (for example, a blocked nucleic acid molecule) may be modified by the introduction of non-natural nucleosides, nucleotides, and/or internucleoside linkages. In another embodiment, a modified protein (e.g., a modified or variant nucleic acid-guided nuclease) may refer to any polypeptide sequence alteration which is different from the wildtype.

The terms "percent sequence identity", "percent identity", or "sequence identity" refer to percent (%) sequence identity with respect to a reference polynucleotide or polypeptide sequence following alignment by standard techniques. Alignment for purposes of determining percent sequence identity can be achieved in various ways that are within the capabilities of one of skill in the art, for example, using publicly available computer software such as BLAST, BLAST-2, PSI-BLAST, or Megalign software. In some embodiments, the software is MUSCLE (Edgar, Nucleic Acids Res., 32(5):1792-1797 (2004)). Those skilled in the art can determine appropriate parameters for aligning sequences, including any algorithms needed to achieve maximal alignment over the full length of the sequences being compared. For example, in embodiments, percent sequence identity values are generated using the sequence comparison computer program BLAST (Altschul, et al., J. Mol. Biol., 215:403-410 (1990)).

As used herein, the terms "preassembled ribonucleoprotein complex", "ribonucleoprotein complex", "RNP complex", or "RNP" refer to a complex containing a guide RNA (gRNA) and a nucleic acid-guided nuclease, where the gRNA is integrated with the nucleic acid-guided nuclease. The gRNA, which includes a sequence complementary to a target nucleic acid, guides the RNP to the target nucleic acid and hybridizes to it. The hybridized target nucleic acid-gRNA units are cleaved by the nucleic acid-guided nuclease.

As used herein, the terms "protein" and "polypeptide" are used interchangeably. Proteins may or may not be made up entirely of amino acids.

As used herein, the term "protein complex" is used to refer to a group of two or more constituent proteins formed by protein-protein interactions that may or may not involve formation of covalent bonds.

As used herein, the term "sample" may refer to specimen or aliquots from: food; agricultural products; pharmaceuticals; cosmetics; nutraceuticals; personal care products; environmental substances such as soil, water, air, or sewer samples; industrial sites and products; and chemicals and compounds. A "sample" may also refer to: tissues; cells or component parts thereof; body fluids, including but not limited to peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus activities, bronchopulmonary aspirates, blastocyl cavity fluid, and umbilical cord blood. A "sample" may further include a homogenate, lysate, or extract. A "sample" may further refer to a medium, such as a nutrient broth or gel, which may contain cellular components, such as proteins or nucleic acid molecules.

As used herein, the term "split Cas enzyme" or "split nucleic acid-guided nuclease" refer to a CRISPR/cas nuclease that has been split into N-terminal and C-terminal portions at a point where there is no spontaneous association between the N-terminal and C-terminal portions of the nuclease in the absence of a dimerization event; however, the split must allow association of the N-terminal and C-terminal portions of the nuclease—and reconstitution of nuclease activity—in the presence of a dimerization event.

As used herein, the terms "trans-cleavage", "trans-nucleic acid-guided nuclease activity", "trans-mediated nucleic acid-guided nuclease activity", "trans-nuclease activity", "trans-mediated nuclease activity" and variations thereof refer to indiscriminate, non-sequence-specific cleavage of a nucleic acid molecule by a nucleic acid-guided nuclease (such as by a Cas12, Cas13, and Cas14) which is triggered by binding of the target nucleic acid of interest (or unblocked nucleic acid molecule or synthesized activating molecule or RNP2 activating molecule). Trans-cleavage is a "multiple turn-over" event, in that more than one substrate molecule is cleaved after initiation by a single turn-over cis-cleavage event.

Type V CRISPR/Cas nucleic acid-guided nucleases are a subtype of Class 2 CRISPR/Cas nucleases such as, but not limited to, engineered Cas12a, Cas12b, Cas12c, C2c4, C2c8, C2c5, C2c10, C2c9, CasX (Cas12e), CasY (Cas12d), Cas 13a nucleases or naturally-occurring proteins, such as a Cas12a isolated from, for example, *Francisella tularensis* subsp. *Novicida* (Gene ID: 60806594), Candidatus Methanoplasma *termitum* (Gene ID: 24818655), Candidatus Methanomethylophilus alvus (Gene ID: 15139718), and [*Eubacterium*] eligens ATCC 27750 (Gene ID: 41356122), and an artificial polypeptide, such as a chimeric protein.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like.

DETAILED DESCRIPTION

The present disclosure provides compositions of matter and methods for dimerization screening assays that detect dimerization events between dimerizers, or binding pairs. The dimerization screening assays allow for the screening of massive numbers of binding pairs, and provide for high accuracy, low cost, and minimum workflow, particularly when performed with microfluidic instrumentation. The "dimerization screening assays" described herein comprise a split Cas enzyme that, when reconstituted, is functional and able to form a ribonucleoprotein complex, and, once the ribonucleoprotein complex is formed, exhibits both cis- and trans-cleavage activity. At least three embodiments of the dimerization screening assays are described. Two of the embodiments utilize blocked nucleic acid molecules (with one embodiment configuring the blocked nucleic acid molecule as a blocked primer molecule) that cannot activate a ribonucleoprotein complex until the blocked nucleic acid molecules are unblocked, and the third embodiment utilizes a blocked guide nucleic acid (i.e., blocked guide RNA) that cannot form an activated ribonucleoprotein complex until the blocked guide nucleic acid is unblocked. All embodiments provide a dimerization screening assay that is robust, easily multiplexed and easily reprogrammable by reconfiguring the dimerizer/split Cas enzyme fusion as described in detail below.

The first two embodiments provide a reaction mix comprising: a dimerizer/N-terminal portion of the split Cas enzyme that exhibits both cis- and trans-cleavage activity, a dimerizer/C-terminal portion of the split Cas enzyme, and a first gRNA which potentially will form a first ribonucleoprotein complex (RNP1) with a reconstituted split Cas enzyme; a second ribonucleoprotein complex (RNP2) comprising an intact Cas enzyme that also exhibits both cis- and trans-cleavage activity, and a second gRNA; RNP1 activating nucleic acids; either blocked nucleic acid molecules or blocked primer molecules, depending on the type of dimerization screening assay, for RNP2; and reporter moieties, which may be separate molecules from the blocked nucleic acid molecules, or the reporter moieties may be incorporated into and part of the blocked nucleic acid molecules. The split Cas enzyme is not activated and is unable to form RNP1 unless and until the N-terminal and C-terminal portions of the split Cas enzyme are brought into functional proximity by a dimerization event between dimerizers and the nuclease activity (both cis- and trans-cleavage activity) of the split Cas enzyme is reconstituted.

The third embodiment provides a reaction mix comprising: a dimerizer/N-terminal portion of the split Cas enzyme that exhibits both cis- and trans-cleavage activity, a dimerizer/C-terminal portion of the split Cas enzyme, and a first gRNA which potentially will form a first ribonucleoprotein complex (RNP1) with a reconstituted split Cas enzyme; an intact Cas enzyme that also exhibits both cis- and trans-cleavage activity; blocked guide nucleic acids that, when unblocked, can form a second ribonucleoprotein complexes (RNP2s) with the intact Cas enzyme; RNP1 activating nucleic acids and RNP2 activating nucleic acids; and reporter moieties. Like the first two embodiments, in this embodiment, the split Cas enzyme is not activated and is unable to form RNP1 unless and until the N-terminal and C-terminal portions of the split Cas enzyme are brought into functional proximity by a dimerization event and the nuclease activity (both cis- and trans-cleavage activity) of the split Cas enzyme is reconstituted.

The present dimerization screening assays can detect putative binding pairs of interest (e.g., DNA, RNA and/or cDNA) at attomolar (aM) (or lower) limits. Importantly, the screening assays prevent non-specific signal generation resulting in false positives by blocking components of RNP2 or, in the case of blocked primer molecules the synthesized activating nucleic acids, such that the second ribonucleoprotein complex (RNP2) is not activated until the components are unblocked. Once RNP2 is activated, the reporter moieties are activated in a cascade, resulting in signal generation indicating a dimerization event. A particularly advantageous feature of the dimerization screening assay is that, with the exception of the putative dimerizers that are fused to the N-terminal and C-terminal portions of the split Cas enzyme, the dimerization screening assay components can be the same in each assay no matter what putative binding pairs of interest (i.e., dimerizers) are being detected.

FIG. 1 provides a simplified diagram demonstrating a method 100 of a cascade assay upon which the dimerization screening assays of the present disclosure are built, according to certain embodiments. (See, USSNs 17/861,207 and 17/861,209, both filed 9 Jul. 2022; and USPNs 11,693,520 and 11,702,686.) The cascade assay is initiated when a target nucleic acid of interest 104 (e.g., a nucleic acid from a pathogen) binds to and activates a first pre-assembled ribonucleoprotein complex (RNP1) 102, thus forming activated first ribonucleoprotein complex (RNP1) 106. The ribonucleoprotein complex comprises a guide RNA (gRNA) and a nucleic acid-guided nuclease, where the gRNA is integrated with (i.e., non-covalently coupled with) the nucleic acid-guided nuclease. The gRNA, which includes a sequence complementary to the target nucleic acid of interest, guides the RNP complex to the target nucleic acid of interest and hybridizes to it. Typically, preassembled RNP complexes are employed in a reaction mix—as opposed to separate, unassembled nucleic acid-guided nucleases and gRNAs— to facilitate rapid detection of the target nucleic acid(s) of interest; however, the reaction mix may comprise separate first nucleic acid nucleases and gRNAs.

"Activation" of RNP1 refers to activating trans-cleavage activity of the nucleic acid-guided nuclease in RNP1 106 by first initiating cis-cleavage where the target nucleic acid of interest is cleaved by the nucleic acid-guided nuclease. In addition to cis-cleavage activity, trans-cleavage activity (i.e., multi-turnover activity) of the nucleic acid-guided nuclease is also initiated, where trans-cleavage is indiscriminate, leading to non-sequence-specific cutting of nucleic acid molecules by the nucleic acid-guided nuclease of RNP1 106.

The trans-cleavage activity of RNP1 106 further triggers activation of one or more second ribonucleoprotein complexes (RNP2s) 108 in various ways, which are described in detail below, thus forming activated second ribonucleoprotein complexes (RNP2s) 110. Each newly activated RNP2 110 activates more RNP2s 108→110, which in turn cleave reporter moieties 112 to form cleaved report moieties 118. The reporter moieties 112 may comprise, for example, a synthetic molecule linked or conjugated to a quencher 114 and a fluorophore 116 such as, for example, a probe with a dye label (e.g., FAM or FITC) on the 5' end and a quencher on the 3' end. The quencher 114 and fluorophore 116 can be about 20-30 bases apart (or approximately 10-11 nm apart), or less, for effective quenching via fluorescence resonance energy transfer (FRET). Reporter moieties also are described in greater detail below.

As more RNP2s are activated 108→110, more trans-cleavage activity is activated and more reporter moieties are unquenched; thus, the binding of the target nucleic acid of interest 104 to RNP1 102 initiates what becomes a cascade of signal production 120, which increases exponentially. The cascade assay thus comprises a single turnover event that triggers a multi-turnover event that then triggers more multi-turnover events in a "cascade." As described below in relation to FIG. 6, the reporter moieties 112 may be provided as molecules that are separate from the other components of the nucleic acid-guided nuclease cascade assay, or the reporter moieties may be covalently or non-covalently linked to the blocked nucleic acid molecules or blocked primer molecules.

Figure 2A:
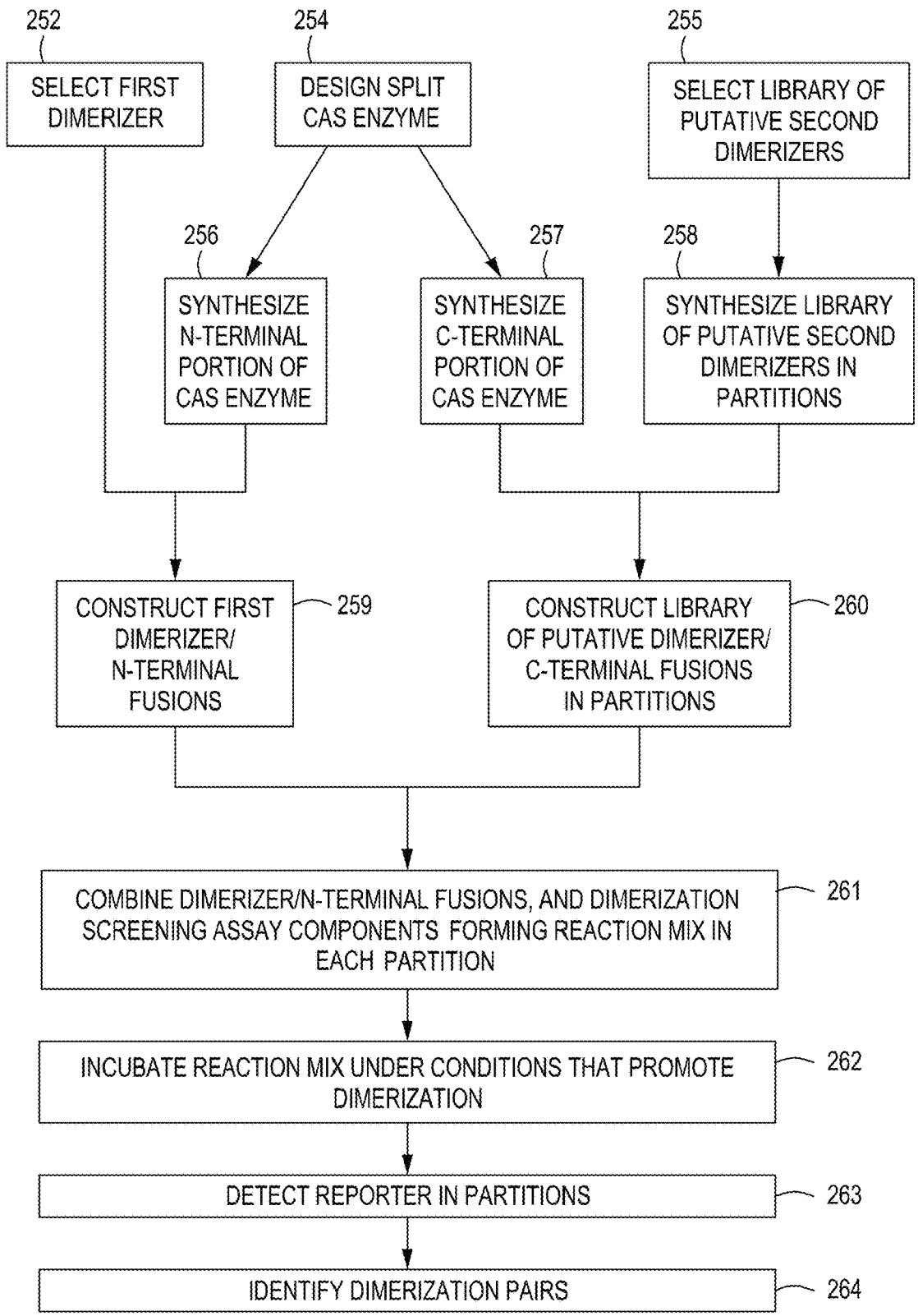
FIG. 2A is a simplified flow chart of an exemplary method for performing the dimerization screening assays described herein, according to certain embodiments.

FIG. 2A is a simplified flow chart of an exemplary method 250 for performing the dimerization screening assays described herein. Each of the steps described here will be discussed in more detail below. Dimerization screening assay 250 begins with selecting a first dimerizer 252 to use to screen for a binding partner. The first dimerizer is a molecular moiety for which one wishes to identify a binding partner from a library of putative second dimerizers; that is, the putative second dimerizers are molecular moieties that potentially dimerize with the first dimerizer. In one example, the first dimerizer may include an antigen against which an antibody is desired. In yet another example, the first dimerizer may include a non-nucleic acid target of interest against which an aptamer is desired.

In a separate step 254 and optionally in parallel, a split Cas enzyme is designed. In the present methods, any Cas enzyme may be employed as long as it is appropriate for the RNP1 activating nucleic acid used in the dimerization screening assay. For example, a DNA nucleic acid-guided nuclease (e.g., a Cas12a, Cas14a, or Cas3) should be utilized if the RNP1 activating nucleic acid is a DNA molecule, and an RNA nucleic acid-guided nuclease (e.g., Cas13a or Cas12g) should be utilized if the RNP1 activating nucleic acid is an RNA molecule. In addition, the Cas enzymes utilized in the dimerization screening assay must exhibit trans-cleavage activity as described below. The split between the N-terminal and C-terminal portions of the Cas enzyme should be made such that a reconstituted enzyme (with trans-cleavage activity) is produced once the N-terminal and C-terminal portions are in functional proximity with one another. The Cas enzyme is split into N-terminal and C-terminal portions at a point where there is no spontaneous association between the N-terminal and C-terminal portions of the Cas enzyme in the absence of two dimerizing dimerizers; however, the split must allow association of the N-terminal and C-terminal portions of the Cas enzyme— and reconstitution of nuclease activity— when the dimerizers are associated with one another. Once the appropriate split has been determined, the N-terminal and C-terminal portions of the split Cas enzyme are synthesized 256, 257.

In yet another step and optionally in parallel, a library of putative second dimerizers is selected 255. The library of putative second dimerizers is essentially a group of molecules that may dimerize with the first dimerizer. For example, the library of putative second dimerizers may include antibodies that have been generated in response to an antigen. The dimerization screening assay as described below is amenable to massive multiplexing such that tens, hundreds, thousands, tens of thousands or more putative second dimerizers may be screened in a single dimerization screening assay. Once a library of putative second dimerizers is selected, the individual members of the library are synthesized in partitions 258.

At step 259, the first dimerizer/N-terminal fusion molecule is constructed. The first dimerizer/N-terminal fusion molecule is constructed such that the N-terminal portion of the split Cas enzyme can associate with the C-terminal portion of the split Cas enzyme to reconstitute nuclease activity, and such that the first dimerizer is available to dimerize with a putative second dimerizer from the library. To allow for the needed association and dimerization, linkers are typically used to link the first dimerizer to the N-terminal portion of the split Cas enzyme. Linkers are important in the construction of stable, functional fusion molecules as linkers provide "distance" between fused molecules thereby avoiding hindrance of dimerization events and reconstitution of enzyme activity. The separation distance between functional units of the molecules—in this case, the N- or C-terminal portions of the split Cas enzyme and the first or putative dimerizer—can impact, e.g., ligand access and the ability to bind to a substrate; thus, a variety of linkers with different lengths and degrees of rigidity may be used and can be determined empirically.

Similar to step 259, in step 260, a library of putative second dimerizer/C-terminal fusion molecules are constructed, each in a separate partition. The putative second dimerizer/C-terminal fusion molecule also is constructed such that the C-terminal portion of the split Cas enzyme can associate with the N-terminal portion of the split Cas enzyme to reconstitute nuclease activity, and such that the putative second dimerizer is available to dimerize with the first dimerizer. Also— as described above— to allow for the needed association and dimerization, linkers are typically used to link the second dimerizer to the C-terminal portion of the split Cas enzyme. Note that in this example, the first dimerizer is fused to the N-terminal portion of the split Cas enzyme and the library of putative second dimerizers are fused to the C-terminal portion of the split Cas enzyme; however, it should be clear to those of ordinary skill in the art given the present disclosure that the first dimerizer instead could be fused to the C-terminal portion of the split Cas enzyme and the library of putative second dimerizers could be fused to the N-terminal portion of the split Cas enzyme.

Once the first dimerizer/N-terminal fusion molecules and putative second dimerizer/C-terminal fusion molecules are constructed, at step 261, first dimerizer/N-terminal fusion molecules are added to each partition containing a putative second dimerizer/C-terminal fusion molecule, and then dimerization screening assay components (described in detail below) are added to each partition such that each partition contains a reaction mix. The dimerization screening assay components in the reaction mix will differ somewhat depending on the embodiment (i.e., first, second or third embodiment) of the dimerization screening assay employed, as described briefly above and in detail below.

At step 262, the reaction mixes are incubated under conditions that promote dimerization between the first dimerizer and a putative second dimerizer, allowing for association of the N-terminal and C-terminal portions of the split Cas enzyme, and thereby reconstituting the nuclease activity (i.e., the cis- and trans-cleavage activity) of the split Cas enzyme. Once the dimerization screening assay reaction has taken place, the reporter moiety (as described below) can be detected 263, and dimerization pairs (i.e., binding between the first dimerizer and a putative second dimerizer) are identified 264.

Figure 2B:
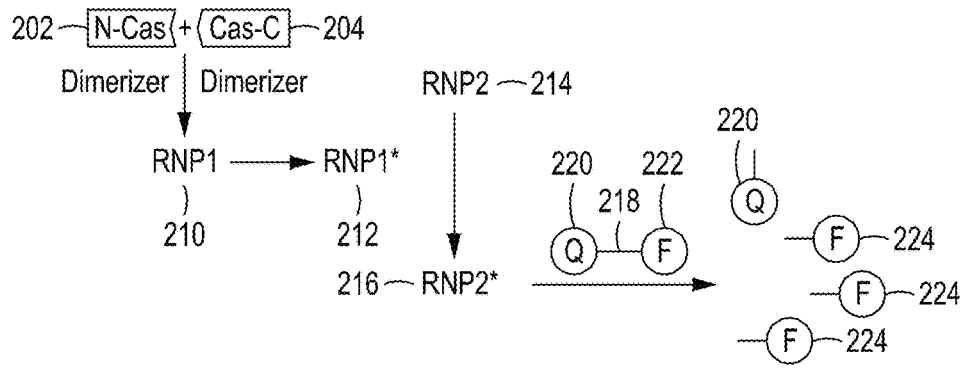
FIG. 2B shows a simple schematic overview of the principle behind the dimerization screening assay described herein, according to certain embodiments.

FIG. 2B shows a simple schematic overview of the principle behind the dimerization screening assay described herein. In method 200, N-terminal 202 and C-terminal 204 portions of a split Cas enzyme are present (in the current embodiment, RNP1 is not preassembled, as described in more detail below). In the presence of two dimerizers—one on each of the N-terminal 202 and C-terminal 204 portions—and a dimerizing event, RNP1 210 is formed and becomes an activated RNP1*212. Activation of RNP1 (210→212) triggers unblocking of, in the various embodiments, a blocked nucleic acid molecule, a blocked primer molecule, or a blocked guide nucleic acid molecule, which in turn complexes with (or, in the context of blocked primer molecules, produces synthesized activating nucleic acids that complex with) RNP2 214 and activates RNP2*216. Activation of RNP2 (214→216) triggers trans-cleavage activity of reporter moieties 218 present in the reaction mix. Reporter moieties 218 comprise a quencher 220 and a quenched fluorophore 222. However, once the reporter moieties are cleaved, the quencher 220 and quenched fluorophore 222 are no longer in proximity and the formerly quenched fluorophore is now a fluorophore 224 that can generate a fluorescent signal. In this example, the dimerization screening assay screens for dimerization events between two molecules (i.e., dimerizers).

Figure 2C:
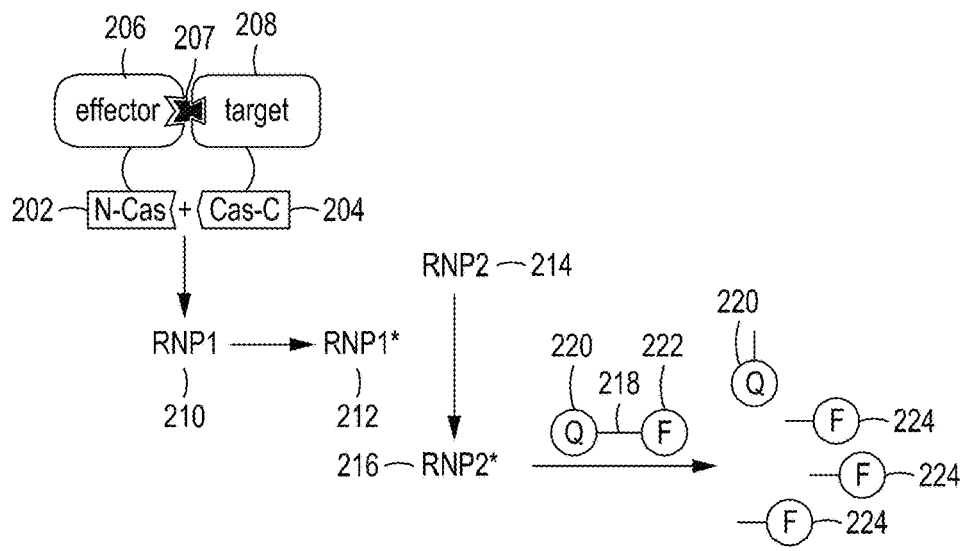
FIG. 2C shows a simple schematic overview of the dimerization screening assay applied to screening for molecular glue (i.e., bifunctional small molecule) candidates, according to certain embodiments.

FIG. 2C shows a simple schematic overview of the dimerization screening assay applied to screening for molecular glue (i.e., bifunctional small molecule) candidates, which can bring two or more molecules into functional proximity (see, e.g., Gerry and Schreiber, Nat. Chem. Biol., 16(4):369-78 (2020)). In this embodiment, the two molecules 206, 208 are dimerizers, but only when joined by molecular glue 207. In method 230, N-terminal 202 portion of a split Cas enzyme is linked to an effector 206 (i.e., a first dimerizer) and C-terminal portion 204 of a split Cas enzyme is linked to a target 208 (i.e., a second dimerizer). However, effector 206 and target 208 do not dimerize unless molecular glue 207 is present. In the presence of two dimerizers 206, 208— one on each of the N-terminal 202 and C-terminal 204 portions and joined by molecule glue 207—and a dimerizing event, RNP1 210 is formed becomes an activated RNP1*212. Activation of RNP1 (210→212) triggers unblocking of, in the various embodiments, a blocked nucleic acid molecule, a blocked primer molecule, or a blocked guide nucleic acid molecule, which in turn complexes with (or in the case of blocked primer molecules, produces synthesized activating nucleic acids that complex with) RNP2 214 and activates RNP2*216.

Activation of RNP2 (214→216) triggers trans-cleavage activity of reporter moieties 218 present in the reaction mix. Reporter moieties 218 comprise a quencher 220 and a quenched fluorophore 222. However, once the reporter moieties are cleaved, the quencher 220 and quenched fluorophore 222 are no longer in proximity and the formerly quenched fluorophore is now a fluorophore 224 that can generate a fluorescent signal. In this example, the dimerizing screening assay is actually screening for molecular glue molecules in a library of putative molecule glue molecules that bring the dimerizers (and therefore the N-terminal and C-terminal portions of the split Cas enzyme) together.

Figure 2D:
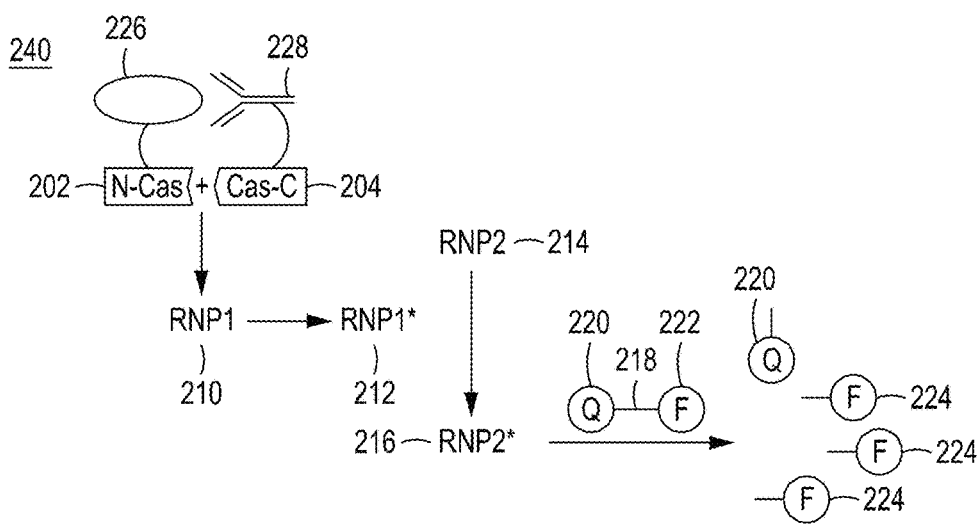
FIG. 2D shows a simple schematic overview of the dimerization screening assay applied to screening for antibody/antigen binding pairs, according to certain embodiments.

FIG. 2D shows a simple schematic overview of the dimerization screening assay applied to screening for antibodies. In this embodiment, an antigen or epitope 226 and an antibody 228 are the dimerizers. In method 240, N-terminal 202 portion of a split Cas enzyme is linked to antigen or epitope 226 (i.e., a first dimerizer) and C-terminal portion 204 of a split Cas enzyme is linked to an antibody 228 (i.e., a second dimerizer). In the presence of the two dimerizers 226 (antigen), 208 (antibody)—one on each of the N-terminal 202 and C-terminal 204 portions, respectively—and a dimerizing event, RNP1 210 is formed becomes an activated RNP1*212. Activation of RNP1 (210→212) triggers unblocking of, in the various embodiments, a blocked nucleic acid molecule, a blocked primer molecule, or a blocked guide nucleic acid molecule, which in turn complexes with (or produces synthesized activating nucleic acids that complex with) RNP2 214 and activates RNP2*216. Activation of RNP2 (214→216) triggers trans-cleavage activity of reporter moieties 218 present in the reaction mix. Reporter moieties 218 comprise a quencher 220 and a quenched fluorophore 222. However, once the reporter moieties are cleaved, the quencher 220 and quenched fluorophore 222 are no longer in proximity and the formerly quenched fluorophore is now a fluorophore 224 that can generate a fluorescent signal. In this example, the dimerizing screening assay is screening an antibody in a library of putative antibodies that binds to a particular antigen.

In addition to screening for molecular glue candidates or antibody/antigen pairs as described in relation to FIGS. 2C and 2D, it should be apparent to one of ordinary skill in the art given the present disclosure that the screening assays described herein can be used to find aptamers, e.g., for non-nucleic acid targets. Aptamers are short, single-stranded oligonucleotides (DNA or RNA or a chimera) that bind to non-nucleic acid targets of interest with high specificity and affinity by folding into a tertiary structure. Aptamers can be used like antibodies in, e.g., diagnostics, for cancer diagnosis and prognosis, and in monitoring environmental contamination. Although aptamers recognize and bind non-nucleic acid targets of interest like antibodies, aptamers have advantages over antibodies. For example, aptamers are more easily and cheaply manufactured than antibodies, withstand repeated rounds of denaturation and renaturation, are temperature resistant (e.g., stable at room temperature), have little batch to batch variation, and have a long shelf life. To date, selection of aptamers has typically been accomplished via SELEX (Systematic Evolution of Ligands by Exponential Enrichment), which takes only 2-8 weeks, whereas antibodies are produced in vivo via a laborious and expensive process that typically takes more than 6 months. Also, aptamers can be easily modified without affinity loss. The target potential for aptamers includes ions, small molecules, whole cells, and live animals. (See, e.g., Zhang, et al., Molecules, 24:941-63 (2019).) The present screening assay can be used as an alternative to SELEX.

In the context of the present screening assay, an aptamer library of approximately $10^5$-$10^7$ single-stranded DNA or RNA random oligonucleotides, 20-150 nucleotides in length, is synthesized. The aptamers typically comprise 5' and 3' fixed primer sequences and a random region in the middle of the oligonucleotide. The N-terminal portion of a split Cas enzyme is linked, e.g., to a non-nucleic acid target for which one wishes to identify an aptamer binding partner (i.e., the first dimerizer) and the C-terminal portion of the split Cas enzyme is linked the members of the aptamer library (i.e., the putative second dimerizers). In the presence of the two dimerizers, i.e., the non-nucleic acid target and cognate aptamer one on each of the N-terminal and C-terminal portions— and a dimerizing event, RNP1 is formed and becomes an activated RNP1. As described in detail below, activation of RNP1 triggers unblocking of, in the various embodiments, a blocked nucleic acid molecule, a blocked primer molecule, or a blocked guide nucleic acid molecule, which in turn complexes with (or produces synthesized activating nucleic acids that complex with) RNP2, where RNP2 is then activated. Activation of RNP2 triggers trans-cleavage activity of reporter moieties present in the reaction mix, where the reporter moieties comprise a quencher and a quenched fluorophore. Once the reporter moieties are cleaved, the quencher and quenched fluorophore are no longer in proximity and the formerly quenched fluorophore is now a fluorophore that can generate a fluorescent signal. In this example, the dimerizing screening assay is screening to identify non-nucleic acid target in a library of putative aptamers.

Various components of the dimerization screening assays herein, descriptions of how the dimerization screening assays work, and instrumentation for facilitating high throughput screening assays are described in detail below.

Assay Components

Nucleic Acid-Guided Nucleases

The dimerization screening assays comprise nucleic acid-guided nucleases in the reaction mix, either provided as a protein, a coding sequence for the protein (not preferred), or in a ribonucleoprotein (RNP) complex. Any nucleic acid-guided nuclease having both cis- and trans-cleavage activity may be employed; however, the same nucleic acid-guided nuclease may not be used for RNP1 and RNP2. Note that trans-cleavage activity is not triggered unless and until cis-cleavage activity (i.e., sequence specific activity) is initiated. Nucleic acid-guided nucleases include Type V and Type VI nucleic acid-guided nucleases, as well as nucleic acid-guided nucleases that comprise a RuvC nuclease domain or a RuvC-like nuclease domain but lack an HNH nuclease domain. Nucleic acid-guided nucleases with these properties are reviewed in Makarova and Koonin, Methods Mol. Biol., 1311:47-75 (2015) and Koonin, et al., Current Opinion in Microbiology, 37:67-78 (2020) and updated databases of nucleic acid-guided nucleases and nuclease systems that include newly-discovered systems include BioGRID ORCS (orcs:thebiogrid.org); GenomeCRISPR (genomecrispr.org); Plant Genome Editing Database (plantcrispr.org) and CRISPRCasFinder (crispercas.i2bc.paris-saclay.fr).

The type of nucleic acid-guided nuclease utilized in the method of detection depends on the type of activating nucleic acid (i.e., RNP1 and RNP2 activating nucleic acids) to be detected. For example, a DNA nucleic acid-guided nuclease (e.g., a Cas12a, Cas14a, or Cas3) should be utilized if the activating nucleic acid is a DNA molecule, and an RNA nucleic acid-guided nuclease (e.g., Cas13a or Cas12g) should be utilized if the activating nucleic acid is an RNA molecule. In many embodiments of the dimerization screening assays, the activating nucleic acids—both the RNP1 and the RNP2 activating nucleic acids—will be DNA molecules since DNA is less susceptible to degradation than RNA. Exemplary nucleic acid-guided nucleases include, but are not limited to, Cas RNA-guided DNA nucleic acid-guided nucleases, such as Cas3, Cas12a (e.g., AsCas12a, LbCas12a), Cas12b, Cas12c, Cas12d, Cas12e, Cas14, Cas12h, Cas12i, and Cas12j; Cas RNA-guided RNA nucleic acid-guided nucleases, such as Cas13a (LbaCas13, Lbu-Cas13, LwaCas13), Cas13b (e.g., CccaCas13b, PsmCas13b), and Cas12g; and any other nucleic acid (DNA, RNA, or cDNA) targeting nucleic acid-guided nuclease with cis-cleavage activity and collateral trans-cleavage activity. In some embodiments, the nucleic acid-guided nuclease is a Type V CRISPR-Cas nuclease, such as Cas12a, Cas13a, or Cas14a. In some embodiments, the nucleic acid-guided nuclease is a Type I CRISPR-Cas nuclease, such as Cas3. Type II and Type VI nucleic acid-guided nucleases may also be employed.

For the split Cas enzymes employed in the dimerization screening assays, the appropriate "split" between the N-terminal and C-terminal portions of the nuclease will depend on the Cas enzyme chosen and may be determined empirically for a desired nuclease as described below in Example II. (See Kempton, et al., Molec. Cell, 78:184-91 (2020) for a discussion of use of a split Cas12a system to construct molecular circuits.) The split between the N-terminal and C-terminal portions of the nuclease should be made such that a reconstituted nuclease is produced once the two portions are in proximity with one another, and at a point where there is no spontaneous association between the N-terminal and C-terminal portions of the nuclease in the absence of two dimerizing dimerizers. However, the split must allow association of the N-terminal and C-terminal portions of the nuclease—and reconstitution of nuclease activity—in the presence of the dimerizers. Once the proper split for the desired nuclease is determined, appropriate N-terminal and C-terminal split Cas enzyme constructs can be designed and synthesized.

Linkers

As mentioned above, the N-terminal and C-terminal portions of the split Cas enzyme are fused to the dimerizers (i.e., first and putative second dimerizers). The separation distance between functional units of the fused molecules—in this case, the N— or C-terminal portions of the split Cas enzyme and the first or putative second dimerizer—can impact the ability of the N-terminal and C-terminal portions of the split Cas enzyme to associate and/or the ability of the first dimerizer to bind with a putative second dimerizer; thus, the availability of a variety of linkers with different lengths and degrees of rigidity may be used and optimization to minimize steric hindrance may be determined empirically. A linker or linkage may be covalently linked to the two fused molecules and may be linear, branched, cyclic or a single atom. The linker may be a chain of between 1 and 20 atoms and in certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone.

The linker may include one or more substituent groups, for example with an alkyl, aryl or alkenyl group. A linker may include, without limitation, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. There are peptide and non-peptide linkers, and linkers are generally classified into three categories according to their structures. In addition to peptide linkers, there are PEG linkers, which are chemically functionalized polyethylene glycol (PEG) linkers and are attractive due to their aqueous solubility.

Again, of the various types of linkers, the linkers may be cleavable or non-cleavable. Any convenient cleavable groups may be utilized to provide for cleavage of the linker upon application of a suitable stimulus. Cleavable linkers include cleavable groups of interest, including but not limited the cleavable linkers (as described by Szychowski et al., J. Am. Chem. Soc., 132:18351 (2010)), Olejnik et al., Methods in Enzymology, 291:135-154 (1998), and further described in U.S. Pat. No. 6,027,890; Olejnik et al., PNAS, 92:7590-94 (1995); Ogata et al., Anal. Chem., 74:4702-4708 (2002); Bai et al., Nucl. Acids Res., 32:535-541 (2004); Zhao et al., Anal. Chem., 74:4259-4268 (2002); Sanford et al., Chem. Mater., 10:1510-20 (1998)), and linkers such as electrophilically cleavable linkers, nucleophilically cleavable linkers, photocleavable linkers, metal cleavable linkers, electrolytically-cleavable linkers, enzymatically cleavable linkers, linkers that are cleavable under reductive or oxidative conditions (e.g., a disulfide linker or a diazobenzene linker) and linkers that are cleavable using an acidic reagent (see e.g., Fauq et al., Bioconjugate Chem., 17:248-254 (2006)) or a basic reagent. In some embodiments, the cleavable linker includes a chemically cleavable group (e.g., a fluoride cleavable group), a photocleavable group or an enzymatically cleavable group.

Any convenient enzymatically cleavable groups may be utilized in the cleavable linkers. For example, the enzymatically cleavable group can include a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). Another example is a thrombin cleavage site, e.g., CGLVPAGSGP (SEQ ID NO: 1). Additional suitable linkers including protease cleavage sites include linkers including one or more of the following exemplary amino acid sequences: 1) SLLKSRMVPNFN (SEQ ID NO: 2) or SLLIARRMPNFN (SEQ ID NO: 3), cleaved by cathepsin B; SKLVQASASGVN (SEQ ID NO: 4) or SSYLKASDAPDN (SEQ ID NO: 5), cleaved by an Epstein-Barr virus protease.

Cleavable linkers useful for fusing the N-terminal and C-terminal portions of the split Cas enzyme to the first dimerizer or putative second dimerizer also include photosensitive groups comprising bonds that break upon exposure to light of a certain wavelength. Suitable photocleavable linkers for use in the subject cleavable probes include, but are not limited to, ortho-nitrobenzyl-based linkers, phenacyl linkers, alkoxybenzoin linkers, chromium arene complex linkers, NpSSMpact linkers and pivaloylglycol linkers (see Guillier et al., Chem. Rev., 1000:2091-2157 (2000)). Chemically cleavable groups include silane or —O—Si(R)$_2$—O—, where each R is independently selected from hydrogen, an aryl, a substituted aryl, an alkyl and a substituted alkyl, or a dialkoxydiarylsilane linker, such as a dialkoxydiphenylsilane (DADPS) linker.

Another example of linker technology of use in the present compounds and methods involves click chemistry. Click chemistry is a method for attaching a substrate of interest to a specific biomolecule, a process called bioconjugation, allowing the joining of substrates of choice with specific biomolecules. In some applications, click reactions join a biomolecule and a reporter molecule; however, in the present screening assay, click reactions are used to join a first and/or putative second dimerizer with either the N-terminus or C-terminus of the split nucleic acid-guided nuclease. Click reactions typically occur in "one pot," are not impacted by water, generate minimal and inoffensive byproducts, and are "spring-loaded"—e.g., characterized by a high thermodynamic driving force that drives the click reaction quickly and irreversibly to high yield of a single reaction product, with high reaction specificity.

Also useful for joining a first and/or putative second dimerizer with either the N-terminus or C-terminus of the split nucleic acid-guided nuclease are HaloTags. HaloTags are self-labeling protein tags comprising a 297 residue protein (33 kDa) derived from a bacterial enzyme, designed to covalently bind to a synthetic ligand and fused to various proteins of interest. The synthetic ligand is chosen from a number of available ligands in accordance with the type of experiments to be performed. The bacterial enzyme is a haloalkane dehalogenase, which acts as a hydrolase and is designed to facilitate, inter alia, capture binding partners of a protein of interest.

A HaloTag is composed of two covalently bound segments including a haloalkane dehalogenase and a synthetic ligand of choice comprising a reactive chloroalkane linker bound to a functional group. The reaction that forms the bond between the protein tag and chloroalkane linker is fast and essentially irreversible under physiological conditions due to the terminal chlorine of the linker portion. In this reaction, nucleophilic attack of the chloroalkane reactive linker causes displacement of the halogen with an amino acid residue, resulting in the formation of a covalent alkyl-enzyme intermediate. This intermediate would then be hydrolyzed by an amino acid residue within the wild-type hydrolase, leading to regeneration of the enzyme following the reaction. However, in the modified haloalkane dehalogenase (i.e., the HaloTag), the reaction intermediate cannot proceed through a subsequent reaction because it cannot be hydrolyzed due to the mutation in the enzyme, causing the intermediate to persist as a stable covalent adduct with which there is no associated back reaction. In addition, HaloTag fusion proteins can be expressed using standard recombinant protein expression techniques and there are several commercial vectors available that just require insertion of a gene of interest.

Yet another technology useful for joining a first and/or putative second dimerizer with either the N-terminus or C-terminus of the split nucleic acid-guided nuclease involve SNAP-tags® (New England Biolabs, Inc., Waltham, MA, USA), which are self-labeling protein tags commercially available in various expression vectors and comprise a 182 residue polypeptide (19.4 kDa) that can be fused to any protein of interest and specifically and covalently tagged with a suitable ligand. The SNAP-tag® protein is an engineered version of the mammalian enzyme AGT, encoded in humans by the 06-methylguanine-DNA methyltransferase (MGMT) gene. The engineered SNAP-tag® was obtained using a directed evolution strategy, leading to variant that accepts 06-benzylguanine derivatives instead of repairing alkylated guanine derivatives in damaged DNA.

An orthogonal tag, called CLIP-tag™, was further engineered from SNAP-tag to accept 02-benzylcytosine derivatives as substrates, instead of 06-benzylguanine. Therefore, Clip-tag- and SNAP-tag-fused proteins can be labeled simultaneously in the same cells.

In yet another example, the SpyTag/SpyCatcher system allows for irreversible conjugation of recombinant proteins. The peptide SpyTag (13 amino acids) spontaneously reacts with the protein SpyCatcher (12.3 kDa) to form an intermolecular isopeptide bond between the pair. A DNA sequence encoding either SpyTag or SpyCatcher can be introduced into the DNA sequence encoding a protein of interest, forming a fusion protein. These fusion proteins can be covalently linked when mixed in a reaction through the SpyTag/SpyCatcher system.

Dimerizers

The present disclosure provides compositions of matter and methods for dimerization screening assays that detect dimerization events between dimerizers, or binding pairs. The dimerization screening assays allow for screening of massive numbers of binding pairs, and provide high accuracy, low cost, and minimum workflow, particularly when performed with microfluidic instrumentation. Biological and chemical moieties that may be screened for dimerization include, antibodies, antigens, dimerizing small molecules known as molecular glues, heterobifunctional dimerizing molecules, small molecule ligands to proteins or nucleic acids, non-nucleic acid targets of interest, aptamers, and DNA or RNA molecules or proteins and other molecules involved in bimolecular interactions.

In any of the embodiments of the disclosure, the library of putative dimerizers includes 1 to about 10,000 or more different putative dimerizers, e.g., 1, 2, 3, 4, 5, 6, 7, 8, 9, 10, 11, 12, 13, 14, 15, 16, 27, 28, 19, 20, 21, 22, 23, 24, 25, 50, 75, 100, 125, 150, 175, 200, 250, 300, 350, 400, 450, 500, 550, 600, 650, 700, 750, 800, 850, 900, 950, 1,000, 2,500, 5,000, 7,500, 10,000, 100,000, 500,000, 1,000,000, 2,500,000, 5,000,000, 10,000,000 or more different putative dimerizers).

Guide RNA (gRNA)

The present disclosure detects a dimerizing event via a reaction mixture containing at least two guide RNAs (gRNAs), each incorporated into a different RNP complex (i.e., RNP1 and RNP2). Suitable gRNAs include at least one crRNA region to enable specificity in every reaction. The gRNA of RNP1 is specific to an RNP1 activating nucleic acid, and the gRNA of RNP2 is specific to, depending on the embodiment of the dimerization screening assays employed, an unblocked nucleic acid or a synthesized activating molecule or an RNP2 activating nucleic acid (all described in detail below). A particularly advantageous feature of the dimerization screening assays is that, with the exception of the putative dimerizers (i.e., binding pairs) that are fused to the N-terminal and C-terminal portions of the split Cas enzyme, the dimerization screening assay components can be the same for each dimerization screening assay no matter what putative binding pairs of interest are being detected.

Like the nucleic acid-guided nuclease, in certain embodiments, the gRNA may be provided in the dimerization screening assay reaction mix in a preassembled RNP or as an RNA molecule. In the present dimerization screening assay embodiments, only RNP2 can be provided as a preassembled RNP and only in the embodiments where a blocked nucleic acid molecule or blocked primer molecule is employed.

The gRNA of RNP1 is capable of complexing with a reconstituted split Cas enzyme of RNP1 to perform cis-cleavage of the RNP1 activating nucleic acid (e.g., a DNA or RNA), which triggers non-sequence specific trans-cleavage of other molecules in the reaction mix. Guide RNAs include any polynucleotide sequence having sufficient complementarity with an activating nucleic acid whether it is an RNP1 activating nucleic acid, an RNP2 activating nucleic acid, or a synthesized activating nucleic acid. Activating nucleic acids may and often do include a protospacer-adjacent motif (PAM).

In some embodiments, the gRNA (e.g., of RNP1) is an exo-resistant circular molecule that can include several DNA bases between the 5' end and the 3' end of a natural guide RNA and is capable of binding the RNP1 activating nucleic acid. The length of the circularized guide for RNP1 can be such that the circular form of guide can be complexed with a nucleic acid-guided nuclease to form a modified RNP1 that can still retain its cis-cleavage i.e., (specific) and trans-cleavage (i.e., non-specific) nuclease activity.

In any of the foregoing embodiments, the gRNA may comprise a modified or non-naturally occurring nucleic acid molecule. In some embodiments, the gRNAs of the disclosure may further contain a locked nucleic acid (LNA), a bridged nucleic acid (BNA), and/or a peptide nucleic acid (PNA). By way of further example, a modified nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, or any other nucleic acid molecule modifications described herein.

Blocked guide RNAs (i.e., blocked gRNAs) are specific for the RNP2 activating nucleic acid in one embodiment of the dimerization screening assays. A blocked gRNA has low binding affinity to the second, intact Cas enzyme and can prevent RNP2 complex formation. In some embodiments, the blocked gRNA can be a chimeric molecule and can comprise about 2, 3, 4, 5, 6, 7, 8, 9, 10, 15, 20, 25, 30, 35, 40, 45, 50, 55, 60, 65, 70, 75, 80, or more deoxyribonucleotides and about 1, 2, 3, 4, 5, 6, 7, 8, 9, 10, 15, 20, 25, 30, 35, 40, or 45 ribonucleotides. In some embodiments, about 25 of the ribonucleotides are for Cas (e.g., Cas12a, Cas12b, Cas12c, Cas12d, Cas12e, Cas14, Cas12h, Cas12i, Cas12j, Cas13a, or Cas12g) internalization and about 20 of the ribonucleotides are homologous to the RNP2 activating nucleic acid. In some embodiments, two or more (e.g., about 2, 3, 4, 5, 6, 7, 8, 9, 10, 20, 30, 40, 50, 60, 70, 80 or more) of the deoxyribonucleotides have one or more secondary structures and may be GC rich. In some embodiments, the blocked gRNA comprises two or more deoxyribonucleotides and about 45 ribonucleotides, wherein about 25 of the ribonucleotides are for Cas (e.g., Cas12a, Cas12b, Cas12c, Cas12d, Cas12e, Cas14, Cas12h, Cas12i, Cas12j, Cas13a, or Cas12g) internalization and about 20 of the ribonucleotides are homologous to the RNP2 activating nucleic acid.

In some embodiments of the blocked gRNA, the 5' end and 3' end of the blocked gRNA can be covalently linked to form a circular molecule, where the circular gRNA has connecting and cleavable DNA molecules. The circular gRNA design sterically blocks the molecule from internalization into the second, intact Cas enzyme (e.g., Cas12a, Cas12b, Cas12c, Cas12d, Cas12e, Cas14, Cas12h, Cas12i, or Cas12j) and thus prevents formation of an RNP complex (e.g., RNP2). The DNA portion of the gRNA will be cleavable only by trans-cleavage of activated RNP1 (or RNP2) in the reaction. For example, in some embodiments, an activated RNP1 complex can cleave the DNA portion of a circular gRNA molecule by trans-cleavage. After cleaving of the DNA portion, the circular gRNA molecule converts to a linear gRNA molecule. The linear gRNA molecule then exhibits low $K_d$ (i.e., is unblocked) and is not sterically blocked from internalization into RNP2 with the second, intact Cas enzyme (e.g., Cas12a, Cas12b, Cas12c, Cas12d, Cas12e, Cas14, Cas12h, Cas12i, or Cas12j). In some embodiments, the linear gRNA can bind to Cas12a, Cas12b, Cas12c, Cas12d, Cas12e, Cas14, Cas12h, Cas12i, or Cas12j enzyme and form the RNP2 complex.

The trans-cleavage activity of activated RNP1 converts the blocked gRNA specific for the RNP2 activating nucleic acid (specific to RNP2) to form an unblocked gRNA for subsequent RNP2 formation. In some embodiments, the unblocked gRNA resulting from trans-cleavage of the circular blocked gRNA molecule is a linear molecule resembling the gRNA of the second, intact Cas enzyme (e.g., Cas12b, Cas12c, Cas12d, Cas12e, Cas14, Cas12h, Cas12i, or Cas12j). In some embodiments, the resulting blocked gRNA is a linear molecule resembling the native, unmodified gRNA of the second, intact Cas enzyme (e.g., Cas12b, Cas12c, Cas12d, Cas12e, Cas14, Cas12h, Cas12i, or Cas12j) such as those of Cas12a described in Hewes, Molecular Therapy-Nucleic Acids, 20: 568-579 (2020).

Low $K_d$ values of unblocked gRNA can be about 1 nM to about 10 nM (e.g., about 1, 2, 3, 4, 5, 6, 7, 8, 9, 10 nM or lower or any range between about 1 nM to about 10 nM). High $K_d$ values for the blocked gRNAs can be about 10, 100, 1000, or more times higher as compared to low $K_d$ values.

Ribonucleoprotein (RNP) Complex

As described above, the dimerization screening assay "reaction mix" may comprise separate nucleic acid-guided nucleases and gRNAs (or coding sequences therefor); however, in certain of the embodiments of the dimerization screening assays—those employing blocked nucleic acid molecules or blocked primer molecules—preassembled ribonucleoprotein complexes may be used for RNP2 in the reaction mix. The present dimerization screening assays employ at least two types of RNP complexes— RNP1 and RNP2— where RNP1 comprises the split Cas enzyme, if reconstituted, and the gRNA1; and RNP2 comprises the second, intact Cas enzyme and gRNA2. gRNA1 is complementary to the RNP1 activating nucleic acid. gRNA2 is complementary to the unblocked nucleic acid molecule, the synthesized activating molecule, or the RNP2 activating nucleic acid, depending on the dimerization screening assay employed. RNP1 and RNP2 cannot comprise the same nucleic acid-guided nuclease thus must comprise different nucleic acid-guided nucleases.

In some embodiments, the reaction mixture contains RNP1 components (i.e., the split Cas enzyme and gRNA1) to produce about 1 fM to about 10 µM of RNP1, or about 1 pM to about 1 µM of RNP1, or about 10 pM to about 500 µM of RNP1. In some embodiments, the reaction mixture contains RNP1 components (i.e., the split Cas enzyme and gRNA1) to produce about $6 \times 10^4$ to about $6 \times 10^{12}$ per microliter (µl) RNP1s, or about $6 \times 10^6$ to about $6 \times 10^{10}$ per microliter (µl) of RNP1s. In some embodiments, the reaction mixture contains about 1 fM to about 500 µM of RNP2 (or components therefor to produce RNP2), or about 1 pM to about 250 µM of RNP2 (or components therefor to produce RNP2), or about 10 pM to about 100 µM of RNP2 (or components therefor to produce RNP2). In some embodiments, the reaction mixture contains RNP2 components (i.e., the second, intact Cas enzyme and gRNA2) to produce about $6 \times 10^4$ to about $6 \times 10^{12}$ complexes per microliter (µl) or about $6 \times 10^6$ to about $6 \times 10^{12}$ complexes per microliter (µl)

Reporter Moieties

The dimerization screening assays herein detect a dimerization event via detection of a signal generated in the reaction mix by a reporter moiety. In most embodiments, trans- and/or cis-cleavage by the nucleic acid-guided nuclease in RNP2 releases a signal. In some embodiments, trans-cleavage of stand-alone reporter moieties (e.g., not bound to any blocked nucleic acid molecules or blocked primer molecules) may generate signal changes at rates that are proportional to the cleavage rate, as new RNP2s are activated over time (shown in FIG. 1 and at top of FIG. 6). Trans-cleavage by either an activated RNP1 or an activated RNP2 may release a signal. In two of the embodiments described herein and preferably, the reporter moiety may be bound to the blocked nucleic acid molecule or blocked primer molecule, where trans-cleavage of the blocked nucleic acid molecule or blocked primer molecule and conversion to an unblocked nucleic acid molecule or unblocked primer molecule may generate signal changes at rates that are proportional to the cleavage rate, as new RNP2s are activated over time, thus allowing for real time reporting of results (shown at FIG. 6, center). In yet another embodiment, the reporter moiety may be bound to a blocked nucleic acid molecule such that cis-cleavage following the binding of the RNP2 to an unblocked nucleic acid molecule releases a PAM distal sequence, which in turn generates a signal at rates that are proportional to the cleavage rate (shown at FIG. 6, bottom). In this case, activation of RNP2 by cis-(target specific) cleavage of the unblocked nucleic acid molecule directly produces a signal, rather than producing a signal via indiscriminate trans-cleavage activity. Alternatively or in addition, a reporter moiety may be bound to the gRNA.

The reporter moiety may include a synthetic molecule linked or conjugated to a reporter and quencher such as, for example, a TaqMan probe with a dye label (e.g., FAM or FITC) on the 5' end and a quencher on the 3' end. The reporter and quencher may be about 20-30 bases apart or less (i.e., 10-11 nm apart or less) for effective quenching via fluorescence resonance energy transfer (FRET). Alternatively, signal generation may occur through different mechanisms. Other detectable moieties, labels, or reporters can also be used to detect a target nucleic acid of interest as described herein. Reporter moieties can be labeled in a variety of ways, including direct or indirect attachment of a detectable moiety such as a fluorescent moiety, hapten, or colorimetric moiety.

Examples of detectable moieties include, but are not limited to, various radioactive moieties, enzymes, prosthetic groups, fluorescent markers, luminescent markers, bioluminescent markers, metal particles, and protein-protein binding pairs, e.g., protein-antibody binding pairs. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, and phycoerythrin. Examples of bioluminescent markers include, but are not limited to, luciferase (e.g., bacterial, firefly, click beetle and the like), luciferin, and aequorin. Examples of enzyme systems having visually detectable signals include, but are not limited to, galactosidases, glucorinidases, phosphatases, peroxidases, and cholinesterases. Identifiable markers also include radioactive elements such as $^{125}$I, $^{35}$S, $^{14}$C or $^3$H. Reporters can also include a change in pH or charge of the cascade assay reaction mix.

The methods used to detect the generated signal will depend on the reporter moiety or moieties used. For example, a radioactive label can be detected using a scintillation counter, photographic film as in autoradiography, or storage phosphor imaging. Fluorescent labels can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers, and the like. Enzymatic labels can be detected by providing the appropriate substrates for the enzyme and detecting the resulting reaction product. Simple colorimetric labels can be detected by observing the color associated with the label. When pairs of fluorophores are used in an assay, fluorophores are chosen that have distinct emission patterns (wavelengths) so that they can be easily distinguished.

Single-stranded nucleic acid reporter moieties, such as ssDNA reporter moieties or RNA molecules, can be introduced to show a signal change proportional to the cleavage rate, which increases with every new activated RNP2 complex over time. In some embodiments and as described in detail below, single-stranded nucleic acid reporter moieties can also be embedded into the blocked nucleic acid molecules (or blocked primer molecules) for real time reporting of results.

For example, the method of detecting a dimerization event in a sample using a dimerization screening assay as described herein can involve contacting the reaction mix with a labeled detection ssDNA containing a fluorescent resonance energy transfer (FRET) pair, a quencher/phosphor pair, or both. A FRET pair consists of a donor chromophore and an acceptor chromophore, where the acceptor chromophore may include a quencher molecule. FRET pairs (donor/acceptor) suitable for use include, but are not limited to, EDANS/fluorescein, IAEDANS/fluorescein, fluorescein/tetramethylrhodamine, fluorescein/Cy 5, IEDANS/

DABCYL, fluorescein/QSY-7, fluorescein/LC Red 640, fluorescein/Cy 5.5, Texas Red/DABCYL, BODIPY/DABCYL, Lucifer yellow/DABCYL, coumarin/DABCYL, and fluorescein/LC Red 705. In addition, a fluorophore/quantum dot donor/acceptor pair can be used. EDANS is (5-((2-Aminoethyl)amino)naphthalene-1-sulfonic acid); IAEDANS is 54{2-[(iodoacetyl)amino]ethyl} amino)naphthalene-1-sulfonic acid); DABCYL is 4-(4-dimethylaminophenyl) diazenylbenzoic acid. Useful quenchers include, but are not limited to, BHQ, DABCYL, QSY 7 and QSY 33.

In any of the foregoing embodiments, the reporter moiety may comprise one or more modified nucleic acid molecules, containing a modified nucleoside or nucleotide. In some embodiments the modified nucleoside or nucleotide is chosen from 2'-O-methyl (2'-O-Me) modified nucleoside, a 2'-fluoro (2'-F) modified nucleoside, and a phosphorothioate (PS) bond, or any other nucleic acid molecule modifications described below.

Nucleic Acid Modifications

For any of the nucleic acid molecules described herein (e.g., RNP1 and/or RNP2 activating nucleic acids, blocked nucleic acid molecules, blocked primer molecules, blocked guide nucleic acids, gRNAs, template molecules, synthesized activating nucleic acids, and reporter moieties), the nucleic acid molecules may be used in a wholly or partially modified form. Typically, modifications to nucleic acid molecules described herein are introduced to optimize the molecule's biophysical properties (e.g., increasing nucleic acid-guided nuclease resistance and/or increasing thermal stability). Modifications typically are achieved by the incorporation of, for example, one or more alternative nucleosides, alternative sugar moieties, and/or alternative internucleoside linkages.

For example, one or more of the dimerization screening assay components may include one or more of the following nucleoside modifications: 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, and/or 3-deazaguanine and 3-deazaadenine. The nucleic acid molecules described herein may also include nucleobases in which the purine or pyrimidine base is replaced with other heterocycles, for example 7-deaza-adenine, 7-deazaguanosine, 2-aminopyridine, and/or 2-pyridone. Further modification of the nucleic acid molecules described herein may include nucleobases disclosed in U.S. Pat. No. 3,687,808; Kroschwitz, ed., The Concise Encyclopedia of Polymer Science and Engineering, NY, John Wiley & Sons, 1990, pp. 858-859; Englisch, et al., *Angewandte Chemie*, 30:613 (1991); and Sanghvi, Chapter 16, Antisense Research and Applications, CRC Press, Gait, ed., 1993, pp. 289-302.

In addition to or as an alternative to nucleoside modifications, the cascade assay components may comprise 2' sugar modifications, including 2'-O-methyl (2'-O-Me), 2'-methoxyethoxy (2'—O—CH$_2$CH$_2$OCH$_3$, also known as 2'-O-(2-methoxyethyl) or 2'-MOE), 2'-dimethylaminooxyethoxy, i.e., a O(CH$_2$)$_2$ON(CH$_3$)$_2$ group, also known as 2'-DMAOE, and/or 2'-dimethylaminoethoxyethoxy (also known in the art as 2'-O-dimethylamino-ethoxy-ethyl or 2'-DMAEOE), i.e., 2'—O—CH$_2$OCH$_2$N(CH$_3$)$_2$. Other possible 2'-modifications that can modify the nucleic acid molecules described herein (i.e., RNP1 and RNP2 activating nucleic acids, blocked nucleic acids, blocked guide nucleic acids, gRNAs, synthesized activating nucleic acids, reporter molecules, and blocked primer molecules) may include all possible orientations of OH; F; O—, S—, or N-alkyl (mono- or di-); O—, S—, or N-alkenyl (mono- or di-); O—, S- or N-alkynyl (mono- or di-); or O-alkyl-O-alkyl, wherein the alkyl, alkenyl and alkynyl may be substituted or unsubstituted C1 to C10 alkyl or C2 to C10 alkenyl and alkynyl. Other potential sugar substituent groups include, e.g., aminopropoxy (—OCH$_2$CH$_2$CH$_2$NH$_2$), allyl (—CH$_2$—CH=CH$_2$), —O-allyl (—O—CH$_2$—CH=CH$_2$) and fluoro (F). 2'-sugar substituent groups may be in the arabino (up) position or ribo (down) position. In some embodiments, the 2'-arabino modification is 2'-F. Similar modifications may also be made at other positions on the interfering RNA molecule, particularly the 3' position of the sugar on the 3' terminal nucleoside or in 2'-5' linked oligonucleotides and the 5' position of 5' terminal nucleotide. Oligonucleotides may also have sugar mimetics such as cyclobutyl moieties in place of the pentofuranosyl sugar.

Finally, modifications to the dimerization screening assay components may comprise internucleoside modifications such as phosphorothioates, phosphorodithioates, phosphotriesters, aminoalkylphosphotriesters, methyl and other alkyl phosphonates including 3'-alkylene phosphonates, 5'-alkylene phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage.

The Dimerization Screening Assay Employing Blocked Nucleic Acids

Figure 3A:
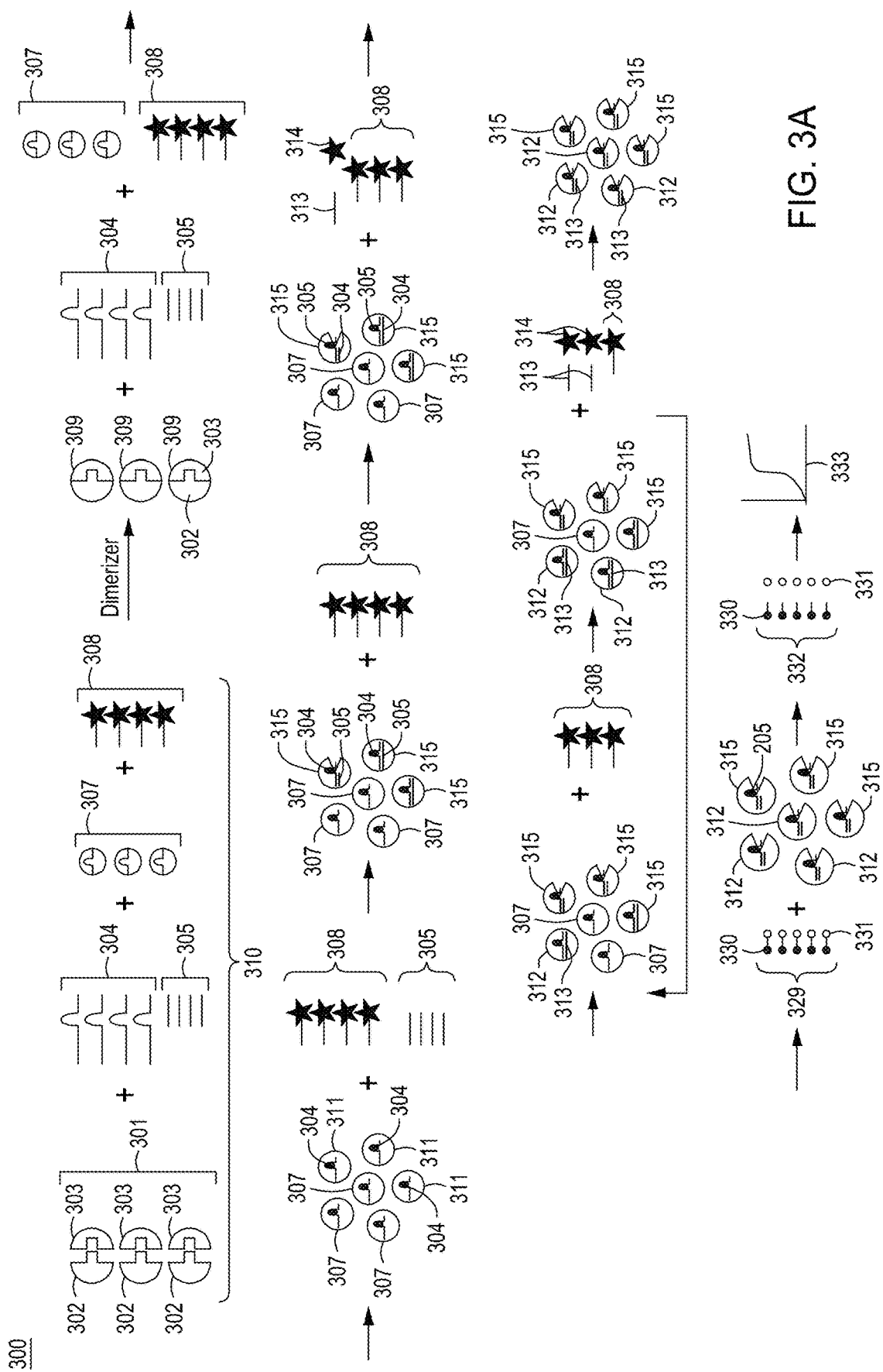
FIG. 3A is a diagram showing the sequence of steps in an exemplary dimerization screening assay utilizing a split Cas enzyme and blocked nucleic acid molecules, according to certain embodiments.

FIG. 1, described above, generally depicts the signal boost cascade assay upon which the dimerization screening assays herein are based. As described above, there are at least three basic embodiments of the dimerization screening assays, where each of the three embodiments results in an exponential signal boost upon detection of a dimerization event. The three embodiments differ in the type of blocked molecule is used to "lock" RNP2. A first embodiment of the dimerization screening assays 300 utilizes blocked nucleic acids and is depicted in FIG. 3A and described in detail below. In this embodiment, a blocked nucleic acid molecule is used to prevent the activation of RNP2 in the absence of a dimerization event.

The dimerization screening assay 300 in FIG. 3A begins with providing the cascade assay components in a reaction mix 310 comprising: 1) dimerizer/N-terminal portion of split Cas enzyme 302; 2) dimerizer/C-terminal portion of split Cas enzyme 303 (i.e., the di-N-term 302 and di-C-term 303 comprise cascade assay components 301); 3) first guide nucleic acids (gRNA1) 304; 4) RNP1 activating nucleic acids 305; 5) RNP2s 307; 6) blocked nucleic acid molecules 308; and 7) reporter moieties 329 (only shown at bottom of FIG. 3A). The RNP2s comprise a gRNA specific for unblocked nucleic acid molecules resulting from the unblocking of blocked nucleic acid molecules and a second, intact nuclease (e.g., Cas 12a or Cas 14 for a DNA unblocked nucleic acid molecule or a Cas 13a for an RNA unblocked nucleic acid molecule). The split Cas enzyme that, if reconstituted, will form RNP1 with gRNA1 and the second, intact Cas enzyme in RNP2 must be different. The Cas enzymes in RNP1 and RNP2 must also, when activated, possess trans-cleavage activity following binding of an RNP1 activating nucleic acid or unblocked nucleic acid molecule, respectively.

In a first step, a dimerization event takes place, bringing the di-N-term 302 and di-C-term 303 portions of the split Cas enzyme together, thereby reconstituting a functional first Cas enzyme 309. The functional first Cas enzyme 309 is now in the reaction mix with the first guide nucleic acid (gRNA1) 304, RNP1 activating nucleic acids 305, RNP2s 307, and blocked nucleic acid molecules 308. The functional first Cas enzyme 309 now can internalize gRNA1 304 to form RNP1 311 (also seen are RNP1 activating nucleic acids 305, RNP2s 307, and blocked nucleic acid molecules 308). In a next step, RNP1 311 complexes with RNP1 activating nucleic acids 305 to form activated RNP1s 315. The activated RNP1s 315 cleave via cis-cleavage the RNP1 activating nucleic acids 305, and indiscriminate trans-cleavage of other nucleic acids present in the reaction mix is activated as well, including at least one of the blocked nucleic acid molecules 308. Thus, at least one of the blocked nucleic acid molecules 308 becomes an unblocked nucleic acid molecule 313 when the blocking moiety 314 is removed. As described below, "blocking moiety" may refer to nucleoside modifications, topographical configurations such as secondary structures, and/or structural modifications.

Once at least one of the blocked nucleic acid molecules 308 is unblocked, the unblocked nucleic acid molecule 313 can then complex with (i.e., internalize into) RNP2 307 and activate RNP2 312. Because the nucleic acid-guided nucleases in the activated RNP1s 315 and RNP2s 312 have both cis- and trans-cleavage activity, the trans-cleavage activity of both RNP1 315 and RNP2 312 causes more blocked nucleic acid molecules 308 to become unblocked nucleic acid molecules 313, thereby triggering activation of even more RNP2s 312 and more trans-cleavage activity in a reaction cascade.

FIG. 3A at bottom depicts the concurrent activation of reporter moieties. Intact reporter moieties 329 comprise a quencher 330 and a fluorophore 331 linked by a nucleic acid sequence. As described above in relation to FIG. 1, the intact reporter moieties 329 are also subject to trans-cleavage by activated RNP1 315 and RNP2 312. The intact reporter moieties 329 become activated reporter moieties 332 when the quencher 330 is separated from the fluorophore 331, emitting a fluorescent signal 333. Signal strength increases rapidly as more blocked nucleic acid molecules 308 become unblocked nucleic acid molecules 313 triggering activation of RNP2 312 and further trans-cleavage activity of the reporter moieties 329. Again, the reporter moieties are shown here as separate molecules from the blocked nucleic acid molecules, but other configurations may be employed and are discussed in relation to FIG. 6. As noted above, a particularly advantageous feature of the dimerization screening assay is that, with the exception of the putative dimerizers that are fused to the N-terminal and C-terminal portions of the split Cas enzyme, the dimerization screening assay components can be the same in each assay no matter what putative binding pairs of interest are being detected.

Figure 3B:
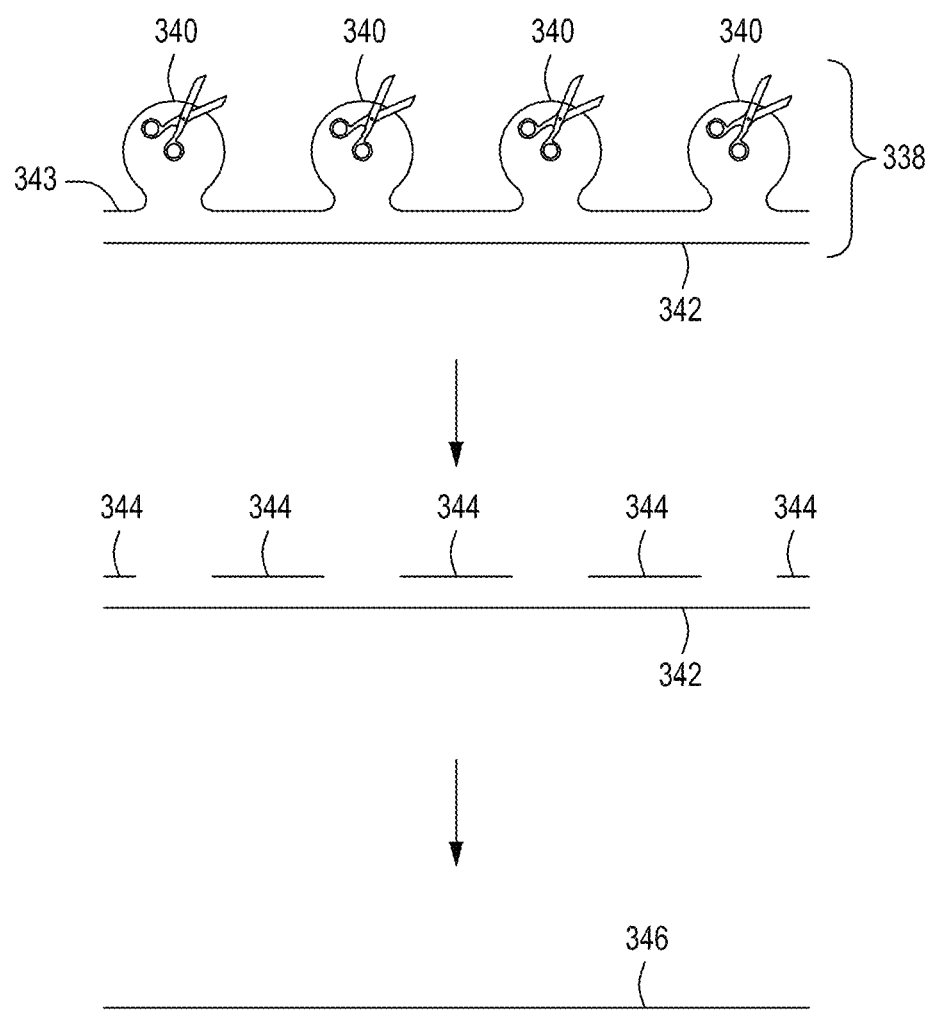
FIG. 3B is a diagram showing an exemplary blocked nucleic acid molecule and the concept behind unblocking some embodiments of the blocked nucleic acid molecules of the disclosure.

FIG. 3B is a diagram showing an exemplary blocked nucleic acid molecule 338 and an exemplary technique for unblocking the blocked nucleic acid molecules described herein. A blocked single-stranded or double-stranded, circular or linear, DNA or RNA molecule 338 comprising a target strand 342 may contain a partial hybridization with a complementary non-target strand nucleic acid molecule 343 containing unhybridized and cleavable secondary loop structures 340 (e.g., hairpin loops, tetraloops, pseudoknots, junctions, kissing hairpins, internal loops, bulges, and multibranch loops). Trans-cleavage of the loops by activated RNP1s or RNP2s generates short strand nucleotide sequences or regions 344 which, because of their short length and low melting temperature, can dehybridize from target strand 342 at room temperature (e.g., 15°–25° C.), thereby unblocking the blocked nucleic acid molecule 338 to create an unblocked nucleic acid molecule 346, enabling the internalization of the unblocked nucleic acid molecule 346 (target strand) into an RNP2, leading to RNP2 activation.

Figure 3C:
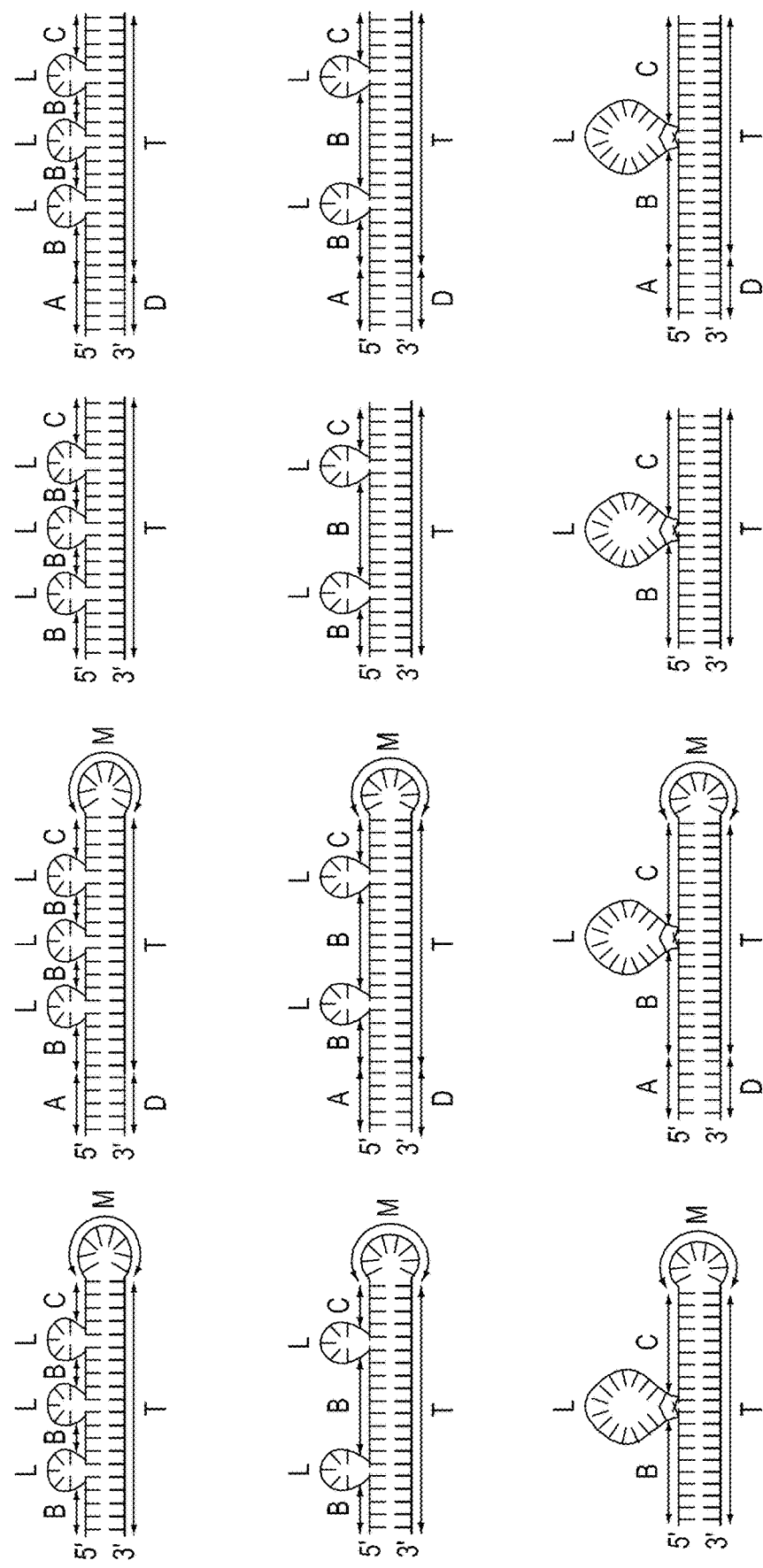
FIG. 3C shows schematics of several exemplary blocked nucleic acid molecules containing the structure of Formula I, as described herein.
Figure 3D:
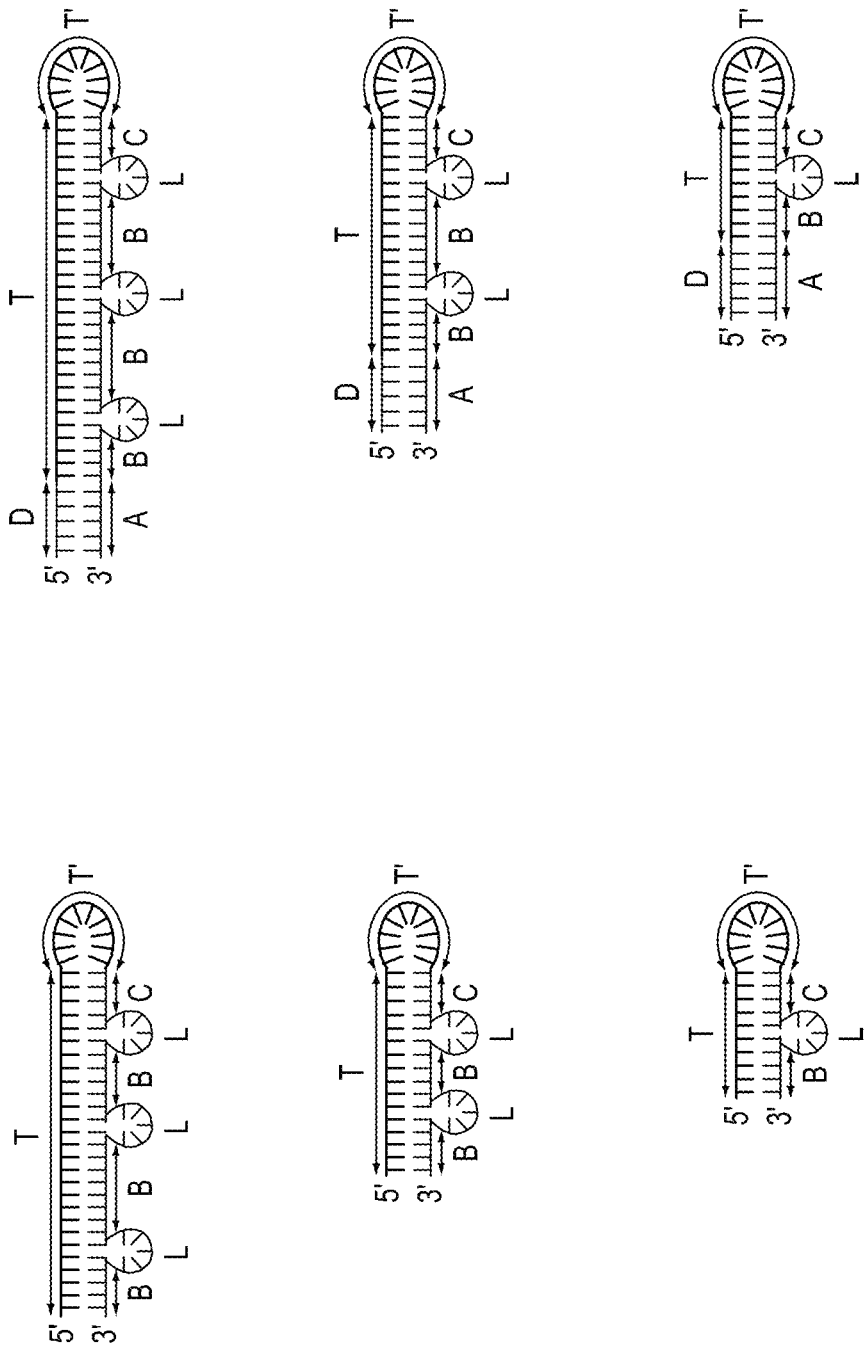
FIG. 3D shows schematics of several exemplary blocked nucleic acid molecules containing the structure of Formula II, as described herein.
Figure 3E:
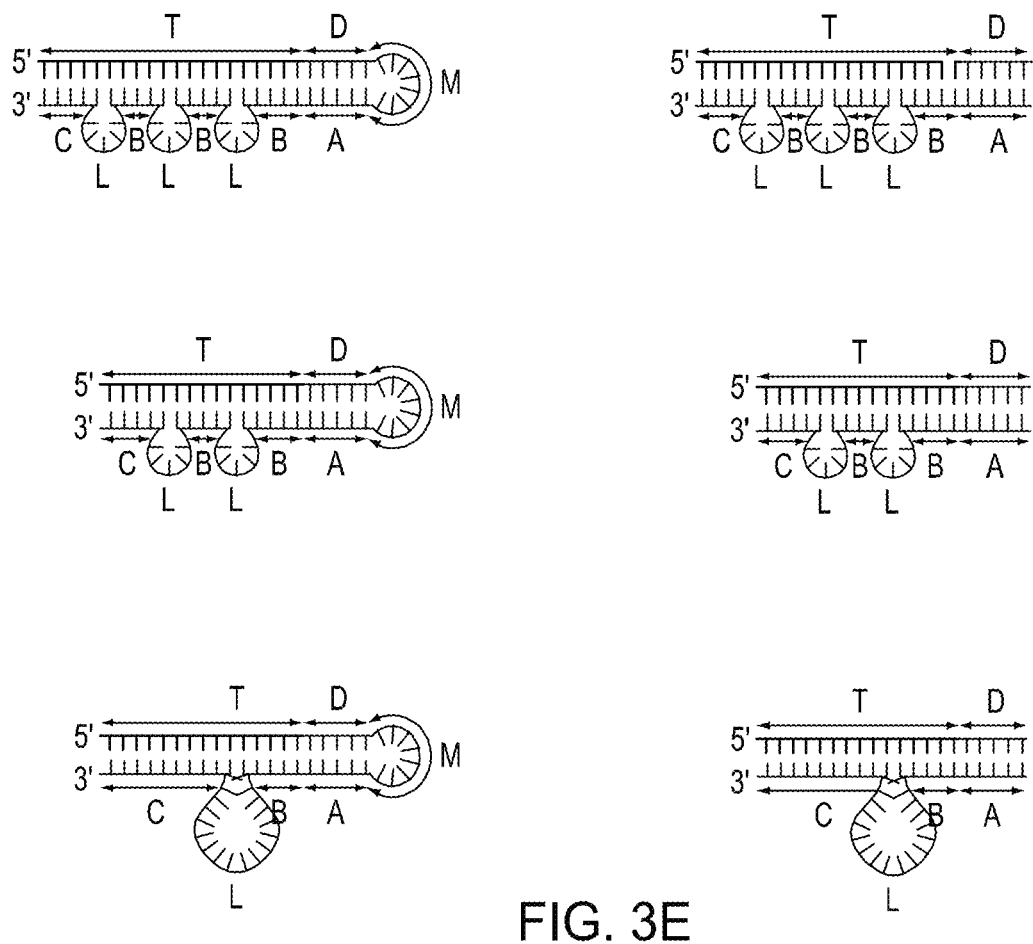
FIG. 3E shows schematics of several exemplary blocked nucleic acid molecules containing the structure of Formula III, as described herein.
Figure 3F:
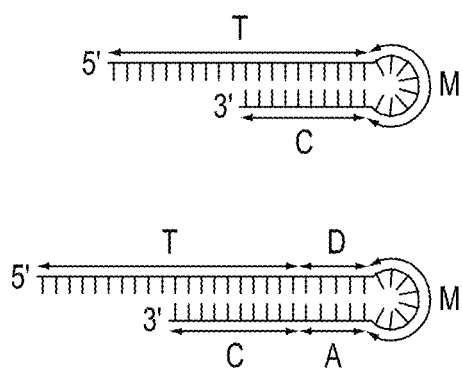
FIG. 3F shows schematics of several exemplary blocked nucleic acid molecules containing the structure of Formula IV, as described herein.

A blocked nucleic acid molecule may be single-stranded or double-stranded, circular or linear, and may further contain a partially hybridized nucleic acid sequence containing cleavable secondary loop structures, as shown in FIG. 3B and exemplified by "L" in FIGS. 3C-3E. Such blocked nucleic acids typically have a low binding affinity, or high dissociation constant ($K_d$) in relation to binding to RNP2 (or, as seen below binding to template molecules) and may be referred to herein as a high $K_d$ nucleic acid molecule. In the context of the present disclosure, the binding of blocked or unblocked nucleic acid molecules or blocked or unblocked guide molecules to RNP2, low $K_d$ values range from about 100 fM to about 1 aM or lower (e.g., 100 zM) and high $K_d$ values are in the range of 100 nM to about 10-100 10 mM and thus are about $10^5$-, $10^6$-, $10^7$-, $10^8$-, $10^9$-to $10^{10}$-fold or higher as compared to low $K_d$ values. Of course, the ideal blocked nucleic acid molecule would have an "infinite $K_d$."

Thus, the blocked nucleic acid molecules (high $K_d$ molecules) described herein can be converted into unblocked nucleic acid molecules (low $K_d$ molecules—also in relation to binding to RNP2) via cleavage of nuclease-cleavable regions (e.g., via active RNP1s and RNP2s). The unblocked nucleic acid molecule has a higher binding affinity for the gRNA in RNP2 than does the blocked nucleic acid molecule. Once the unblocked nucleic acid molecule is bound to RNP2, RNP2 activation triggers trans-cleavage activity, which in turn leads to more RNP2 activation by further cleaving blocked nucleic acid molecules, resulting in a positive feedback loop or cascade.

In embodiments where blocked nucleic acid molecules are linear and/or form a secondary structure, the blocked nucleic acid molecules may include single-stranded (ss) or double-stranded (ds) and contain a first nucleotide sequence and a second nucleotide sequence. The first nucleotide sequence has sufficient complementarity to hybridize to a gRNA of RNP2, and the second nucleotide sequence does not. The first and second nucleotide sequences of a blocked nucleic acid molecule may be on the same nucleic acid molecule (e.g., for single-strand embodiments) or on separate nucleic acid molecules (e.g., for double-strand embodiments). Trans-cleavage (e.g., via RNP1 or RNP2) of the second nucleotide sequence in the blocked nucleic acid molecule converts the blocked nucleic acid molecule to a single-strand unblocked nucleic acid molecule. The unblocked nucleic acid molecule contains only the first nucleotide sequence, which has sufficient complementarity to hybridize to the gRNA of RNP2, thereby activating the trans-cleavage activity of RNP2.

In some embodiments, the second nucleotide sequence at least partially hybridizes to the first nucleotide sequence, resulting in a secondary structure containing at least one loop (e.g., hairpin loops, tetraloops, pseudoknots, junctions, kissing hairpins, internal loops, bulges, and multibranch loops). Such loops block the nucleic acid molecule from binding or incorporating into an RNP complex, thereby initiating cis- or trans-cleavage (see, e.g., the exemplary structures in FIGS. 3C-3F).

In some embodiments, the blocked nucleic acid molecule may contain a protospacer adjacent motif (PAM) sequence, or partial PAM sequence, positioned between the first and second nucleotide sequences, where the first sequence is 5' to the PAM sequence, or partial PAM sequence. Inclusion of a PAM sequence may increase the reaction kinetics internalizing the unblocked nucleic acid molecule into RNP2 and thus decrease the time to detection. In other embodiments, the blocked nucleic acid molecule does not contain a PAM sequence.

In some embodiments, the blocked nucleic acid molecules (i.e., high $K_d$ nucleic acid molecules in relation to binding to RNP2) of the disclosure may include a structure represented by Formula I (e.g., FIG. 3C), Formula II (e.g., FIG. 3D), Formula III (e.g., FIG. 3E), or Formula IV (e.g., FIG. 3F) wherein Formulas I-IV are, in the 5'-to-3' direction:

A-(B-L)J-C-M-T-D  (Formula I);

wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then A-(B-L)J-C and T-D are separate nucleic acid strands;
T is 17-135 nucleotides in length (e.g., 17-100, 17-50, or 17-25) and comprises a sequence complementary to B and C; and
D is 0-10 nucleotides in length and comprises a sequence complementary to A;
and where, in some embodiments, segment A is attached to segment D forming a loop;

D-T-T'-C-(L-B)J-A  (Formula II);

wherein D is 0-10 nucleotides in length;
T-T' is 17-135 nucleotides in length (e.g., 17-100, 17-50, or 17-25);
T' is 1-10 nucleotides in length and does not hybridize with T;
C is 4-15 nucleotides in length and comprises a sequence complementary to T;
L is 3-25 nucleotides in length and does not hybridize with T;
B is 4-12 nucleotides in length and comprises a sequence complementary to T;
J is an integer between 1 and 10;
A is 0-15 nucleotides in length and comprises a sequence complementary to D; and where, in some embodiments, segment T is attached to segment B forming a loop;

T-D-M-A-(B-L)J-C  (Formula III);

wherein T is 17-135 nucleotides in length (e.g., 17-100, 17-50, or 17-25);
D is 0-10 nucleotides in length;
M is 1-25 nucleotides in length or is absent, wherein if M is absent then T-D and A-(B-L)J-C are separate nucleic acid strands;
A is 0-15 nucleotides in length and comprises a sequence complementary to D;
B is 4-12 nucleotides in length and comprises a sequence complementary to T;
L is 3-25 nucleotides in length;
J is an integer between 1 and 10; and
C is 4-15 nucleotides in length;
and where, in some embodiments, segment T is attached to segment C forming a loop;

T-D-M-A-Lp-C  (Formula IV);

wherein T is 17-31 nucleotides in length (e.g., 17-100, 17-50, or 17-25);
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

In alternative embodiments of any of these molecules, T (or T-T') can have a maximum length of 1000 nucleotides, e.g., at most 750, at most 500, at most 400, at more 300, at most 250, at most 200, at most 150, at most 135, at most 100, at most 75, at most 50, or at most 25 nucleotides.

Nucleotide mismatches can be introduced in any of the above structures containing double-strand segments (for example, where M is absent in Formula I or Formula III) to reduce the melting temperature ($T_m$) of the segment such that once the loop (L) is cleaved, the double-strand segment is unstable and dehybridizes rapidly. The percentage of nucleotide mismatches of a given segment may vary between 0% and 50%; however, the maximum number of nucleotide mismatches is limited to a number where the secondary loop structure still forms. "Segments" in the above statement refers to A, B, and C. In other words, the number of hybridized bases can be less than or equal to the length of each double-strand segment and vary based on number of mismatches introduced.

In any blocked nucleic acid molecule having the structure of Formula I, III, or IV, T will have sequence complementarity to a nucleotide sequence (e.g., a spacer sequence) within a gRNA of RNP2. The nucleotide sequence of T is to be designed such that hybridization of T to the gRNA of RNP2 activates the trans-nuclease activity of RNP2. In any blocked nucleic acid molecule having structure of Formula II, T-T' will have sequence complementarity to a sequence (e.g., a spacer sequence) within the gRNA of RNP2. The nucleotide sequence of T-T' is to be designed such that hybridization of T-T' to the gRNA of RNP2 activates the trans-nuclease activity of RNP2. For T or T-T', full complementarity to the gRNA is not necessarily required, provided there is sufficient complementarity to cause hybridization and trans-cleavage activation of RNP2.

In any of the foregoing embodiments, the blocked nucleic acid molecules of the disclosure may further contain a reporter moiety attached thereto such that cleavage of the blocked nucleic acid releases a signal from the reporter moiety. (See FIG. 6, mechanisms depicted at center and bottom.)

Also, in any of the foregoing embodiments, the blocked nucleic acid molecule may include a modified or non-naturally occurring nucleic acid molecule. In some embodiments, the blocked nucleic acid molecules of the disclosure may further contain a locked nucleic acid (LNA), a bridged nucleic acid (BNA), and/or a peptide nucleic acid (PNA). The blocked nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, any other nucleic acid molecule modifications described above, and any combination thereof.

In some embodiments, the blocked nucleic acid molecules provided herein are circular DNAs, RNAs, or chimeric (DNA-RNA) molecules, and the blocked nucleic acid molecules may include different base compositions depending on the Cas enzyme used for RNP1 and RNP2. For the circular design of blocked nucleic acid molecules, the 5' and 3' ends are covalently linked together. This configuration makes internalization of the blocked nucleic acid molecule into RNP2— and subsequent RNP2 activation—sterically unfavorable, thereby blocking the progression of the cascade assay. Thus, RNP2 activation (e.g., trans-cleavage activity) happens after cleavage of a portion of the blocked nucleic acid molecule followed by linearization and internalization of unblocked nucleic acid molecule into RNP2.

In some embodiments, the blocked nucleic acid molecules are topologically circular molecules with 5' and 3' portions hybridized to each other using DNA, RNA, LNA, BNA, or PNA bases which have a very high melting temperature ($T_m$). The high $T_m$ causes the structure to effectively behave as a circular molecule even though the 5' and 3' ends are not covalently linked. The 5' and 3' ends can also have base non-naturally occurring modifications such as phosphorothioate bonds to provide increased stability.

In embodiments where the blocked nucleic acid molecules are circularized (i.e., circular or topologically circular), each blocked nucleic acid molecule includes a first region, which is a target sequence specific to the gRNA of RNP2, and a second region, which is a sequence that can be cleaved by nuclease enzymes of activated RNP1 and/or RNP2. The first region may include a nuclease-resistant nucleic acid sequence such as, for example, a phosphorothioate group or other non-naturally occurring nuclease-resistant base modifications, for protection from trans-nucleic acid-guided nuclease activity. In some embodiments, when the Cas enzyme in both RNP1 and RNP2 is a Cas RNA-guided DNA nucleic acid-guided nuclease, the first region of the blocked nucleic acid molecule includes a nuclease-resistant DNA sequence, and the second region of the blocked nucleic acid molecule includes a cleavable DNA sequence. In other embodiments, when the Cas enzyme in RNP1 is a Cas RNA-guided DNA nucleic acid-guided nuclease and the Cas enzyme in RNP2 is a Cas RNA-guided RNA nucleic acid-guided nuclease, the first region of the blocked nucleic acid molecule includes a nuclease-resistant RNA sequence, and the second region of the blocked nucleic acid molecule includes a cleavable DNA sequence and a cleavable RNA sequence. In yet other embodiments, when the Cas enzyme in RNP1 is a Cas RNA-guided RNA nucleic acid-guided nuclease and the Cas enzyme in RNP2 is a Cas RNA-guided DNA nucleic acid-guided nuclease, the first region of the blocked nucleic acid molecule includes a nuclease-resistant DNA sequence, and the second region of the blocked nucleic acid molecule includes a cleavable DNA sequence and a cleavable RNA sequence. In some other embodiments, when the Cas enzyme in both RNP1 and RNP2 is a Cas RNA-guided RNA nucleic acid-guided nuclease, the first region of the blocked nucleic acid molecule includes a nuclease-resistant RNA sequence, and the second region of the blocked nucleic acid molecule includes a cleavable RNA sequence. Note, however, as stated above, the nucleic acid-guided nucleases (i.e., Cas enzymes) in RNP1 and RNP2 must be different.

The Dimerization Screening Assay Employing Blocked Primer Molecules

The blocked nucleic acids described above may also include blocked primer molecules. Blocked primer molecules include a sequence complementary to a primer binding domain (PBD) on a template molecule (see description below in reference to FIGS. 4A and 4B) and can have the same general structures as the blocked nucleic acid molecules described above. A PBD serves as a nucleotide sequence for primer hybridization followed by primer polymerization by a polymerase. In any of Formulas I, II, or III described above, the blocked primer nucleic acid molecule may include a sequence complementary to the PBD on the 5' end of T. The unblocked primer nucleic acid molecule can bind to a template molecule at the PBD and copy the template molecule via polymerization by a polymerase.

Figure 4A:
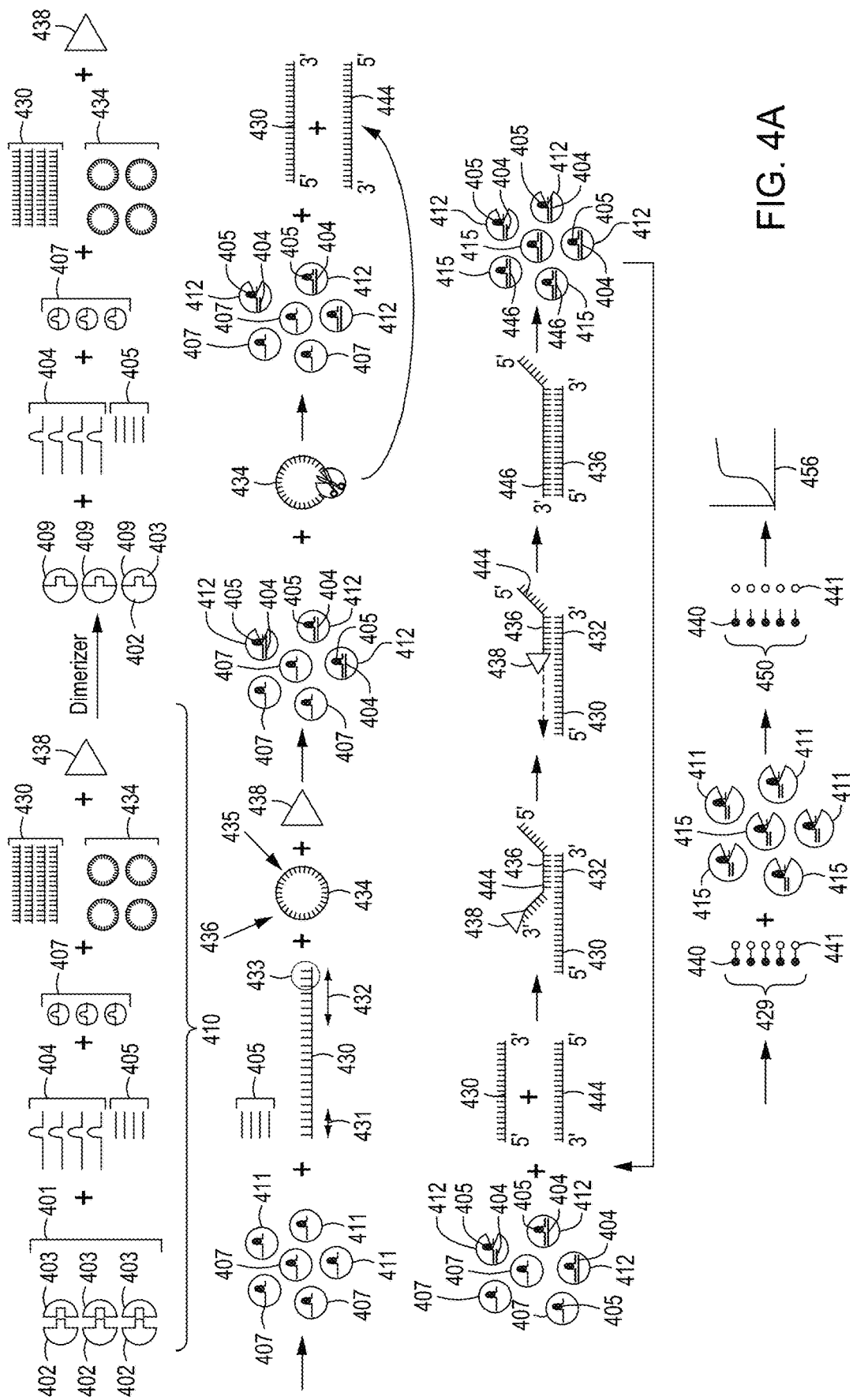
FIG. 4A is a diagram showing the sequence of steps in an exemplary dimerization screening assay involving a split Cas enzyme and circular blocked primer molecules and linear template molecules, according to certain embodiments.
Figure 4B:
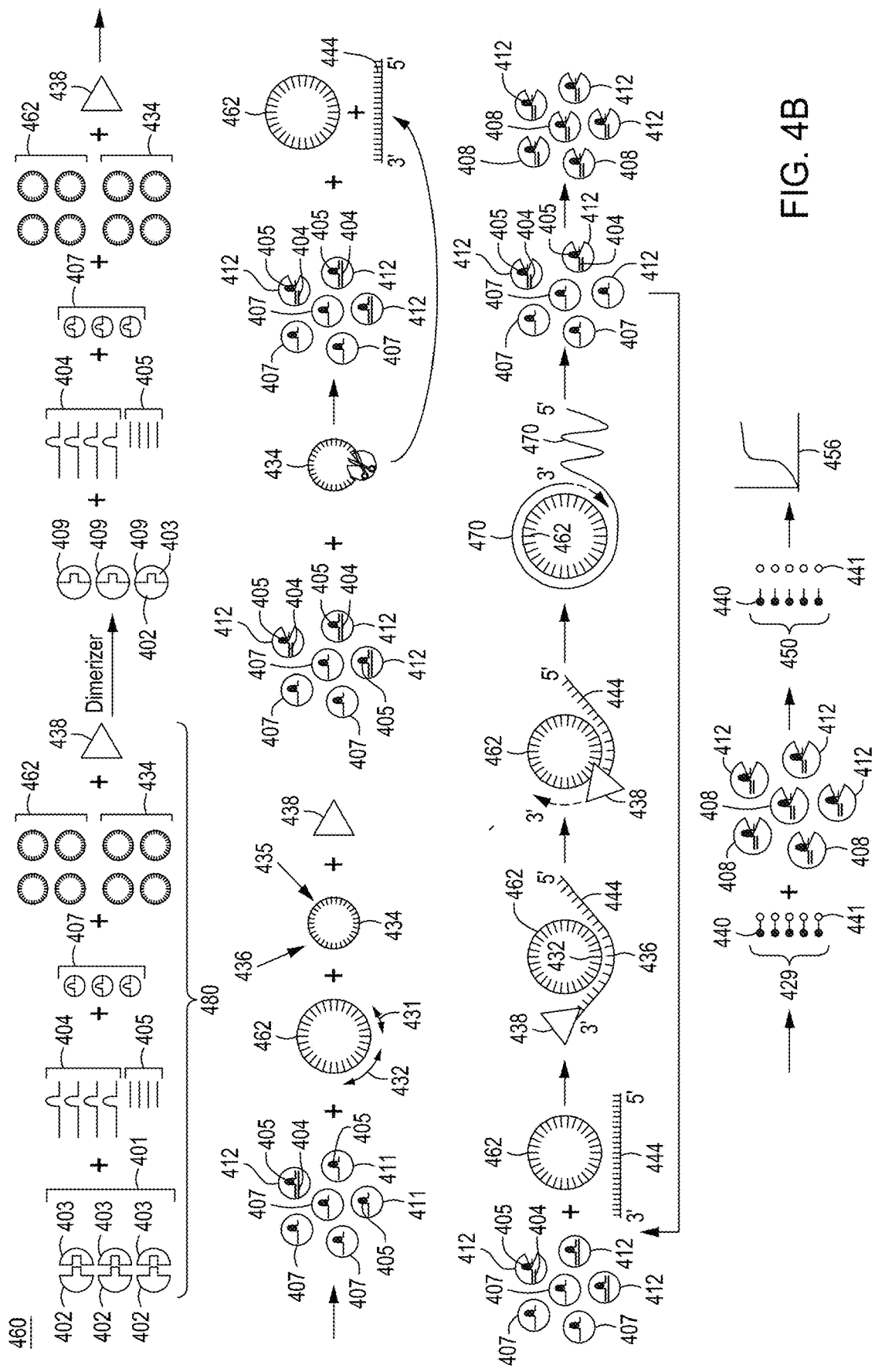
FIG. 4B is a diagram showing the sequence of steps in an exemplary dimerization screening assay involving a split Cas enzyme and circular blocked primer molecules and circular template molecules, according to certain embodiments.

Specific embodiments of the cascade assay that utilize blocked primer molecules are depicted in FIGS. 4A and 4B. In the embodiments using blocked nucleic acid molecules described above, activation of RNP1 and trans-cleavage of the blocked nucleic acid molecules were used to activate RNP2— that is, the unblocked nucleic acid molecules are a target sequence for the gRNA in RNP2. In contrast, in the embodiments using blocked primers to activate RNP1, trans-cleavage unblocks a blocked primer molecule that is then used to prime a template molecule for extension by a polymerase, thereby synthesizing activating nucleic acids that are the target sequence for the gRNA in RNP2.

FIG. 4A is a diagram showing a sequence of steps in an exemplary dimerization screening assay 400 involving circular blocked primer molecules and linear template molecules. In this embodiment, a blocked primer molecule is used to prevent the activation of RNP2 in the absence of a dimerization event. The dimerization screening assay 400 in FIG. 4A begins with providing the cascade assay components in a reaction mix 410 comprising: 1) dimerizer/N-terminal portion of split Cas enzyme 402; 2) dimerizer/C-terminal portion of split Cas enzyme 403 (i.e., the di-N-term 402 and di-C-term 403 cascade assay components 401); 3) first guide nucleic acids (gRNA1) 404; 4) RNP1 activating nucleic acids 405; 5) RNP2s 407; 6) linear template molecules 430 (which is the non-target strand); 7) circular blocked primer molecules 434; 8) a polymerase 438; and 9) reporter moieties 429 (only shown at the bottom of FIG. 4A). The RNP2s comprise gRNA2s that are specific for synthesized activating nucleic acids resulting from unblocking and copying the blocked primer molecules, and a second, intact nuclease (e.g., Cas 12a or Cas 14 for a DNA unblocked primer molecule or a Cas 13a for an RNA unblocked primer molecule). The split Cas enzyme that, if reconstituted, will form RNP1 with gRNA1 and the second, intact Cas enzyme in RNP2 must be different. The Cas enzymes in RNP1 and RNP2 must also, when activated, have trans-cleavage activity following binding of an RNP1 activating nucleic acid or synthesized activating nucleic acid, respectively.

In a first step, a dimerization event takes place, bringing the di-N-term 402 and di-C-term 403 portions of the split Cas enzyme together, thereby reconstituting a functional first Cas enzyme 409. The functional first Cas enzyme 409 is now in the reaction mix with the first guide nucleic acids (gRNA1) 404, RNP1 activating nucleic acids 405, RNP2s 407, linear template molecules 430, circular blocked primer molecules 434, and polymerase 438. The functional first Cas enzyme 409 now can complex with gRNA1 404 to form RNP1 411; also seen are RNP1 activating nucleic acids 405, RNP2s 407, linear template molecules 430 (only one is shown), circular blocked primer molecules 434 (only one is shown), and polymerase 438. The linear template molecules 430 (non-target strand) comprise a PAM sequence 431, a primer binding domain (PBD) 432 and, optionally, a nucleoside modification 433 to protect the linear template molecule 430 from 3'→5' exonuclease activity. Blocked primer molecule 434 comprises a cleavable region 435 and a complement 436 to the PBD 432 on the linear template molecule 430. In a next step, the RNP1s 411 complex with RNP1 activating nucleic acids 405 to form activated RNP1s 412.

Once activated, RNP1 412 cuts the RNP1 activating nucleic acids 405 via sequence specific cis-cleavage, and trans-cleavage of other nucleic acids present in the reaction mix is initiated as well, including at least one of the blocked primer molecules 434. The circular blocked primer molecule 434, upon cleavage, becomes an unblocked linear primer molecule 444, which has a region 436 complementary to the PBD 432 on the linear template molecule 430 and can bind to the linear template molecule 430.

Once the unblocked linear primer molecule 444 and the linear template molecule 430 are hybridized (i.e., hybridized at the PBD 432 of the linear template molecule 430 and the PBD complement 436 on the unblocked linear primer molecule 444), 3'→5' exonuclease activity of the polymerase 438 removes the unhybridized single-stranded DNA at the end of the unblocked primer molecule 444 and the polymerase 438 can copy the linear template molecule 430 to produce synthesized activating molecule 446, which is a complement of the non-target strand, which thus is the target strand. The synthesized activating molecule 446 is capable of activating RNP2 (407→415). As described above, because the nucleic acid-guided nuclease in the RNP2 407 complex exhibits (that is, possesses) both cis- and trans-cleavage activity, more blocked primer molecules 434 become unblocked primer molecules 444, triggering activation of more RNP2s 407 and more trans-cleavage activity in a cascade.

FIG. 4A at bottom depicts the concurrent activation of reporter moieties. Intact reporter moieties 429 comprise a quencher 440 and a fluorophore 441. As described above in relation to FIG. 1, the reporter moieties are also subject to trans-cleavage by activated RNP1 412 and RNP2 415. The intact reporter moieties 429 become activated reporter moieties 450 when the quencher 440 is separated from the fluorophore 441, and the fluorophore emits a fluorescent signal 456. Signal strength increases rapidly as more blocked primer molecules 434 become unblocked primer molecules 444 generating synthesized activating nucleic acids 446 and triggering activation of more RNP2 415 complexes and more trans-cleavage activity of the reporter moieties 429. Again, here the reporter moieties are shown as separate molecules from the blocked nucleic acid molecules, but other configurations may be employed and are discussed in relation to FIG. 6. As stated above, a particularly advantageous feature of the present dimerization screening assay is that, with the exception of the putative dimerizers that are fused to the N-terminal and C-terminal portions of the split Cas enzyme, the dimerization screening assay components can be the same in each assay no matter what putative binding pairs of interest are being detected, making the dimerization screening assay easily reprogrammable.

FIG. 4B is a diagram showing the sequence of steps in an exemplary dimerization screening assay involving circular blocked primer molecules and circular template molecules. The dimerization screening assay of FIG. 4B differs from that depicted in FIG. 4A by the configuration of the template molecule. Where the template molecule in FIG. 4A was linear, in FIG. 4B the template molecule is circular. The dimerization screening assay 460 in FIG. 4B begins with providing the cascade assay components in a reaction mix 480 comprising: 1) dimerizer/N-terminal portion of split Cas enzyme 402; 2) dimerizer/C-terminal portion of split Cas enzyme 403 (i.e., the di-N-term 402 and di-C-term 403 cascade assay components 401); 3) first guide nucleic acids (gRNA1) 404; 4) RNP1 activating nucleic acids 405; 5) RNP2s 407; 6) circular template molecules 462 (which is the non-target strand); 7) circular blocked primer molecules 434; 8) a polymerase 438; and 9) reporter moieties 429 (seen at the bottom of FIG. 4B). The RNP2s comprise gRNA2s that are specific for synthesized activating nucleic acids resulting from unblocking and copying the blocked primer molecules, and a second, intact nuclease (e.g., Cas 12a or Cas 14 for a DNA unblocked primer molecule or a Cas 13a for an RNA unblocked primer molecule). The split Cas enzyme that, if reconstituted, will form RNP1 with gRNA1 and the second, intact Cas enzyme in RNP2 must be different. The Cas enzymes in RNP1 and RNP2 must also, when activated, exhibit trans-cleavage activity.

In a first step, a dimerization event takes place, bringing the di-N-term 402 and di-C-term 403 portions of the split Cas enzyme together, thereby reconstituting a functional first Cas enzyme 409. The functional first Cas enzyme 409 is in the reaction mix with the first guide nucleic acids (gRNA1) 404, RNP1 activating nucleic acids 405, RNP2s 407, circular template molecules 462, circular blocked primer molecules 434, and polymerase 438. The functional first Cas enzyme 409 now complexes with gRNA1 404 to form RNP1 411; also seen are RNP1 activating nucleic acids 405, RNP2s 407, circular template molecules 462 (only one is shown), circular blocked primer molecules 434 (only one is shown), and polymerase 438. The circular template molecule 462 (non-target strand) comprises a PAM sequence 431 and a primer binding domain (PBD) 432. Due to the circular configuration of the template molecules, 3'→5' exonuclease activity is essentially prevented. Blocked primer molecules 434 comprise a cleavable region 435 and a complement 436 to the PBD 432 on the circular template molecule 462. In a next step, the RNP1s 411 complex with RNP1 activating nucleic acids 405 to form activated RNP1s 412.

Once activated, RNP1 412 cuts the RNP1 activating nucleic acids 405 via sequence specific cis-cleavage, and trans-cleavage of other nucleic acids present in the reaction mix is initiated as well, including at least one of the blocked primer molecules 434. The circular blocked primer molecule 434, upon cleavage, becomes an unblocked linear primer molecule 444, which has a region 436 complementary to the PBD 432 on the circular template molecule 462 and can bind to the circular template molecule 462.

Once the unblocked linear primer molecule 444 and the circular template molecule 462 are hybridized (i.e., hybridized at the PBD 432 of the circular template molecule 462 and the PBD complement 436 on the unblocked linear primer molecule 444), 3'→5' exonuclease activity of the polymerase 438 removes the unhybridized single-stranded DNA at the end of the unblocked primer molecule 444. The polymerase 438 can now use the circular template molecule 462 (non-target strand) to produce concatenated synthesized activating nucleic acid molecules 470 — which are concatenated target strands that will be cleaved by the trans-cleavage activity of activated RNP1. The cleaved regions of the concatenated synthesized activating nucleic acids 470 (target strand) are capable of activating the RNP2 (407→408) complex.

As described above, because the nucleic acid-guided nuclease in the RNP2 408 complex exhibits (that is, possesses) both cis- and trans-cleavage activity, more blocked primer molecules 434 become unblocked primer molecules 444, thereby triggering activation of more RNP2s 407 and more trans-cleavage activity in a cascade.

FIG. 4B at bottom depicts the concurrent activation of reporter moieties. Intact reporter moieties 429 comprise a quencher 440 and a fluorophore 441. As described above in relation to FIG. 1, the reporter moieties are also subject to trans-cleavage by activated RNP1 408 and RNP2 412. The intact reporter moieties 429 become activated reporter moieties 450 when the quencher 440 is separated from the fluorophore 441, and the fluorophore emits a fluorescent signal 456. Signal strength increases rapidly as more blocked primer molecules 434 become unblocked primer molecules 444, in turn generating synthesized activating nucleic acids 470 and triggering activation of more RNP2 412 complexes and more trans-cleavage activity of the reporter moieties 429. Again, here the reporter moieties are shown as separate molecules from the blocked nucleic acid molecules, but other configurations may be employed and are discussed in relation to FIG. 6. As stated above, a particularly advantageous feature of the present dimerization screening assay is that, with the exception of the putative dimerizers that are fused to the N-terminal and C-terminal portions of the split Cas enzyme, the dimerization screening assay components can be the same in each assay no matter what putative binding pairs of interest are being detected.

The polymerases used in the "blocked primer molecule" embodiments serve to polymerize a reverse complement strand of the template molecule (non-target strand) to generate synthesized activating nucleic acids (target strand) as described above. In some aspects of the embodiments employing blocked primer molecules, the polymerase is a DNA polymerase, such as a BST, T4, or Therminator polymerase (New England BioLabs Inc., Ipswich MA., USA). In some aspects of the embodiments employing blocked primer molecules, the polymerase is a Klenow fragment of a DNA polymerase. In some aspects of the embodiments employing blocked primer molecules the polymerase is a DNA polymerase with 5'→3' DNA polymerase activity and 3'→5' exonuclease activity, such as a Type I, Type II, or Type III DNA polymerase. In some aspects of the embodiments employing blocked primer molecules, the DNA polymerase, including the Phi29, T7, Q5®, Q5U®, Phusion®, OneTaq®, LongAmp®, Vent®, or Deep Vent® DNA polymerases (New England BioLabs Inc., Ipswich MA., USA), or any active portion or variant thereof. Also, a 3' to 5' exonuclease can be separately used if the polymerase lacks this activity.

The Dimerization Screening Assay Employing Blocked Guide (gRNA) Molecules

Figure 5A:
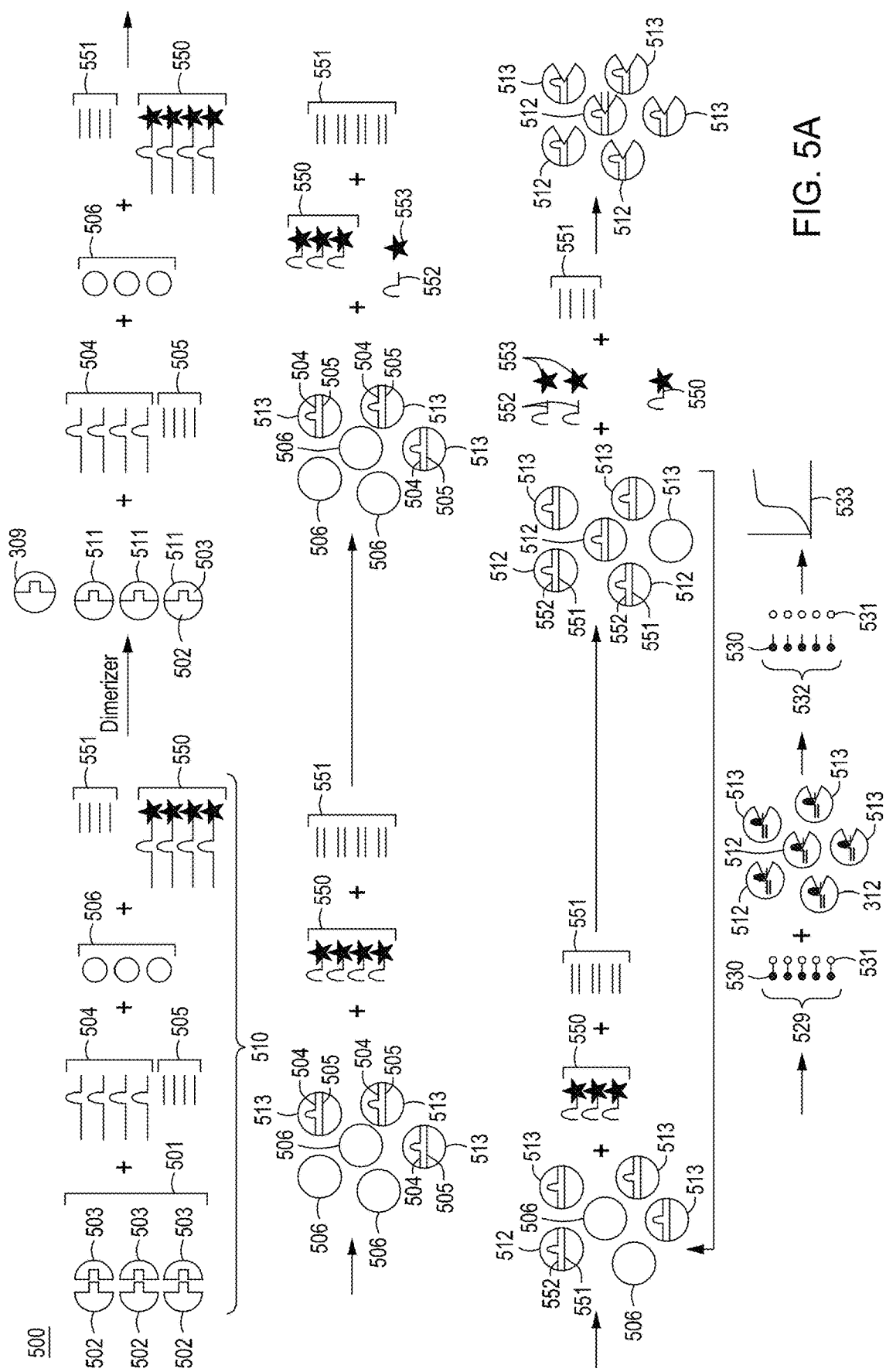
FIG. 5A is a diagram showing the sequence of steps in an exemplary dimerization screening assay utilizing a split Cas enzyme and blocked guide nucleic acid (gRNA) molecules, according to certain embodiments.

FIG. 5A is a diagram showing the sequence of steps in an exemplary dimerization screening assay utilizing a split Cas enzyme and blocked guide nucleic acid (gRNA) molecules. In this embodiment, instead of a blocked nucleic acid molecule or a blocked primer molecule, a blocked guide molecule (i.e., a blocked guide RNA or blocked gRNA) complementary to an RNP2 activating nucleic acid and complexed with a second nucleic acid-guided nuclease is used to form RNP2. The blocked guide molecule functions like the blocked nucleic acid molecules and the blocked primer molecules to "lock" RNP2 unless and until the N-terminal and C-terminal portions of the split Cas enzyme are brought into functional proximity by a dimerization event and activate RNP1. The trans-cleavage activity of RNP1 then unblocks the blocked guide molecules which can then complex with the second nucleic acid-guided nuclease to form second ribonucleoprotein complexes (i.e., RNP2s) which can then be activated.

FIG. 5A is a diagram showing the sequence of steps in an exemplary dimerization screening assay involving blocked guide molecules. In this embodiment, a blocked guide molecule is used to prevent the activation of RNP2 in the absence of a dimerization event. The dimerization screening assay 500 in FIG. 5A begins with providing the cascade assay components in a reaction mix 510 comprising: 1) dimerizer/N-terminal portion of split Cas enzyme 502; 2) dimerizer/C-terminal portion of split Cas enzyme 503 (i.e., the di-N-term 502 and di-C-term 503 cascade assay components 501); 3) first guide nucleic acids (gRNA1) 504; 4) RNP1 activating nucleic acids 505; 5) intact second Cas enzyme 506; 6) RNP2 activating nucleic acids 551; 7) blocked guide molecules (blocked gRNA2s) 550; and 8) reporter moieties 529 (seen only at bottom of FIG. 5A). The RNP2s that will be formed as a result of a dimerization event comprise unblocked gRNA2s that are specific for the RNP2 activating nucleic acids 551 and the second, intact Cas enzyme 506 (e.g., Cas 12a or Cas 14 for DNA RNP2 activating nucleic acids or, e.g., a Cas 13a for RNA RNP2 activating nucleic acids). The split Cas enzyme that, if reconstituted, will form RNP1 with gRNA1 and the second, intact Cas enzyme in RNP2 must be different, and the Cas enzymes in RNP1 and RNP2 must, when activated, have trans-cleavage activity following initiation of cis-cleavage activity.

In a first step, a dimerization event takes place, bringing the di-N-term 502 and di-C-term 503 portions of the split Cas enzyme together, thereby reconstituting a functional first Cas enzyme 511. The functional first Cas enzyme 511 is now in the reaction mix with the first guide nucleic acids (gRNA1) 504, RNP1 activating nucleic acids 505, intact second Cas enzyme 506, RNP2 activating nucleic acids 551, and blocked guide molecules 550. The functional first Cas enzyme 511 now can internalize gRNA1 504 to form RNP1 513, which then complexes with RNP1 activating nucleic acids 505 and activates cis-cleavage of the RNP1 activating nucleic acids 505. Also seen are intact second Cas enzyme 506, blocked guide molecules (blocked gRNA2s) 550, and RNP2 activating nucleic acids 551.

Once cis-cleavage of the RNP1 activating nucleic acids occurs due to binding of the RNP1 activating nucleic acids 505, indiscriminate trans-cleavage activity of other nucleic acids in the reaction mix is initiated as well, including at least one of the blocked gRNA2s 550. The blocked gRNA2s (i.e., a high $K_d$ molecules, where high $K_d$ relates to binding to the RNP2 activating nucleic acids 551), upon cleavage, become unblocked gRNA2s 552 (a low $K_d$ molecule, where low $K_d$ relates to binding to the RNP2 activating nucleic acids 551). Thus, at least one of the blocked gRNA2s 550 becomes an unblocked gRNA2 552 when the blocking moiety 553 is removed from the blocked gRNA2 550. As described above, "blocking moiety" may refer to nucleoside modifications, topographical configurations such as secondary structures, and/or structural modifications.

Once at least one of the blocked gRNA2s 550 is unblocked, the unblocked gRNA2 551 can then interact with intact second Cas enzyme 506 to form RNP2 512, which then complexes with RNP2 activating nucleic acids 551 and cleaves the RNP2 activating nucleic acids via cis-cleavage, thereby triggering trans-cleavage of more nucleic acids in the reaction mix 510. Because the nucleic acid-guided nucleases in the activated RNP1s 513 and RNP2s 512 have both cis- and trans-cleavage activity, the trans-cleavage activity causes more blocked gRNA2s 550 to become unblocked gRNA2s 551, triggering activation of even more RNP2s 512 and more trans-cleavage activity in a reaction cascade.

FIG. 5A at bottom depicts the concurrent activation of reporter moieties.

Intact reporter moieties 529 comprise a quencher 530 and a fluorophore 531 linked by a nucleic acid sequence. As described above in relation to FIG. 1, the intact reporter moieties 529 are also subject to trans-cleavage by activated RNP1 513 and RNP2 512. The intact reporter moieties 529 become activated reporter moieties 532 when the quencher 530 is separated from the fluorophore 531, emitting a fluorescent signal 533. Signal strength increases rapidly as more blocked gRNA2s 550 become unblocked gRNA2s 511, triggering cis-cleavage activity of more RNP2s 512 and thus more trans-cleavage activity of the reporter moieties 529. Again, the reporter moieties are shown here as separate molecules from the blocked nucleic acid molecules, but other configurations may be employed and are discussed in relation to FIG. 6. In this embodiment as with the other embodiments described above, a particularly advantageous feature of the dimerization screening assay is that, with the exception of the putative dimerizers that are fused to the N-terminal and C-terminal portions of the split Cas enzyme, the dimerization screening assay components are the same in each assay no matter what putative binding pairs of interest are being detected.

Figure 5B:
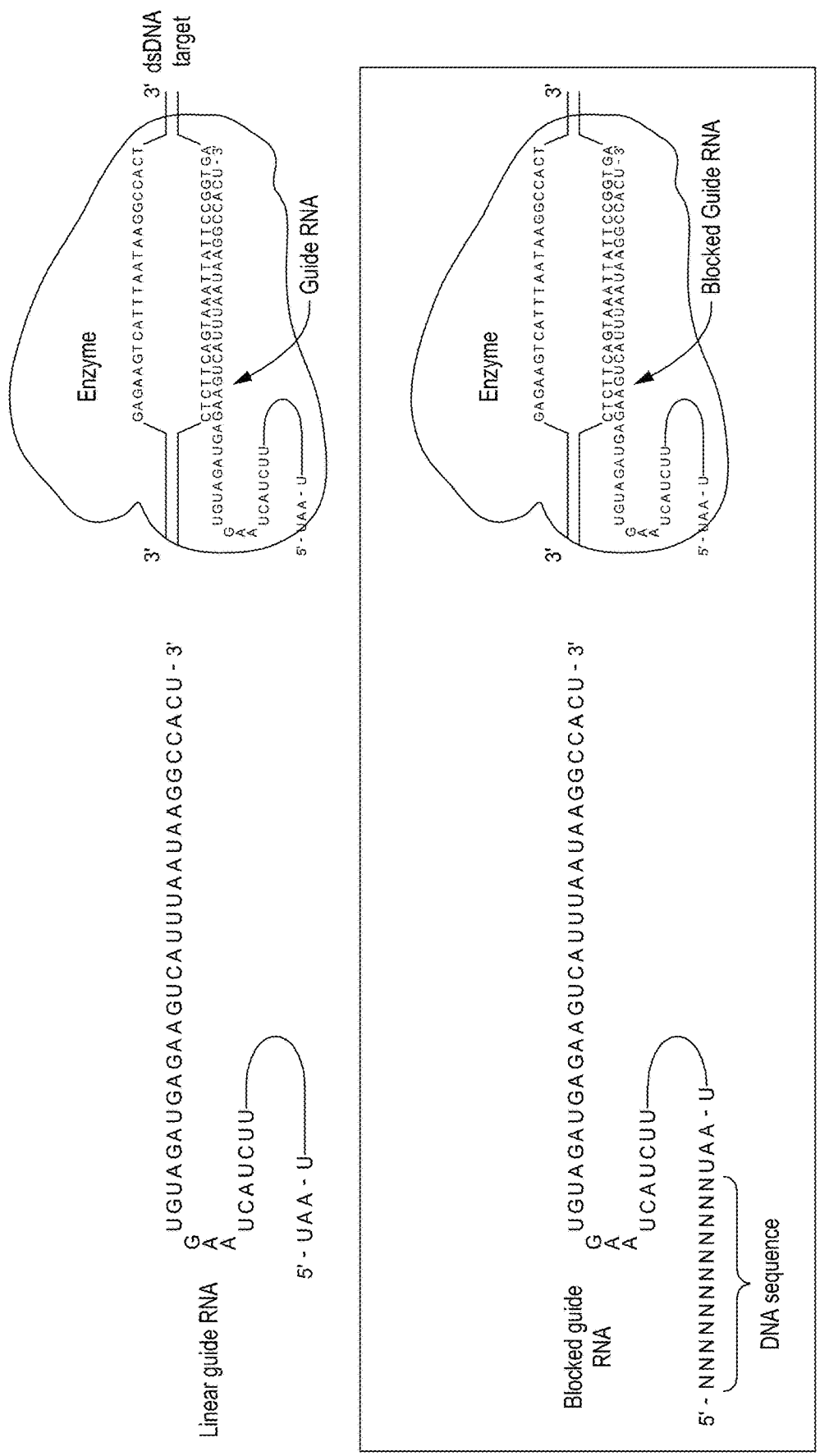
FIG. 5B shows an exemplary guide RNA design and an exemplary blocked guide RNA design, according to certain embodiments.

FIG. 5B shows exemplary guide RNA designs; UAAUUUCUACUAAGUGUAGAUGAGAAGUCAUUU-AAUAAGGCCACU is SEQ ID NO: 6; GAGAAGTCATT-TAATAAGGCCACT is SEQ ID NO: 7; CTCTTCAGTAAATTATTCCGGTGA is SEQ ID NO: 8; NNNNNNNNNNNUAUUUCUACUAAGUGUAGAUG-AGAGUCAUUUAAUAAGGC CACU is SEQ ID NO: 9; and NNNNNNNNUAAUUUCUACUAAGUGUAGAUG-AGAAGUCAUUUAAUAAGGCC ACU is SEQ ID NO: 10.

Figure 5C:
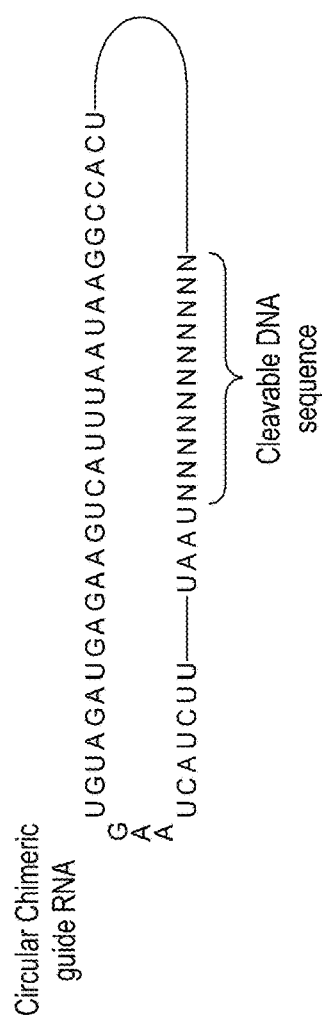
FIG. 5C shows exemplary blocked guide RNAs, both linear and circular, according to certain embodiments.
Figure 5C:
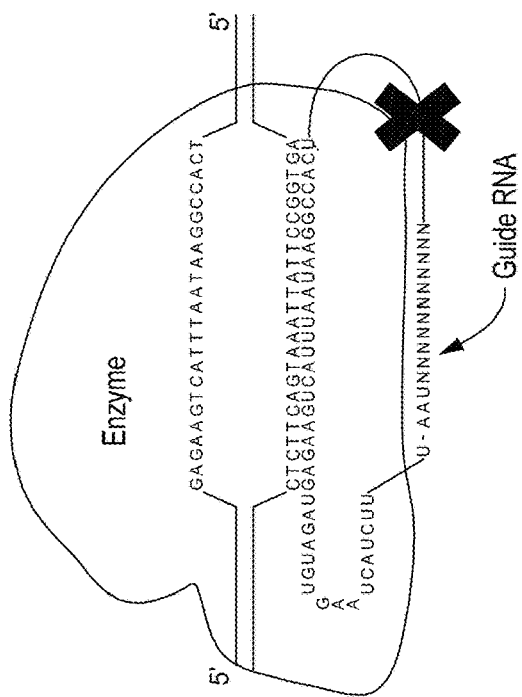

FIG. 5C shows blocked guide RNAs, both linear and circular. The black lines show one phosphate linkage shown only for visualization of circular molecules; GAGAAGT-CATTTAATAAGGCCACT is SEQ ID NO: 7; CTCTTCAGTAAATTATTCCGGTGA is SEQ ID NO: 8; and NNNNNNNNNNNUAAUUUCUACUAAGUGUA-GAUGAGAAGUCAUUUAAUAAG GCCACU is SEQ ID NO: 11.

Reporter Moiety Configurations

Figure 6:
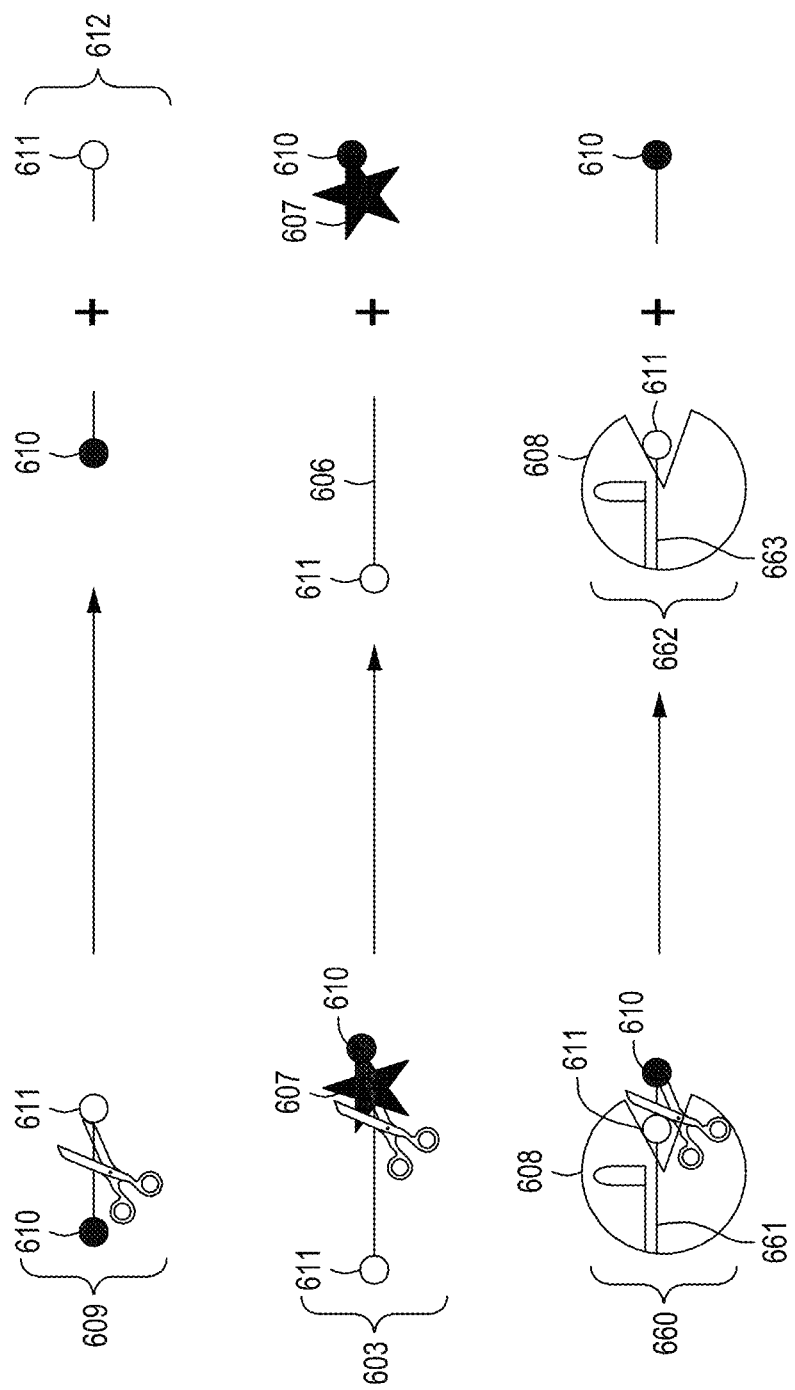
FIG. 6 illustrates three embodiments of reporter moieties.

FIG. 6 depicts three exemplary mechanisms in which a cascade assay reaction can release a signal from a reporter moiety. FIG. 6 at top shows the mechanism discussed in relation to FIGS. 3A, 4A, 4B, and 5A. In this embodiment, a reporter moiety 609 is a separate molecule from the blocked nucleic acid molecules present in the reaction mix. Reporter moiety 609 comprises a quencher 610 and a fluorophore 611. An activated reporter moiety 612 emits a signal from the fluorophore 611 once it has been physically separated from the quencher 610.

FIG. 6 at center shows a blocked nucleic acid molecule 603, which is also a reporter moiety. In addition to quencher 610 and fluorophore 611, a blocking moiety 607 can be seen. Blocked nucleic acid molecule/reporter moiety 603 comprises the quencher 610 and the fluorophore 611. In this embodiment of the cascade assay, when the blocked nucleic acid molecule 603 is unblocked due to trans-cleavage initiated by the target nucleic acid of interest binding to RNP1, the unblocked nucleic acid molecule 606 also becomes an activated reporter moiety with fluorophore 611 separated from quencher 610. Note both the blocking moiety 607 and the quencher 610 are removed. In this embodiment, reporter signal is directly generated as the blocked nucleic acid molecules become unblocked. Embodiments of this schema can be used to supply the bulky modifications to the blocked nucleic acid molecules described below.

FIG. 6 at the bottom shows that cis-cleavage of an unblocked nucleic acid molecule or a synthesized activating molecule at a PAM distal sequence by RNP2 generates a signal. Shown are activated RNP2 608, unblocked nucleic acid molecule 661, quencher 610, and fluorophore 611 forming an activated RNP2 with the unblocked nucleic acid/reporter moiety intact 660. Cis-cleavage of the unblocked nucleic acid/reporter moiety 661 results in an activated RNP2 with the reporter moiety activated 662, comprising the activated RNP2 608, the unblocked nucleic acid molecule with the reporter moiety activated 663, quencher 610, and fluorophore 611. Embodiments of this schema also can be used to supply the bulky modifications to the blocked nucleic acid molecules described below, and in fact a combination of the configurations of reporter moieties shown in FIG. 6 at center and at bottom may be used.

Instrumentation to Enable Massive Multiplexing of the Dimerization Screening Assay The dimerization screening assays described herein may be performed in virtually any partitioned format, including plates with wells or other partitions, or, in one attractive embodiment, in droplets. Microfluidic droplet generation using two immiscible fluids (e.g., an aqueous solution and an oil) that meet at intersecting microchannels with droplets being generated at a junction between the two microfluidic channels has been known in the art for several decades. The terms "droplet" and "emulsion" are used interchangeably herein to refer to an aliquot of one fluid (here, an aqueous solution) in an immiscible carrier fluid (e.g., an oil), with the carrier fluid substantially surrounding the aqueous droplet, thereby forming a partition or "mini-reactor" in which to execute the dimerization screening assay reactions. For example, in 1984 Shaw Stewart taught the use of a device to produce microfluidic emulsion droplets from two immiscible fluids that meet at an intersecting channel. (See UK Patent Application No. 2097692 to Shaw Stewart.) Shaw Stewart introduced the concept of a microfluidic "T-junction" at which droplets of an aqueous solution can be formed using a continuously flowing immiscible "carrier phase." By the 1990s, various groups were looking to both miniaturize and automate biological and chemical reactions and by the early 2000s research groups had shown proof of principle for the use of aqueous droplets in an oil carrier for carrying out various analyses, cell sorting operations and biochemical reactions including PCR. (See, e.g., US Pub. No. 2002/0058332 to Quake, et al.)

The immiscible fluids used in the microchannels may be provided by on-chip wells or off-chip reservoirs and the microchannels intersect as T-junctions to form the droplets. A pressure differential is used to control the flow of the fluids at the T-junction, shearing-off the aqueous fluid into the immiscible oil flow to create droplets. By adjusting the pressure of the flowing fluids, a pressure difference can be established to shear off droplets of the aqueous solution at a regular frequency as the aqueous solution enters the oil stream, thereby forming droplets in the oil stream.

In the 2000s a "cross junction" strategy was introduced. In the cross-junction approach, aqueous droplets are formed at converging flows of the immiscible fluid where a continuous phase (here, the oil phase) and the aqueous phase converging flows "pinch" off the droplets of the aqueous phase at a droplet-forming junction. This "flow focusing" approach, in which the aqueous droplet is focused by the oil phase at the cross junction, is described, for example, by Higuchi, et al. (US Pat. Pub. 2004/0068019) Microfluidic devices or "chips" are available commercially through, e.g., microfluidic ChipShop™ GmbH (Jena, Germany); uFluidix™ (Toronto, Canada); Microflexis™ (Hamburg, Germany); and microLIQUID™ (Gipuzkoa, Spain).

Performing the dimerization screening assay in droplets is particularly useful for screening massive numbers of putative dimerizers. Allocating individual molecules, i.e., Poisson distribution of molecules, in droplets is accomplished by introducing an aqueous stream comprising the molecules into a flowing stream of a carrier fluid such that droplets are generated at the junction of the two streams. By providing the aqueous molecule-containing stream at a certain concentration level and speed, the number of droplets containing molecules can be controlled. In the present methods, it is desirable to control the relative flow rates of the aqueous and non-aqueous fluid such that, on average, the droplets contain less than one molecule (here, putative dimerizer/N- or C-terminal fusion) per droplet to ensure that any one droplet will comprise either one molecule or no molecule. Thus, the droplet method allows one to partition a single putative dimerizer (or bead comprising many copies of a single putative dimerizer).

Figure 7:
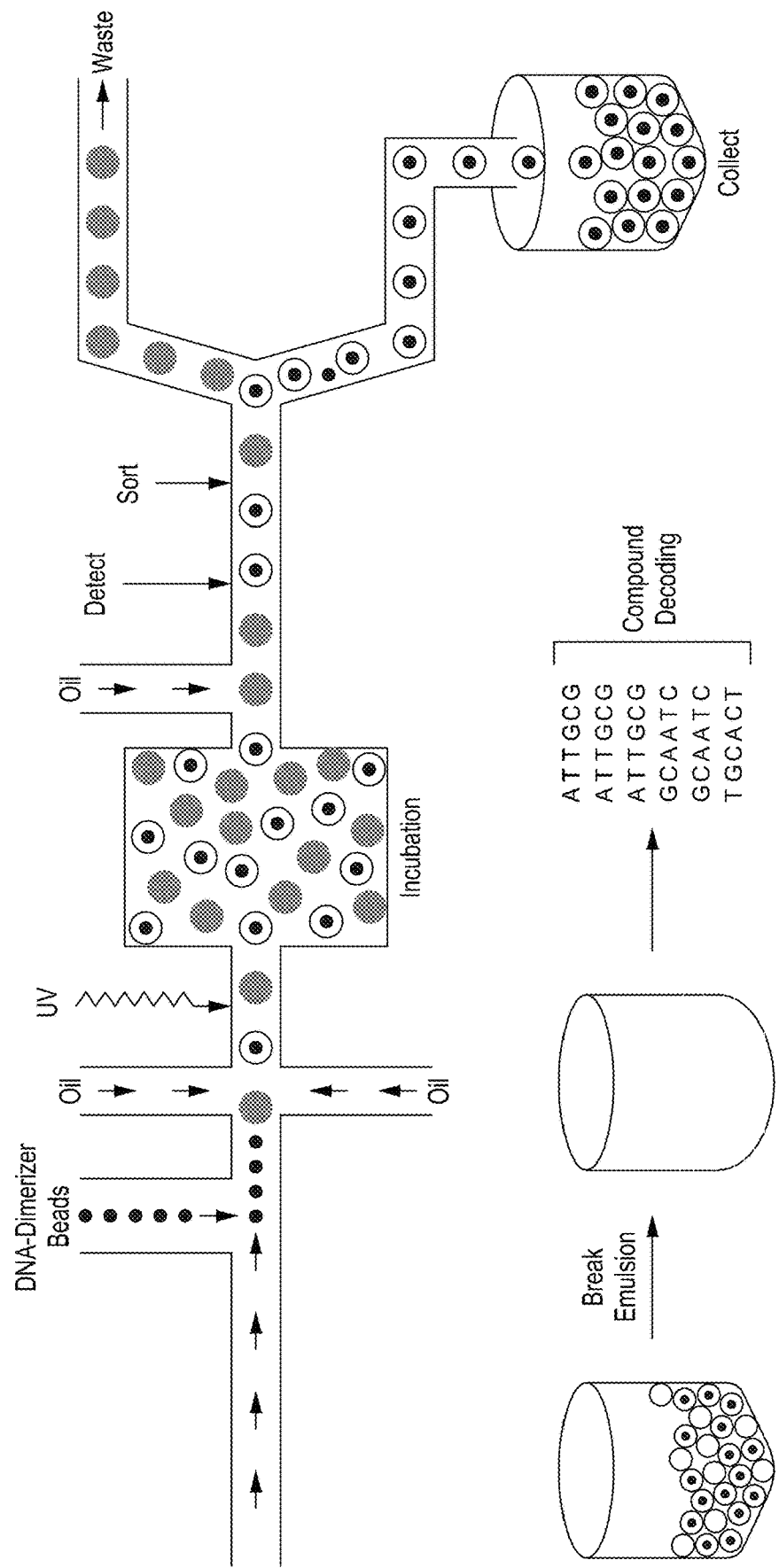
FIG. 7 shows a representation of an exemplary microfluidic system for performing the dimerization screening assay in a massively multiplexed format, according to certain embodiments.

FIG. 7 is a representation of an exemplary microfluidic system for performing the dimerization screening assay in a massively multiplexed format using DNA-encoded beads. The microfluidic system carries out putative dimerizer/C-terminal fusion molecule bead distribution into picoliter-sized reagent droplets. Starting at left, an aqueous fluid comprising a reaction mix flows through a microfluidic channel. The reaction mix will vary depending on which of the three embodiments of the dimerization screening assay is employed; that is, whether blocked nucleic acid molecules, blocked primer molecules or blocked guide RNAs are employed. The reaction mix that flows in a stream from the left of FIG. 7 contains all components for the reaction except for the library of putative dimerizer/C-terminal fusion molecules.

The putative dimerizer/C-terminal fusion molecules are partitioned and coupled to DNA-encoded beads, where each DNA-encoded bead is first linked to a photolabile (or other cleavable) linker, then to a unique DNA sequence which serves as a "compound code" for the putative dimerizer/C-terminal fusion molecule and finally to the putative dimerizer/C-terminal fusion molecule itself. After the DNA beads are loaded with each member of the library of putative dimerizer/C-terminal fusion molecules, the loaded DNA beads are pooled, and then are introduced into the aqueous flow of the reaction mix. Moving right in FIG. 7, oil (the "carrier fluid") is then introduced from perpendicular channels (here, above and below the main flow channel) in a "flow focusing" configuration, which "pinches off" aqueous droplets into the flow of the oil. Each aqueous droplet will comprise reaction mix, but, if the flow of the library of putative dimerizers and the flow of the aqueous fluid comprising the reaction mix is controlled, in some aspects only approximately half of the aqueous droplets will comprise a DNA bead with linked putative dimerizer/C-terminal fusion molecules, in other aspects, because beads are in the form of a packed bed, the beads can be loaded to achieve super poisson distribution where >90% of the droplets contain a bead. By using this microfluidic approach, droplets are generated that form a reaction partition for each of the putative dimerizer/C-terminal fusion molecules in the dimerization screening assay.

The aqueous droplets with loaded beads (and without loaded beads) proceed through the flow channel and are subjected to photochemical cleavage (UV zap) of the putative dimerizer/C-terminal fusion molecule from the bead. Separating the putative dimerizer/C-terminal fusion molecules from the beads frees the putative dimerizer/C-terminal fusion molecules coupled to the nucleic acid compound tag from linkage to the bead, freeing the putative dimerizer/C-terminal fusion molecule to dimerize with the first dimerizer/N-terminal fusion molecule.

Moving right in FIG. 7, the droplets are incubated at a temperature appropriate for a dimerization event, and if a dimerization event occurs the N-terminal portion of the split Cas enzyme and the C-terminal portion of the split Cas enzyme are brought into proximity, the split Cas enzyme forms RNP 1 with gRNA1, and cis- and trans-cleavage of the split Cas enzyme is reconstituted. Once RNP1 is formed, the RNP1 activating nucleic acid can be internalized into RNP1 and cis-cleavage of the RNP1 activating nucleic acid occurs, triggering indiscriminate trans-cleavage activity of other nucleic acids in the reaction mix. The other nucleic acids in the reaction mix will differ depending on the embodiment of the dimerization assay used, but will include blocked nucleic acid molecules, blocked primer molecules, or blocked guide molecules. Unblocking of blocked molecules initiates cis-cleavage activity of RNP2 and subsequent trans-cleavage activity, which in turn initiates cleavage of reporter moieties in the reaction mix in a cascade.

After incubation, the aqueous droplets continue to flow through the microfluidic system. Additional oil is flowed into the existing oil flow to regulate the space between droplets (now containing completed dimerization screening assay reactions), and a detector is used to detect the level of fluorescence in each droplet. The detector can be any device or method for interrogating a droplet as it passes through a detection region. Typically, droplets are sorted according to one or more predetermined characteristics that are directly or indirectly detectable, and the detector is adapted to detect the characteristic. In the present dimerization screening assays using, e.g., a fluorescent reporter, one detector of particular use is an optical detector, such as a microscope or spectrophotometer and measured by a photo multiplier tube or other image processing or enhancement device, which may be coupled to a computer to digitize the signal may control the flow of the droplets via, e.g., valve action or an electroosmotic potential.

The droplets are analyzed and sorted based on the intensity of a signal detected as the droplets pass through a detection region or window. Droplets having a level of reporter below a selected threshold or within a selected range are diverted into a predetermined outlet or reservoir. For example, a droplet-sorting device may comprise a spectrophotometer where the fluorescent intensity of each droplet is read as it passes by the light beam. The optical signal is collected and projected onto a cathode of a photomultiplier tube. Optionally, part of the light may be directed onto a charge-coupled device (CCD) camera for imaging. As the droplets pass by the spectrophotometer detection window, the droplets are directed to conduits that lead to the reservoirs that collect fluorescing droplets and empty droplets depending on, e.g., acoustic, electric, magnetic, and optical fields to impose forces to displace droplets for sorting.

Following sorting into, e.g., a microtube or other container, the emulsion is broken thereby pooling the reaction mixes including the binding pairs (i.e., dimerizers) comprising DNA-encoded putative dimerizers. The identity of the putative dimerizers can be determined by sequencing the DNA codes in the pooled reaction mix. See MacConnel, et al., ACS Comb. Sci., 19:181-92 (2017) for a description of functional screens using DNA-encoded compound beads in a microfluidic circuit.

Kits

The components of the dimerization screening cascade assays may be provided in various kits. In one embodiment, the kit for detecting a dimerization event includes: 1) dimerizer/N-terminal portion of split Cas enzyme; 2) dimerizer/C-terminal portion of split Cas; 3) first guide nucleic acids (gRNA1); 4) RNP1 activating nucleic acids; 5) RNP2s; 6) blocked nucleic acid molecules; and 7) reporter moieties (see FIG. 3A and the description thereof). In a second embodiment, the kit for detecting a dimerization event includes in one aspect: 1) dimerizer/N-terminal portion of split Cas enzyme; 2) dimerizer/C-terminal portion of split Cas enzyme; 3) first guide nucleic acids (gRNA1); 4) RNP1 activating nucleic acids; 5) RNP2s; 6) linear template molecules (which is the non-target strand); 7) circular blocked primer molecules; 8) a polymerase; and 9) reporter moieties (see FIG. 4A and the description thereof). An alternative aspect of the second embodiment provides a kit for detecting a dimerization even comprising: dimerizer/N-terminal portion of split Cas enzyme; 2) dimerizer/C-terminal portion of split Cas enzyme; 3) first guide nucleic acids (gRNA1); 4) RNP1 activating nucleic acids; 5) RNP2s; 6) circular template molecules (which is the non-target strand); 7) circular blocked primer molecules; 8) a polymerase; and 9) reporter moieties (see FIG. 4B and the description thereof). In a third embodiment, the kit for detecting a dimerization event comprises: 1) dimerizer/N-terminal portion of split Cas enzyme; 2) dimerizer/C-terminal portion of split Cas enzyme; 3) first guide nucleic acids (gRNA1); 4) RNP1 activating nucleic acids; 5) intact second Cas enzyme; 6) RNP2 activating nucleic acids; 7) blocked guide molecules i.e., the (blocked gRNA2s); and 8) reporter moieties (see FIG. 5A and the description thereof above).

As an alternative, the kits may comprise N- and C-terminal portions of the split nucleic acid-guided nuclease coupled to a linker and reagents that allow coupling of the linker-comprising N- and C-terminal portions of the split nucleic acid-guided nuclease to desired dimerizers. In yet another alternative, the kits may comprise N- and C-terminal portions of the split nucleic acid-guided nuclease and a selection of linkers and reagents that allow coupling of the different linkers to the N- and C-terminal portions of the split nucleic acid-guided nuclease and then further allow coupling of the linker-comprising N—and C-terminal portions of the split nucleic acid-guided nuclease to desired dimerizers. Each component of the kit may be in separate container or two or more components may be in the same container. The kit may further include reagents for conducting the dimerization screening assays in droplets (or other assay formats), including an aqueous reagent mix solution and an immiscible fluid for the carrier phase. In addition, the kit may further include instructions for use and other information.

EXAMPLES

The following examples are put forth so as to provide those of ordinary skill in the art with a complete disclosure and description of how to make and use the present invention and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: RNP Formation

For RNP complex formation, 250 nM of LbCas12a nuclease protein was incubated with 375 nM of a target specific gRNA in 1× Buffer (10 mM Tris-HCl, 100 μg/mL BSA) with 2-15 mM $MgCl_2$ at 25° C. for 20 minutes. The total reaction volume was 241L. Other ratios of LbCas12a nuclease to gRNAs were tested, including 1:1, 1:2 and 1:5. The incubation temperature ranged from 20° C.-37° C., and the incubation time ranged from 10 minutes to 4 hours.

Example II: Determination of N-terminal and C-terminal Split for Cas Enzyme

Figure 8:
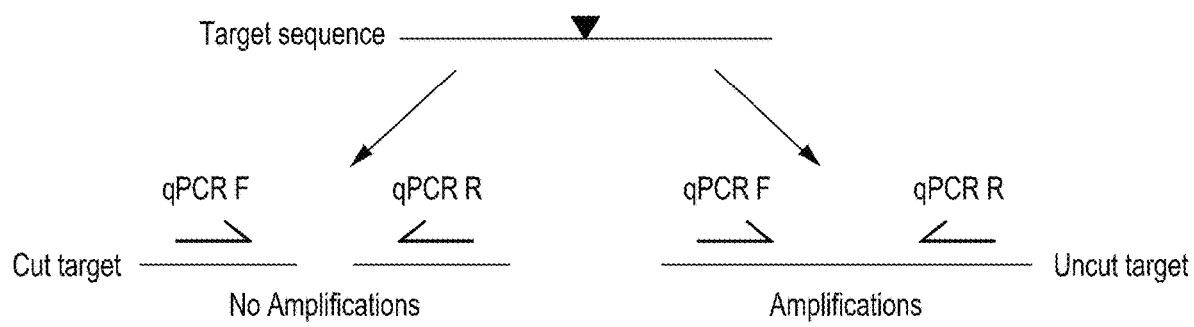
FIG. 8 shows a simplified screening assay for identifying viable N-terminal and C-terminal splits for the nucleic acid-guided nuclease employed in the first ribonucleoprotein complex, according to certain embodiments.

PCR Readout: To measure cut activity of each split protein pair, 2 μL (quantity varies due to translation efficiency) from an in-vitro translation reaction is pooled together with 1 μL 300 nM gRNA and 4 μL with 1X NEB cut smart buffer (9 μL total). An RNP is allowed to form for 20 minutes followed by addition of 1 μL of 100 nM target DNA (10 nM final). Digestion reactions are incubated at 37° C. for 2 hrs to allow complete digestion and then moved to −20° C. until qPCR reactions are ready. Following digestion, 1 μL of the digestion reaction is used as template in a qPCR reaction using, e.g., an SSO advanced kit from Bio Rad, Hercules, CA, USA and following the manufacturer's instructions to determine the remaining un-cut or intact target DNA concentration. Split protein pairs that exhibit a lack of cleavage in the absence of donor DNA and >90% cleavage of input material in the presence of the donor DNA are considered candidates for follow on characterization (see FIG. 8). Absolute quantification of the % digest completion is determined from calibration curves of titrated undigested target. Controls of purified Cas enzyme-gRNA RNP complex+30 nM gRNA and no-enzyme are used to confirm gRNA activity and establish baselines for further normalization of overall activity donor DNA dependence.

Example III: Blocked Nucleic Acid Molecule Formation

Ramp cooling: For formation of the secondary structure of blocked nucleic acids, 2.5 μM of a blocked nucleic acid molecule (any of Formulas I-IV) was mixed in a T50 buffer (20 mM Tris HCl, 50 mM NaCl) with 10 mM $MgCl_2$ for a total volume of 50 μL. The reaction was heated to 95° C. at 1.6° C./second and incubated at 95° C. for 5 minutes to dehybridize any secondary structures. Thereafter, the reaction was cooled to 37° C. at 0.015° C./second to form the desired secondary structure.

Snap cooling: For formation of the secondary structure of blocked nucleic acids, 2.5 μM of a blocked nucleic acid molecule (any of Formulas I-IV) was mixed in a T50 buffer (20 mM Tris HCl, 50 mM NaCl) with 10 mM $MgCl_2$ for a total volume of 50 μL. The reaction was heated to 95° C. at 1.6° C./second and incubated at 95° C. for 5 minutes to dehybridize any secondary structures. Thereafter, the reaction was cooled to room temperature by removing the heat source to form the desired secondary structure.

Snap cooling on ice: For formation of the secondary structure of blocked nucleic acids, 2.5 µM of a blocked nucleic acid molecule (any of Formulas I-IV) was mixed in a T50 buffer (20 mM Tris HCl, 50 mM NaCl) with 10 mM MgCl$_2$ for a total volume of 50 µL. The reaction was heated to 95° C. at 1.6° C./second and incubated at 95° C. for 5 minutes to dehybridize any secondary structures. Thereafter, the reaction was cooled to room temperature by placing the reaction tube on ice to form the desired secondary structure.

Example IV: Reporter Moiety Formation

The reporter moieties used in the reactions herein were single-stranded DNA oligonucleotides 5-9 bases in length (e.g., with sequences of TTATT, TTTATTT, ATTAT, ATTT-ATTTA, AAAAA, or AAAAAAAAA) with a fluorophore and a quencher attached on the 5' and 3' ends, respectively. In one example using a Cas12a cascade, the fluorophore was FAM-6 and the quencher was IOWA BLACK® (Integrated DNA Technologies, Coralville, IA). In another example using a Cas13 cascade, the reporter moieties were single-stranded RNA oligonucleotides 5-10 bases in length (e.g., r(U)n, r(UUAUU)n, r(A)n).

While certain embodiments have been described, these embodiments have been presented by way of example only and are not intended to limit the scope of the present disclosures. Indeed, the novel methods, apparatuses, modules, instruments and systems described herein can be embodied in a variety of other forms; furthermore, various omissions, substitutions and changes in the form of the methods, apparatuses, modules, instruments and systems described herein can be made without departing from the spirit of the present disclosures. The accompanying claims and their equivalents are intended to cover such forms or modifications as would fall within the scope and spirit of the present disclosures.

I claim:

1. A method for identifying a dimerization of binding partners comprising the steps of:
providing a reaction mixture comprising:
a fusion molecule comprising a first binding partner and an N-terminal portion of a split Cas enzyme, wherein the split Cas enzyme when reconstituted with the N-terminal portion and a C-terminal portion is capable of trans-cleavage nuclease activity;
first guide nucleic acids;
RNP1 activating nucleic acids, wherein the RNP1 activating nucleic acids comprise a sequence complementary to the first guide nucleic acids, and wherein binding of an RNP1 complex formed by reconstituting the split Cas enzyme and the first guide nucleic acid to the RNP1 activating nucleic acid activates trans-cleavage activity of the split Cas enzyme;
RNP2s, wherein the RNP2s comprise a second guide nucleic acid and an intact second Cas enzyme comprising trans-cleavage nuclease activity and wherein the second intact Cas enzyme is a different Cas enzyme than the split Cas enzyme; and
a plurality of blocked nucleic acid molecules comprising a sequence complementary to the second guide nucleic acid; and
contacting the reaction mixture with a sample comprising a library of fusion molecules comprising putative second binding partners and the C-terminal portions of the split Cas enzyme under conditions that allow putative second binding partners to bind to the first binding partner of the fusion molecule comprising the first binding partner and the N-terminal portion of the split Cas enzyme, and wherein if one of the putative second binding partners in the library of putative second binding partners binds to the first binding partner, the split Cas enzyme is reconstituted and forms an RNP1 with the first guide nucleic acids and RNP1 activating nucleic acids thereby initiating trans-cleavage of at least one of the blocked nucleic acid molecules and thereby producing at least one unblocked nucleic acid molecule, and wherein the at least one unblocked nucleic acid molecule binds to RNP2 initiating cleavage of at least one further blocked nucleic acid molecule; and
detecting the at least one unblocked nucleic acid molecule, thereby detecting dimerization of binding partners in the sample.

2. The method of claim 1, wherein one or both of RNP1 and RNP2 comprises a nucleic acid-guided nuclease selected from Cas3, Cas12a, Cas12b, Cas12c, Cas12d, Cas12e, Cas14, Cas 12h, Cas 12i, Cas 12j, Cas 13a, or Cas 13b.

3. The method of claim 1, wherein one or both of RNP1 and RNP2 comprises a nucleic acid-guided nuclease that is a Type V nucleic acid-guided nuclease or a Type VI nucleic acid-guided nuclease.

4. The method of claim 1, wherein one or both of RNP1 and RNP2 comprises a nucleic acid-guided nuclease comprising a RuvC nuclease domain or a RuvC-like nuclease domain but lacks an HNH nuclease domain.

5. The method of claim 1, further comprising reporter moieties, wherein the reporter moieties produce a detectable signal upon trans-cleavage activity by the RNP1 and/or RNP2 to identify a presence of one or more non-nucleic acid targets of interest in the sample.

6. The method of claim 1, wherein the first binding partner is an antigen and the second binding partner is a library of antibodies, or wherein the first binding partner is a library of antibodies and the second binding partner is an antigen.

7. The method of claim 1, wherein the reaction mixture further comprises a molecular glue candidate, and wherein the first binding partner is an effector and the second binding partner is a target or the first binding partner is a target and the second binding partner is an effector.

8. The method of claim 1, wherein the first binding partner is a non-nucleic acid target and the second binding partner is a library of aptamers, or wherein the first binding partner is a library of aptamers and the second binding partner is a non-nucleic acid target.

9. The method of claim 1, wherein the N-terminal and C-terminal portions of the split Cas enzyme are coupled to the first binding partner and putative second binding partner with a linker.

10. The method of claim 9, wherein the linkers covalently couple the N-terminal and C-terminal portions of the split Cas enzyme to the first binding partner and putative second binding partner.

11. The method of claim 9, wherein the linkers that couple the N-terminal and C-terminal portions of the split Cas enzyme to the first binding partner and putative second binding partner are peptide linkers.

12. The method of claim 9, wherein the linkers that couple the N-terminal and C-terminal portions of the split Cas enzyme to the first binding partner and putative second binding partner are cleavable.

13. The method of claim 9, wherein the linkers that couple the N-terminal and C-terminal portions of the split Cas enzyme to the first binding partner and putative second binding partner are non-cleavable.

14. The method of claim 1, wherein the blocked nucleic acid molecules comprise a structure represented by any one of Formulas I-IV, wherein Formulas I-IV are in the 5'-to-3' direction:
  (a) A–(B–L)$_J$–C–M–T–D (Formula I);
    wherein A is 0-15 nucleotides in length;
    B is 4-12 nucleotides in length;
    L is 3-25 nucleotides in length;
    J is an integer between 1 and 10;
    C is 4-15 nucleotides in length;
    M is 1-25 nucleotides in length or is absent, wherein if M is absent then A-(B–L)$_J$-C and T–D are separate nucleic acid strands;
    T is 17-135 nucleotides in length and comprises at least 50% sequence complementarity to B and C; and
    D is 0-10 nucleotides in length and comprises at least 50% sequence complementarity to A;
  (b) D–T–T'–C–(L–B)$_J$–A (Formula II);
    wherein D is 0-10 nucleotides in length;
    T-T' is 17-135 nucleotides in length;
    T' is 1-10 nucleotides in length and does not hybridize with T;
    C is 4-15 nucleotides in length and comprises at least 50% sequence complementarity to T;
    L is 3-25 nucleotides in length and does not hybridize with T;
    B is 4-12 nucleotides in length and comprises at least 50% sequence complementarity to T;
    J is an integer between 1 and 10;
    A is 0-15 nucleotides in length and comprises at least 50% sequence complementarity to D;
  (c) T–D–M–A–(B–L)$_J$–C (Formula III);
    wherein T is 17-135 nucleotides in length;
    D is 0-10 nucleotides in length;
    M is 1-25 nucleotides in length or is absent, wherein if M is absent then T–D and A-(B-L)$_J$-C are separate nucleic acid strands;
    A is 0-15 nucleotides in length and comprises at least 50% sequence complementarity to D;
    B is 4-12 nucleotides in length and comprises at least 50% sequence complementarity to T;
    L is 3-25 nucleotides in length;
    J is an integer between 1 and 10; and
    C is 4-15 nucleotides in length; or
  (d) T–D–M–A–L$_p$–C (Formula IV);
    wherein T is 17-31 nucleotides in length;
    D is 0-15 nucleotides in length;
    M is 1-25 nucleotides in length;
    A is 0-15 nucleotides in length and comprises a sequence complementary to D; and
    L is 3-25 nucleotides in length;
    p is 0 or 1;
    C is 4-15 nucleotides in length and comprises a sequence complementary to T.

15. The method of claim 1, wherein
  (a) T of Formula I comprises at least 80% sequence complementarity to B and C;
  (b) D of Formula I comprises at least 80% sequence complementarity to A;
  (c) C of Formula II comprises at least 80% sequence complementarity to T;
  (d) B of Formula II comprises at least 80% sequence complementarity to T;
  (e) A of Formula II comprises at least 80% sequence complementarity to D;
  (f) A of Formula III comprises at least 80% sequence complementarity to D;
  (g) B of Formular III comprises at least 80% sequence complementarity to T;
  (h) A of Formula IV comprises at least 80% sequence complementarity to D; and/or
  (i) C of Formula IV comprises at least 80% sequence complementarity to T.

16. A reaction mixture for detecting dimerization of binding partners comprising:
  one or more fusion molecules comprising a first binding partner and an N-terminal portion of a split Cas enzyme and one or more fusion molecules comprising a second binding partner and a C-terminal portion of the split Cas enzyme, wherein the split Cas enzyme when reconstituted with the N-terminal and the C-terminal portions is capable of exhibiting trans-cleavage nuclease activity;
  first guide nucleic acids;
  RNP1 activating nucleic acids, wherein the RNP1 activating nucleic acids comprise a sequence complementary to the first guide nucleic acids, and wherein binding of the RNP1 activating nucleic acids to an RNP1 complex formed by reconstituting the split Cas enzyme and the first guide nucleic acid activates trans-cleavage activity of the split Cas enzyme;
  RNP2s, wherein the RNP2s comprise a second guide nucleic acid and an intact second Cas enzyme comprising trans-cleavage nuclease activity and wherein the second intact Cas enzyme is a different Cas enzyme than the split Cas enzyme; and a plurality of blocked nucleic acid molecules comprising a sequence complementary to the second guide nucleic acid.

17. The reaction mixture of claim 16, wherein one or both of RNP1 and RNP2 comprises a nucleic acid-guided nuclease that is a Type V nucleic acid-guided nuclease or a Type VI nucleic acid-guided nuclease.

18. The reaction mixture of claim 16, wherein one or both of RNP1 and RNP2 comprises a nucleic acid-guided nuclease comprising a RuvC nuclease domain or a RuvC-like nuclease domain but lacks an HNH nuclease domain.

19. The reaction mixture of claim 16, further comprising reporter moieties, wherein the reporter moieties produce a detectable signal upon trans-cleavage activity by the RNP1 and/or RNP2 to identify a presence of one or more non-nucleic acid targets of interest in the sample.

20. The reaction mixture of claim 16, wherein the first binding partner is an antigen and the second binding partner is a library of antibodies, or wherein the first binding partner is a library of antibodies and the second binding partner is an antigen.

21. The reaction mixture of claim 16, wherein the reaction mixture further comprises a molecular glue candidate, and wherein the first binding partner is an effector and the second binding partner is a target or the first binding partner is a target and the second binding partner is an effector.

22. The reaction mixture of claim 16, wherein the first binding partner is a non-nucleic acid target and the second binding partner is a library of aptamers, or wherein the first binding partner is a library of aptamers and the second binding partner is a non-nucleic acid target.

23. The reaction mixture of claim 16, wherein the N-terminal and C-terminal portions of the split Cas enzyme are coupled to the first binding partner and putative second binding partner with a linker.

24. The reaction mixture of claim 23, wherein the linkers covalently couple the N-terminal and C-terminal portions of the split Cas enzyme to the first binding partner and putative second binding partner.

25. The reaction mixture of claim 23, wherein the linkers that couple the N-terminal and C-terminal portions of the split Cas enzyme to the first binding partner and putative second binding partner are peptide linkers.

26. The reaction mixture of claim 23, wherein the linkers that couple the N-terminal and C-terminal portions of the split Cas enzyme to the first binding partner and putative second binding partner are cleavable.

27. The reaction mixture of claim 23, wherein the linkers that couple the N-terminal and C-terminal portions of the split Cas enzyme to the first binding partner and putative second binding partner are non-cleavable.

28. The reaction mixture of claim 16 wherein the blocked nucleic acid molecules comprise a structure represented by any one of Formulas I-IV, wherein Formulas I-IV are in the 5'-to-3' direction:

(e) $A-(B-L)_J-C-M-T-D$ (Formula I);
wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then $A-(B-L)_J-C$ and T-D are separate nucleic acid strands;

T is 17-135 nucleotides in length and comprises at least 50% sequence complementarity to B and C; and
D is 0-10 nucleotides in length and comprises at least 50% sequence complementarity to A;

(f) $D-T-T'-C-(L-B)_J-A$ (Formula II);
wherein D is 0-10 nucleotides in length;
T-T' is 17-135 nucleotides in length;
T' is 1-10 nucleotides in length and does not hybridize with T;
C is 4-15 nucleotides in length and comprises at least 50% sequence complementarity to T;
L is 3-25 nucleotides in length and does not hybridize with T;
B is 4-12 nucleotides in length and comprises at least 50% sequence complementarity to T;
J is an integer between 1 and 10;
A is 0-15 nucleotides in length and comprises at least 50% sequence complementarity to D;

(g) $T-D-M-A-(B-L)_J-C$ (Formula III);
wherein T is 17-135 nucleotides in length;
D is 0-10 nucleotides in length;
M is 1-25 nucleotides in length or is absent, wherein if M is absent then T-D and $A-(B-L)_J-C$ are separate nucleic acid strands;
A is 0-15 nucleotides in length and comprises at least 50% sequence complementarity to D;
B is 4-12 nucleotides in length and comprises at least 50% sequence complementarity to T;
L is 3-25 nucleotides in length;
J is an integer between 1 and 10; and
C is 4-15 nucleotides in length; or (h) $T-D-M-A-L_p-C$ (Formula IV);
wherein T is 17-31 nucleotides in length;
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

29. The reaction mixture of claim 28, wherein
a) T of Formula I comprises at least 80% sequence complementarity to B and C;
b) D of Formula I comprises at least 80% sequence complementarity to A;
c) C of Formula II comprises at least 80% sequence complementarity to T;
d) B of Formula II comprises at least 80% sequence complementarity to T;
e) A of Formula II comprises at least 80% sequence complementarity to D;
f) A of Formula III comprises at least 80% sequence complementarity to D;
g) B of Formular III comprises at least 80% sequence complementarity to T;
h) A of Formula IV comprises at least 80% sequence complementarity to D; and/or
i) C of Formula IV comprises at least 80% sequence complementarity to T.

* * * * *

```
                        SEQUENCE LISTING

Sequence total quantity: 11
SEQ ID NO: 1            moltype = AA  length = 10
FEATURE                 Location/Qualifiers
source                  1..10
                        mol_type = protein
                        organism = synthetic construct
SEQUENCE: 1
CGLVPAGSGP                                                                10

SEQ ID NO: 2            moltype = AA  length = 12
FEATURE                 Location/Qualifiers
source                  1..12
                        mol_type = protein
                        organism = Synthetic construct
SEQUENCE: 2
SLLKSRMVPN FN                                                             12

SEQ ID NO: 3            moltype = AA  length = 12
FEATURE                 Location/Qualifiers
source                  1..12
                        mol_type = protein
                        organism = synthetic construct
SEQUENCE: 3
SLLIARRMPN FN                                                             12

SEQ ID NO: 4            moltype = AA  length = 12
FEATURE                 Location/Qualifiers
source                  1..12
                        mol_type = protein
                        organism = synthetic construct
SEQUENCE: 4
SKLVQASASG VN                                                             12

SEQ ID NO: 5            moltype = AA  length = 12
FEATURE                 Location/Qualifiers
source                  1..12
                        mol_type = protein
                        organism = synthetic construct
SEQUENCE: 5
SSYLKASDAP DN                                                             12

SEQ ID NO: 6            moltype = RNA  length = 45
FEATURE                 Location/Qualifiers
source                  1..45
                        mol_type = other RNA
                        organism = synthetic construct
SEQUENCE: 6
taatttctac taagtgtaga tgagaagtca tttaataagg ccact                         45

SEQ ID NO: 7            moltype = DNA  length = 24
FEATURE                 Location/Qualifiers
source                  1..24
```

```
                        mol_type = other DNA
                        organism = synthetic construct
SEQUENCE: 7
gagaagtcat ttaataaggc cact                                              24

SEQ ID NO: 8            moltype = DNA  length = 24
FEATURE                 Location/Qualifiers
source                  1..24
                        mol_type = other DNA
                        organism = synthetic construct
SEQUENCE: 8
ctcttcagta aattattccg gtga                                              24

SEQ ID NO: 9            moltype = RNA  length = 54
FEATURE                 Location/Qualifiers
source                  1..54
                        mol_type = other RNA
                        organism = synthetic construct
SEQUENCE: 9
nnnnnnnnnn ntatttctac taagtgtaga tgagagtcat ttaataaggc cact             54

SEQ ID NO: 10           moltype = RNA  length = 53
FEATURE                 Location/Qualifiers
source                  1..53
                        mol_type = other RNA
                        organism = synthetic construct
SEQUENCE: 10
nnnnnnnnta atttctacta agtgtagatg agaagtcatt taataaggcc act              53

SEQ ID NO: 11           moltype = RNA  length = 56
FEATURE                 Location/Qualifiers
source                  1..56
                        mol_type = other RNA
                        organism = synthetic construct
SEQUENCE: 11
nnnnnnnnnn ntaatttcta ctaagtgtag atgagaagtc atttaataag gccact           56
```